(12) United States Patent
Vizbaras et al.

(10) Patent No.: US 11,298,057 B2
(45) Date of Patent: Apr. 12, 2022

(54) TUNABLE HYBRID III-V/IV LASER SENSOR SYSTEM-ON-A-CHIP FOR REAL-TIME MONITORING OF A BLOOD CONSTITUENT CONCENTRATION LEVEL

(71) Applicants: Brolis Sensor Technology, UAB, Vilnius (LT); Universiteit Gent, Ghent (BE); IMEC VZW, Leuven (BE)

(72) Inventors: Augustinas Vizbaras, Vilnius (LT); Kristijonas Vizbaras, Vilnius (LT); Ieva Šimonytė, Vilnius (LT); Günther Roelkens, Schellebelle (BE)

(73) Assignees: Brolis Sensor Technology, UAB, Vilnius (LT); Universiteit Gent, Ghent (BE); IMEC VZW, Leuven (BE)

( * ) Notice: Subject to any disclaimer, the term of this patent is extended or adjusted under 35 U.S.C. 154(b) by 0 days.

(21) Appl. No.: 17/369,517

(22) Filed: Jul. 7, 2021

(65) Prior Publication Data

US 2021/0353183 A1     Nov. 18, 2021

Related U.S. Application Data

(63) Continuation of application No. 16/609,355, filed as application No. PCT/EP2018/063260 on May 21, 2018.

(Continued)

(51) Int. Cl.
*A61B 5/1455* (2006.01)
*H01S 5/026* (2006.01)
(Continued)

(52) U.S. Cl.
CPC .......... *A61B 5/1455* (2013.01); *G01N 21/39* (2013.01); *H01S 5/026* (2013.01); *H01S 5/125* (2013.01); *H01S 5/20* (2013.01)

(58) Field of Classification Search
CPC ...... A61B 5/1455; G01N 21/39; H01S 5/026; H01S 5/125; H01S 5/20
See application file for complete search history.

(56) References Cited

U.S. PATENT DOCUMENTS

| 4,912,451 A | 3/1990 | Sugiyama et al. |
| 5,442,221 A | 8/1995 | Mosser et al. |

(Continued)

FOREIGN PATENT DOCUMENTS

| AU | 6502500 A | 2/2001 |
| AU | 1305802 A | 4/2002 |

(Continued)

OTHER PUBLICATIONS

Are Alvor Aastveit et al., "Near-Infrared Reflectance Spectroscopy: Different Strategies For Local Calibrations In Analyses of Forage Quality", Applied Spectroscropy, The Society For Applied Sprectroscopy, Baltimore, US, vol. 47, No. 4, Apr. 1, 1993 (Apr. 1, 1993), pp. 463-469, XP000356631, ISSN: 0003-7028, DOI: 10.1366/0003702934334912.

(Continued)

*Primary Examiner* — Yuanda Zhang
(74) *Attorney, Agent, or Firm* — Goodwin Procter LLP

(57) ABSTRACT

A spectroscopic laser sensor based on hybrid III-V/IV system-on-a-chip technology. The laser sensor is configured to either (i) be used with a fiber-optic probe connected to an intravenous/intra-arterial optical catheter for direct invasive blood analyte concentration level measurement or (ii) be used to measure blood analyte concentration level non-invasively through an optical interface attached, e.g., to the skin or fingernail bed of a human. The sensor includes a III-V gain-chip, e.g., an AlGaInAsSb/GaSb based gain-chip and a photonic integrated circuit, with laser wavelength filtering, laser wavelength tuning, laser wavelength monitoring, laser signal monitoring and signal output sections (Continued)

realized on a chip by combining IV-based semiconductor substrates and flip-chip AlGaInAsSb/GaSb based photodetectors and embedded electronics for signal processing. Embodiments of the invention may be applied for real-time monitoring of critical blood analyte concentration levels such as lactates, urea, glucose, ammonia, albumin, etc.

10 Claims, 28 Drawing Sheets

Related U.S. Application Data

(60) Provisional application No. 62/595,283, filed on Dec. 6, 2017, provisional application No. 62/539,759, filed on Aug. 1, 2017, provisional application No. 62/509,301, filed on May 22, 2017.

(51) Int. Cl.
*G01N 21/39* (2006.01)
*H01S 5/125* (2006.01)
*H01S 5/20* (2006.01)

(56) References Cited

U.S. PATENT DOCUMENTS

| | | |
|---|---|---|
| 5,456,206 A | 10/1995 | Lee et al. |
| 5,657,189 A | 8/1997 | Sandhu |
| 5,945,676 A | 8/1999 | Khalil et al. |
| 6,205,159 B1 | 3/2001 | Sesko et al. |
| 6,316,124 B1 | 11/2001 | Boos et al. |
| 6,327,036 B1 | 12/2001 | Bao et al. |
| 6,345,059 B1 | 2/2002 | Flanders |
| 6,442,413 B1 | 8/2002 | Silver |
| 6,567,433 B2 | 5/2003 | May |
| 6,587,484 B1 | 7/2003 | May |
| 6,600,760 B1 | 7/2003 | Green et al. |
| 6,611,341 B2 | 8/2003 | May |
| 6,633,593 B2 | 10/2003 | Ksendzov et al. |
| 6,671,296 B2 | 12/2003 | May |
| 6,690,687 B2 | 2/2004 | Ksendzov et al. |
| 6,693,928 B2 | 2/2004 | May |
| 6,714,309 B2 | 3/2004 | May |
| 6,728,279 B1 | 4/2004 | Sarlet et al. |
| 6,816,636 B2 | 11/2004 | Cole et al. |
| 6,816,743 B2 | 11/2004 | Moreno et al. |
| 6,853,654 B2 | 2/2005 | McDonald et al. |
| 6,879,619 B1 | 4/2005 | Green et al. |
| 6,888,856 B2 | 5/2005 | Green et al. |
| 7,027,470 B2 | 4/2006 | May |
| 7,061,943 B2 | 6/2006 | Coldren et al. |
| 7,120,176 B2 | 10/2006 | McDonald et al. |
| 7,230,963 B2 | 6/2007 | Menon et al. |
| 7,295,783 B2 | 11/2007 | Singh et al. |
| 7,356,364 B1 | 4/2008 | Bullock et al. |
| 7,388,235 B2 | 6/2008 | Boos et al. |
| 7,460,567 B2 | 12/2008 | May |
| 7,495,838 B2 | 2/2009 | Krneta et al. |
| 7,502,532 B2 | 3/2009 | McCallion et al. |
| 7,564,548 B2 | 7/2009 | Flanders et al. |
| 7,773,642 B2 | 8/2010 | Yamazaki |
| 8,164,748 B1 | 4/2012 | Flanders et al. |
| 8,311,067 B2 | 11/2012 | Ensher et al. |
| 8,452,356 B2 | 5/2013 | Vestel et al. |
| 8,467,051 B2 | 6/2013 | Flanders et al. |
| 8,831,050 B2 | 9/2014 | Gao |
| 9,559,484 B2 | 1/2017 | Morton et al. |
| 9,583,913 B1 | 2/2017 | Fang et al. |
| 9,608,406 B1* | 3/2017 | Lee ..................... H01S 5/1032 |
| 9,653,882 B1 | 5/2017 | Zheng et al. |
| 9,692,207 B2 | 6/2017 | Fang et al. |
| 9,748,726 B1 | 8/2017 | Morton et al. |
| 9,755,753 B2 | 9/2017 | Blumenthal |
| 2001/0021803 A1 | 9/2001 | Blank et al. |
| 2002/0091324 A1 | 7/2002 | Kollias et al. |
| 2003/0016707 A1 | 1/2003 | McDonald et al. |
| 2004/0064022 A1* | 4/2004 | Korn .................... A61B 5/0075 600/342 |
| 2005/0261561 A1 | 11/2005 | Jones et al. |
| 2006/0193354 A1 | 8/2006 | Rosenblatt |
| 2006/0238775 A1 | 10/2006 | Lopushansky et al. |
| 2007/0004759 A1 | 1/2007 | Tormo i Blasco et al. |
| 2007/0047599 A1 | 3/2007 | Wysocki et al. |
| 2007/0179367 A1 | 8/2007 | Ruchti et al. |
| 2008/0086038 A1* | 4/2008 | Thornton ............ H01S 3/09415 600/310 |
| 2008/0139906 A1 | 6/2008 | Bussek |
| 2009/0141748 A1 | 6/2009 | Koyama et al. |
| 2012/0032147 A1* | 2/2012 | Nagai ................ H01L 27/1446 257/21 |
| 2013/0016744 A1 | 1/2013 | Li et al. |
| 2013/0182729 A1 | 7/2013 | Li et al. |
| 2014/0138746 A1 | 5/2014 | Abrokwah et al. |
| 2014/0176958 A1 | 6/2014 | Flanders et al. |
| 2014/0307753 A1 | 10/2014 | Minneman et al. |
| 2015/0282716 A1 | 10/2015 | Smeltzer et al. |
| 2015/0349485 A1 | 12/2015 | Selwan et al. |
| 2016/0161685 A1 | 6/2016 | Xu et al. |
| 2016/0282265 A1 | 9/2016 | Su et al. |
| 2016/0345872 A1 | 12/2016 | Wasson et al. |
| 2016/0356959 A1 | 12/2016 | Jayatilleka et al. |
| 2017/0141536 A1 | 5/2017 | Fang et al. |
| 2017/0163009 A1 | 6/2017 | Choi |
| 2020/0069225 A1 | 3/2020 | Vizbaras et al. |

FOREIGN PATENT DOCUMENTS

| | | |
|---|---|---|
| AU | 1305902 A | 4/2002 |
| AU | 3054602 A | 5/2002 |
| AU | 2002239673 A1 | 7/2002 |
| AU | 2002362396 A1 | 4/2003 |
| CA | 2559990 A1 | 10/2005 |
| CN | 1316696 A | 10/2001 |
| CN | 1554139 A | 12/2004 |
| CN | 1938917 A | 3/2007 |
| CN | 103515840 A | 1/2014 |
| CN | 104568751 A | 4/2015 |
| CN | 104568907 A | 4/2015 |
| CN | 105140777 A | 12/2015 |
| CN | 104568907 B | 4/2017 |
| EP | 1214762 A1 | 6/2002 |
| EP | 1354382 A2 | 10/2003 |
| EP | 1436864 A2 | 7/2004 |
| EP | 1737090 A1 | 12/2006 |
| EP | 2575220 A2 | 4/2013 |
| EP | 3002568 A1 | 4/2016 |
| JP | 2004-528701 A | 9/2004 |
| JP | 2008-301944 A | 12/2008 |
| JP | 2009-238972 A | 10/2009 |
| JP | 2012-89651 A | 5/2012 |
| KR | 100837126 B1 | 6/2008 |
| TW | 200537773 A | 11/2005 |
| WO | WO-0108277 A1 | 2/2001 |
| WO | WO-0231931 A2 | 4/2002 |
| WO | WO-0231933 A2 | 4/2002 |
| WO | WO-0235667 A2 | 5/2002 |
| WO | WO-2002054544 A2 | 7/2002 |
| WO | WO-02082599 A1 | 10/2002 |
| WO | WO-03030311 A2 | 4/2003 |
| WO | WO-2004015826 A1 | 2/2004 |
| WO | WO-2005096462 A1 | 10/2005 |
| WO | WO-2005099421 A2 | 10/2005 |
| WO | WO-2011/029886 A1 | 3/2011 |
| WO | WO-2015018352 A1 | 2/2015 |
| WO | WO-2017/021971 A1 | 2/2017 |
| WO | WO-2018215388 A1 | 11/2018 |

OTHER PUBLICATIONS

Duan et al, "Hybrid III—V on Silicon Lasers for Photonic Integrated Circuits on Silicon", IEEE Journal of Selected Topcis in Quantum Electronics, vol. 20, No. 4, Jul. 1, 2014, pp. 158-170.

(56) References Cited

OTHER PUBLICATIONS

Friedland et al., "New Concept for the reduction of impurity scattering in remotely doped GaAs quantum wells," Phys. Rev. Lett., vol. 77, No. 22, 1996.

Hayne et al., "Remote impurity scattering in modulation-doped GaAs/ Al,Ga 1_.As heterojunctions", Phys. Rev. B., vol. 57, No. 23, 1998.

International Search Report and Written Opinion in PCT/EP2014/062672 dated Mar. 17, 2015, 11 pages.

International Search Report and Written Opinion dated Nov. 18, 2013 in PCT/EP2013/0717, 12 pages.

International Search Report and Written Opinion dated Sep. 26, 2018 in PCT/EP2018/063260, 19 pages.

Roelkens et al., "III-V-on-Silicon Photonic Devices for Optical Communication and Sensing", Photonics, vol. 2, No. 3, Sep. 18, 2015, pp. 969-1004.

Kraus et al., "Optimization of the doping levels in doubly doped InAlAs/InGaAs HEMTs," Compound Semiconductors 1997, Proceedings of the IEEE24th International Symposium on Compound Semiconductors, San Diego, CA, Sep. 8-11, 1997, pp. 503-508.

Pavlovska, et al., "in situ studies of the role of excess Ga on the growth morphology of thin GaN layers," Surface Science, vol. 496, (2002), pp. 160-178.

R. Wang, et al., "Compact GaSb/silicon-on-insulator 2.0x μm widely tunable external cavit lasers," Optics Express, 24 (25), 28977-28986 (2016).

Roelkens et al."III-V-on-Silicon Photonic Devices for Optical Communicaiton and Sensing", Photonics, vol. 2, No. 3, Sep. 18, 2015, pp. 969-1004.

Saxena et al., "Determination of alloy scattering potential in $Ga_{1-x}Al_x$As alloys," J. Appl. Phys., vol. 58, 2640, 1985.

Songlin Yu, et al., "In vitro glucose measurement using tunable mid-infrared laser spectroscopy combined with fiber-optic sensor", Dec. 17, 2013.

Tormod Naes et al., "Splitting of Calibration Data By Cluster Analyisis", Journal of Chemometrics, Wiley, Chichester, Sussex, England, GB, vol. 5, No. 1, Jan. 1, 1991 (Jan. 1, 1991), pp. 49-65, XP000171347, ISSN: 0886-9383, DOI: 10.1002/CEM.1180050106.

Tuttle et al., "Effects of interface layer sequencing on the transport properties of InAs/ AlSb quantum wells: evidence for anti site donors at the InAs/ AlSb interface," J. Appl. Phys., 67, 3032 (1990).

Yao Zhanshi et al.., "Integrated Silicon Photonic Microresonators: Emerging Technologies", IEEE Journal of Selected Topics in Quantum Electronics, Service Center, Piscataway, NJ, US, vol. 24, No. 6, Nov. 1, 2018 (Nov. 1, 2018), pp. 1-24, XP011685808, ISSN: 1077-260X, DOI: 10.1109/JSTQE.2018.2846047 [retrieved on Jun. 21, 2018].

International Search Report and Written Opinion dated Jul. 26, 2019 in PCT/EP2019/052367, 27 pages.

Komlenovic et al., "Widely-Tunable Ring-Resonator Semiconductor Lasers" Applied Sciences, 2017, 7(7); 732, 21 pages.

Lin, Hongtao et al., "Mid-infared integrated photonics on silicon: a perspective", Nanophotonics, 2018; 7(2): 393-420.

Ohtsu M. et al., "A simple interferometric method for monitoring mode hopping in tunable external-cavity semiconductor lasers", Journal of Lightwave Technology, IEEE, USA, vol. 7, No. 1, Jan. 1, 1989, pp. 68-76.

R. Wang et al., "III-V-on-Silicon Photonic Integrated Circuits for Spectroscopic Sensing in the 2-4 um Wavelength Range", Sensors 17 (8), 1788, 2017.

\* cited by examiner

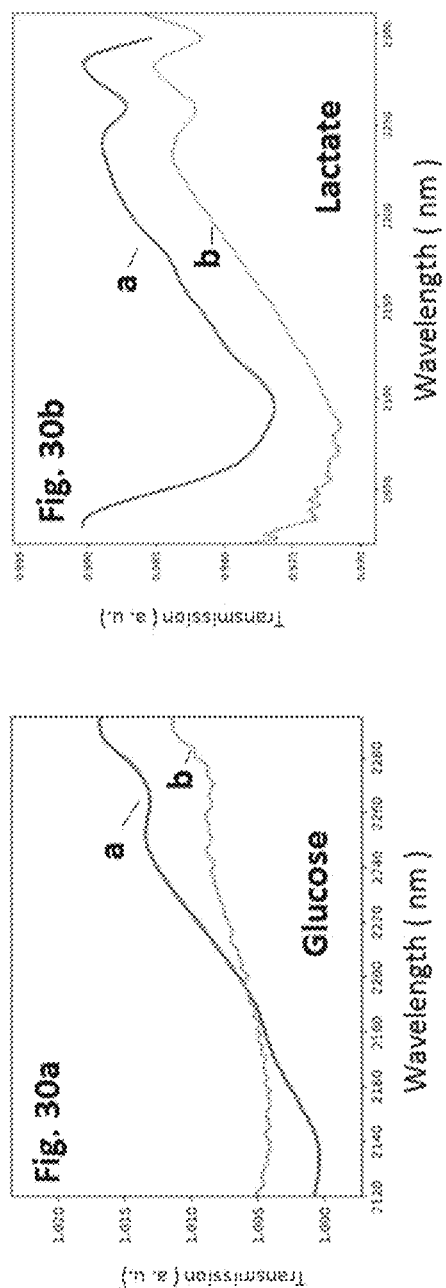
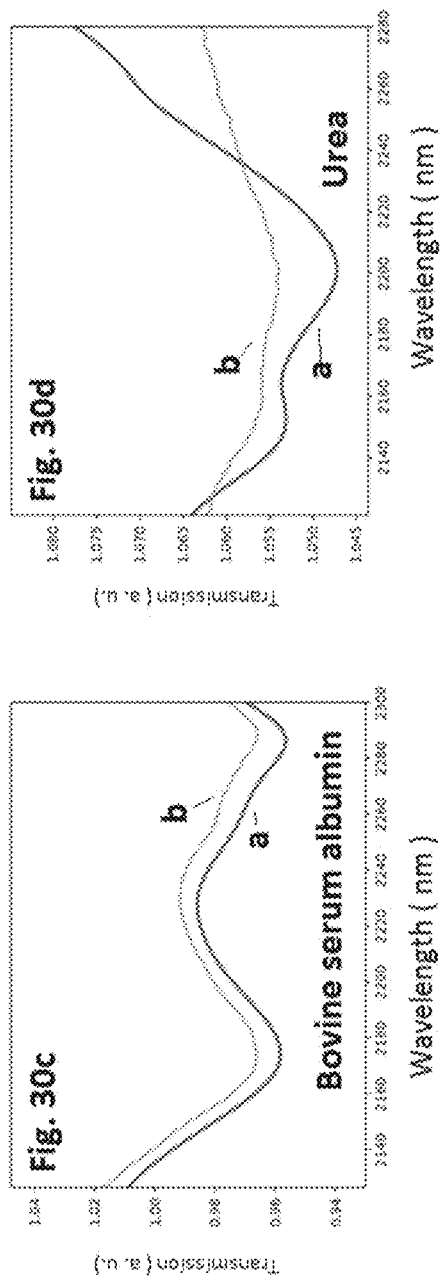
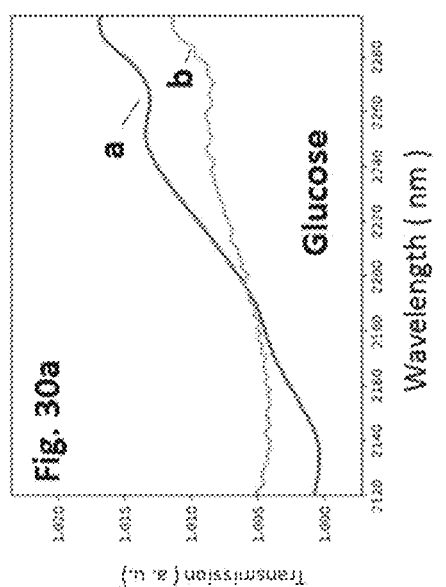
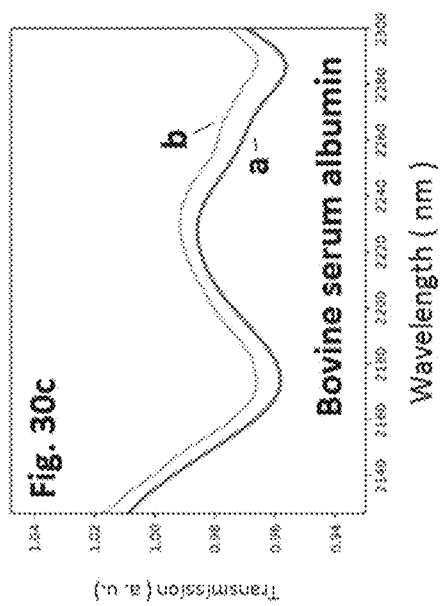
Fig. 30a Glucose
Fig. 30b Lactate
Fig. 30c Bovine serum albumin
Fig. 30d Urea ＃ TUNABLE HYBRID III-V/IV LASER SENSOR SYSTEM-ON-A-CHIP FOR REAL-TIME MONITORING OF A BLOOD CONSTITUENT CONCENTRATION LEVEL

RELATED APPLICATIONS

This application is a continuation application of U.S. patent application Ser. No. 16/609,355 filed on Oct. 29, 2019, which is a U.S. national stage application, filed under 35 U.S.C. § 371, of International Application No. PCT/EP2018/063260 filed on May 21, 2018, which claims the benefit of priority to U.S. Provisional Application Ser. No. 62/509,301 filed May 22, 2017, U.S. Provisional Application Ser. No. 62/539,759 filed Aug. 1, 2017, and U.S. Provisional Application Ser. No. 62/595,283 filed Dec. 6, 2017, each of which is incorporated herein by reference in its entirety.

FIELD OF THE INVENTION

Embodiments of the invention relate generally to semiconductor-based spectroscopic sensors based on hybrid III-V/IV system-on-a-chip technology for real-time continuous monitoring of blood analyte concentration levels in a human body, such as blood lactate and blood glucose concentration level monitoring.

BACKGROUND

According to American Association for Clinical Chemistry (AACC), blood analytes such as glucose, lactate, urea, creatinine, ammonia, albumin and others are considered as most important blood analytes in critical care medicine which are required to be monitored in order to diagnose and treat such critical cases as sepsis, organ dysfunction and failure, hypoxia, diabetes, dehydration, and others.

In some case, such as sepsis, which has high mortality rate in excess of 30%, time is a critical factor and real-time monitoring of important blood analytes such as lactate is of paramount importance and can directly affect the survivability of the patient. It is reported that in case of sepsis, mortality increases by 8% with every hour of treatment delay; therefore, timely diagnosis is of paramount importance. Only in USA, sepsis alone is responsible for over 250 000 cases that result in death, which is the third most common cause of death in US. Moreover, sepsis was the most expensive in-patient cost in American hospitals in 2014, at nearly 24 billion USD each year. See www.sepsis.com/definition and http://www.sepsis.org/faq/, accessed Mar. 10, 2017 and incorporated herein by reference in its entirety. Timely diagnosed sepsis combined with proper treatment is a critical factor that could save patients' lives. Lactate is a prognostic marker in case of sepsis and real-time monitoring of blood lactate level is critical for early warning as well as treatment effectiveness.

Earlier works have reported on various monitoring techniques including those that utilize light. See U.S. Patent Publication Nos. 2014/0176958 and 2012/0226118, and U.S. Pat. Nos. 6,442,413 and 5,945,676, incorporated herein by reference in their entireties. These reported systems, however, are either implantable, use moving parts such as MEMS mirrors, and/or use broadband sources not related to III-V/IV technology. Implantable sensors often carry additional risks related to biocompatibility and risk of additional infection as well as they have limitations in terms of implanting location for direct monitoring which can be a limiting factor in some applications. Broadband sources suffer from poor spectral power density and require complex wavelength discrimination schemes such as waveguide arrays and photodetector arrays (2×12 or similar as in U.S. Patent Publication No. 2012/0226118.)

SUMMARY

A sensor in accordance with embodiments of the invention can enter an existing intravascular, i.e., an intravenous or intra-arterial catheter that has an optical fiber interface, thus allowing the sensor to be used for direct blood metabolite level measurement in real-time. This is especially useful in critical care, such as intensive care units and operating theaters where blood metabolite concentration level accuracy is critical and especially in particular cases such as sepsis, where blood metabolite level can differ within the body.

Embodiments of the configurations described herein provide a significant advantage. For example, existing methods of lactate level measurement typically are implemented at point of care or at remote lab testing. This results in test turn-around time ranging from a few minutes to a few hours. In particular, point-of-care testing typically requires a few minutes turn-around time for a test that is non-real time— i.e., the blood has to be drawn from the patient and processed by an instrument providing a single data point. Real-time measurements, in accordance with embodiments of the invention, allow for continuous collection of multiple data points over a period of time providing important information of the historic trend that can be vital in evaluating effectiveness of treatment.

For applications where accuracy is less critical and where blood metabolite level differences within the body is of less significance such as in case of athletics and professional sports, a non-invasive solution sending light through tissue from outside can be used. The latter solution may be used by medical clinics for patients outside intensive care units (ICUs) and operating theaters as early warning systems together with other existing measurements, such as oximetry, without excess burden on the patient. Moreover, improving early warning prevention of such complicated cases like sepsis is expected to save significant costs in terms of treatment and hospital stay.

Embodiments of the invention include sensors based on a widely tunable laser concept realized in III-V/IV technology, III-V refers to semiconductor materials based on AlGaIn-NAsSbP and different combination thereof, typically known as III-V semiconductors to those skilled in the art. IV refers to group IV-based semiconductor substrates and their technology platforms such as silicon, silicon-on-insulator (SOI), germanium-on-insulator (GOI), germanium on silicon, silicon nitride on silicon, silicon nitride-on-insulator, and silicon nitride-on-silicon-on-insulator. The group IV technology uses processes that are standard industrial CMOS fabrication steps used in the microelectronics industry and allow realization of photonic integrated circuits based on group IV materials and their derivatives. The non-implantable sensors do not have any moving mechanical parts, and offer direct blood metabolite concentration level measurement in real-time by means of laser absorption spectroscopy. An exemplary widely tunable laser may be manufactured by a hybrid combination of GaSb based gain-chip active medium and external filter realized in a silicon, a silicon nitride, silicon-on-insulator, silicon nitride-on-silicon-on-insulator, silicon nitride on insulator or a germanium-on-insulator platform chip. See e.g., R. Wang et al., Optics Express, 24 (25), 28977-28986 (2016), the disclosure of which is specifically intended to be incorporated herein as part of this disclosure in its entirety to illustrate the fabrication and use of widely tunable lasers. This laser is combined with simple wavelength control circuitry and a few GaSb-based photodiodes for signal detection to provide high signal brightness and, thereby, sensitivity.

In an aspect, embodiments of the invention relate to a laser-based sensor system-on-a-chip for real-time monitoring of a blood constituent concentration level in a subject. The system-on-a-chip includes (i) a tunable hybrid III-V/IV laser sensor; and (ii) a fiber-optic interface coupled to the laser sensor, the interface including a probe. During use, the laser sensor is remote from the subject and the probe is in optical communication with the subject.

One or more of the following features may be included. IV includes group-IV based semiconductor substrate such as silicon, silicon-on-insulator, silicon nitride on silicon-on-insulator, germanium-on-insulator, and silicon nitride on silicon. The tunable laser sensor may include a III-V gain-chip and a photonic integrated circuit disposed on a group IV semiconductor such as silicon-on-insulator, silicon nitride, silicon nitride on silicon on insulator, germanium-silicon or germanium-on-insulator substrate, the photonic integrated circuit (i) being configured to perform wavelength filtering and tuning functions based on Vernier effect and (ii) defining an external cavity for the III-V gain-chip.

The photonic integrated circuit may include a spot-size mode converter, a phase control section, and a first resonator having a first free-spectral range coupled to a second resonator having a second free-spectral range. The first and second resonators may be, e.g., micro ring resonators, sampled Bragg reflectors, or distributed feedback reflectors. The first free-spectral range may be different from the second free-spectral range.

The coupled first and second resonators, the III-V gain-chip, spot-size mode converter, and phase control section may cooperate to enable Vernier effect-based tuning of the tunable laser sensor. The tunable laser sensor may be configured such that, in operation, applying at least one of current or heat to at least one of the coupled resonators to change an effective refractive index thereof effects a change in a wavelength of a laser generated by the gain-chip.

The III-V gain-chip may be edge-coupled to the photonic integrated circuit, e.g., by a grating coupler.

The laser sensor may include at least one III-V photodiode coupled to a photonic integrated circuit by at least one of flip-chip bonding, gluing, transfer printing technology, or side coupling.

A discrete III-V photodiode may be disposed remotely from the tunable laser sensor, wherein, in use, a reflected signal from the subject is collected by the discrete III-V photodiode. The photonic integrated circuit may include a signal and wavelength monitoring section. The signal and wavelength monitoring section may include (i) at least one of a set of Mach-Zehnder interferometers or coupled ring resonators, and (ii) at least one flip-chip III-V photodiode. The laser sensor may further include laser drive electronics and a signal processing microcontroller. The microcontroller may be configured to (i) control the laser drive electronics, (ii) tune currents, and (iii) use information from the wavelength and signal monitor section for signal processing of the data obtained from the discrete III-V photodiode.

The laser sensor may be configured to perform a wavelength sweep across a tuning range as a function of time, and the laser sensor may include a photodiode configured to convert light reflected from the subject into an electrical signal.

The fiber-optic interface may be connected to an optical catheter and configured to (i) transmit a light signal from the sensor to blood of the subject and (ii) transmit reflected light from the blood of the subject to the sensor.

The fiber optic interface may be in optical communication with beam shaping optics configured to non-invasively illuminate a blood sample of the subject through the subject's skin or outer tissue.

In another aspect, embodiments of the invention relate to a method of manufacturing a tunable hybrid III-V/IV laser sensor. The method includes the steps of (i) manufacturing a III-V semiconductor gain-chip; (ii) fabricating a photonic integrated circuit on a IV-based semiconductor substrate by CMOS technology to define a group IV semiconductor chip; and (iii) hybridly integrating the III-V gain-chip and the group-IV semiconductor chip. The photonic integrated circuit is configured to perform wavelength filtering and tuning functions based on Vernier effect, and defines an external cavity for the III-V gain-chip.

One or more of the following features may be included. Hybridly integrating the III-V gain-chip and the group IV semiconductor chip may include edge-coupling the III-V gain-chip to the group-IV semiconductor chip, actively aligning the two chips, and gluing the two chips together.

Hybridly integrating the chips may include flipping the III-V gain-chip p-side down and bonding the gain-chip into a trench defined in the group-IV semiconductor chip for edge coupling to the photonic integrated circuit.

Manufacturing the III-V semiconductor gain-chip may include epitaxially growing a laser layer structure on a substrate by at least one of MBE or MOVPE growth.

The laser layer structure on the substrate may be processed into a gain-chip device including predefined waveguide angles and contact pads.

The laser layer structure on the substrate may be cleaved into bars. The bars may be cleaved into a plurality of individual III-V semiconductor gain-chips.

An anti-reflection coating may be formed on an output facet, with power reflection being less than 0.1% at the output facet. A high-reflectivity coating may be formed on a back facet, with power reflectivity being at least 90% or higher on the back facet.

A photonic integrated circuit may be designed according to properties of the III-V gain-chip, the photonic integrated circuit comprising at least one of a spot size converter and a Vernier-filter.

A sensor may include an array of cells, each cell including a laser-based sensor system-on-a chip as described above, each array cell being targeted at a different spectral region and a separate target molecule.

A wavelength swept laser signal of each array cell may be emitted at a different time, and signal collection may be realized by synchronized detection with a single photodiode.

The fiber-optic interface may include an out-coupling fiber having a core. An output of the array may be formed by a group of grating couplers from the individual array cells routed to a same portion of the system-on-a-chip. A total area defined by the group of grating couplers is smaller than a cross-sectional area of the out-coupling fiber core.

The sensor may further include a single output section, a wavelength switch configured to switch between outputs of the array cells, and a single photodiode. An output of the sensor array is formed by the single output section and the wavelength switch. Switching between outputs of each individual cell results in a single output of one array cell being out-coupled to the target at a given time. Signal collection is realized by synchronized detection with the single photodiode.

The sensor of claim may include at least one array cell is targeted at a spectral region corresponding to at least one peak of water absorption selected from the group consisting of ~1460 nm, ~1900-2000 nm, and ~3000 nm, and (ii) at least one other array cell is targeted at a spectral region corresponding to at least one absorption peak of a blood constituent target molecule.

The sensor of may further include at least one central processing unit programmed to determine a water concentration level and a water absorption spectrum based on the at least one peak of water absorption measured with the at least one array cell.

The central processing unit may be further programmed to remove a baseline and decompose a complex absorbance spectrum in spectral regions covered by array cells adjacent to the at least one array cell to reveal underlying target molecule absorption features.

The central processing unit may be further programmed to convert diffuse reflectance spectra to absorbance. The absorbance may include a collected absorbance spectrum having a plurality of individual absorbance spectral components decoupled by using information from adjacent array cells operating in different spectral regions where no overlap with other molecular absorption exists. The central processing unit may be further programmed to correct and remove a baseline in spectral regions where absorption spectral features of more than one target molecule overlap. The central processing unit may be further programmed to determine a calibrated concentration level using at least one of the individual absorbance spectral components. The calibrated concentration level may be determined based on an individual absorbance value and a calibrated attenuation coefficient for each of a plurality of individual molecules at a given wavelength. The central processing unit may be further programmed to determine a target molecule concentration independently of a particular sample volume.

In another aspect, embodiments of the invention relate to a laser-based sensor system-on-a-chip for real-time monitoring of a blood constituent concentration level in a subject. The system-on-a-chip includes (i) a tunable hybrid III-V/IV laser sensor; and (ii) an optical interface coupled to the laser sensor, the interface including beam-shaping optics. During use, the laser sensor is remote from the subject and the optical interface is configured to non-invasively illuminate a blood sample of the subject through the subject's skin or outer tissue.

One or more of the following features may be included. A sensor may include an array of cells, each cell comprising a laser-based sensor system-on-a chip including a tunable laser sensor and optical interface as described above. Each array cell may be targeted at a different spectral region and a separate target molecule.

An individual output of each array cell may be focused to illuminate a single area of the subject, and each reflected signal is collected from the illuminated area by the beam shaping optics. The beam shaping optics may include at least one optical element, e.g., a lens, a set of mirrors, and/or a parabolic mirror.

In still another aspect, embodiments of the invention relate to a method of real-time monitoring of a blood constituent level in a subject, including providing a system-on-a-chip. The system-on-a-chip includes a tunable hybrid III-V/IV laser sensor, a fiber-optic interface coupled to the laser sensor, the surface including a probe, sensor control electronics for sensor control and signal processing, and a signal processing microcontroller. The laser sensor is disposed remote from the subject and the probe in optical communication with the subject. The system-on-a chip is instructed to monitor the blood constituent level in the subject by sending a swept laser signal to the fiber optic interface. The signal is guided with the fiber optic interface to the blood of the subject. After the signal interacts with the blood, the fiber-optic interface collects a reflected signal from the blood. The reflected signal is guided to a reflected light photodiode, the reflected signal being an optical signal. The reflected signal is converted by the sensor control electronics from an optical signal to an electrical signal. The electrical signal is processed with the microcontroller to convert the electrical signal into a calibrated blood constituent level.

One or more of the following features may be included. The probe may be connected to at least one of an intravenous optical catheter or an intra-arterial optical catheter for invasive blood analyte concentration level measurement. The optical interface may be attached to the subject for non-invasive blood analyte concentration level measurement. The blood constituent may include or consist essentially of, e.g., lactate, albumin, glucose, ammonia, creatinine, and/or urea.

The various embodiments described above represent individual features of the invention which can be applied generally to the system of the invention. These features may be taken individually as preferred features or more than one of these preferred features may be combined with one another in any combination.

BRIEF DESCRIPTION OF THE DRAWINGS

FIGS. 30A-30D are transmission spectra of different molecular solutions measured using a widely tunable laser sensor and a reference measurement with a commercial table-top FTIR spectrometer;

DETAILED DESCRIPTION

Embodiments of the invention include a hybrid III-V/IV system on-a chip sensor for real-time continuous blood constituent monitoring. The described embodiments allow the realization of a widely wavelength-swept laser-based sensor with wavelength, phase, and power control on a single chip without any moving parts in the infrared wavelength range for direct molecular sensing of blood constituents such as lactate, albumin, glucose, ammonia, creatinine, urea, etc. The sensing is performed with direct laser absorption spectroscopy by scanning the laser wavelength across the absorption band of the target molecule. Since the spectroscopic absorption signature is unique to the individual molecule, the described embodiments have an advantage of direct sensing. The specific embodiments described below may be used in combination or interchangeably depending on the context. It is specifically intended in this disclosure that individual features of the sensor system of the invention which are disclosed in relation to any of the above figures may be considered more generally to represent features of the invention as a whole. Thus, for example, particular features of the sensor described in FIG. 1 may be combined with particular features concerning the feature of the system on a chip as described in FIGS. 18, 20, 21 and 22. Similarly, for example, particular features of the sensor described in FIG. 1 may be combined with particular features concerning the III-V/VI chip as described in FIGS. 5 to 12 etc. Likewise, particular features of the system on the chip may be combined with particular features of the III-V/IV chip architecture etc.

Hybrid semiconductor technology is used, in which the active gain medium is realized in a III-V semiconductor structure in the form of a gain-chip or semiconductor optical amplifier that is coupled to a passive photonic integrated circuit realized on a group IV-based semiconductor substrate such as silicon, silicon-on-insulator (SOI), germanium-on-insulator (GOI), germanium on silicon, silicon nitride on silicon, silicon nitride-on-insulator, silicon nitride-on-silicon-on-insulator. The group IV technology uses processes that are standard industrial CMOS fabrication steps used in the microelectronics industry and allow realization of photonic integrated circuits based on group IV materials and their derivatives. This approach enables the described sensor technology to be scalable, very-low form factor, low-cost, and applicable to mass market applications such as personalized health monitoring, athletics by means of wearable technology or individual patient health monitoring by entering a clip-on non-invasive bedside system. Further, accurate sensors can provide valuable information by entering a fiber-optic base intravascular optical catheter or other invasive probe for direct contact to patient's blood.

Figure 1A:
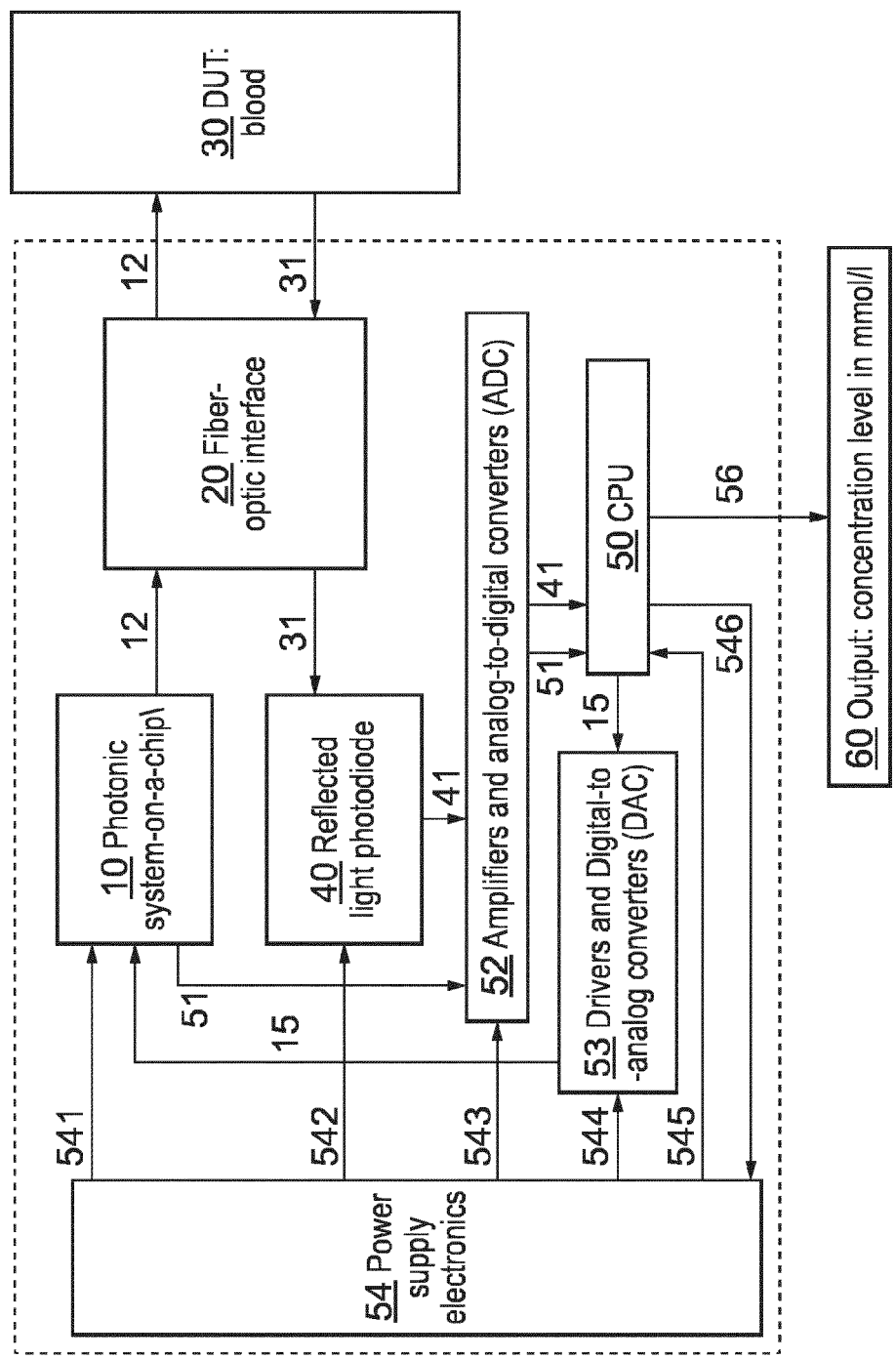
FIGS. 1A, 1B, and 1C are schematic block diagrams of continuous monitoring systems for blood analyte concentration level, in accordance with embodiments of the invention.
Figure 1B:
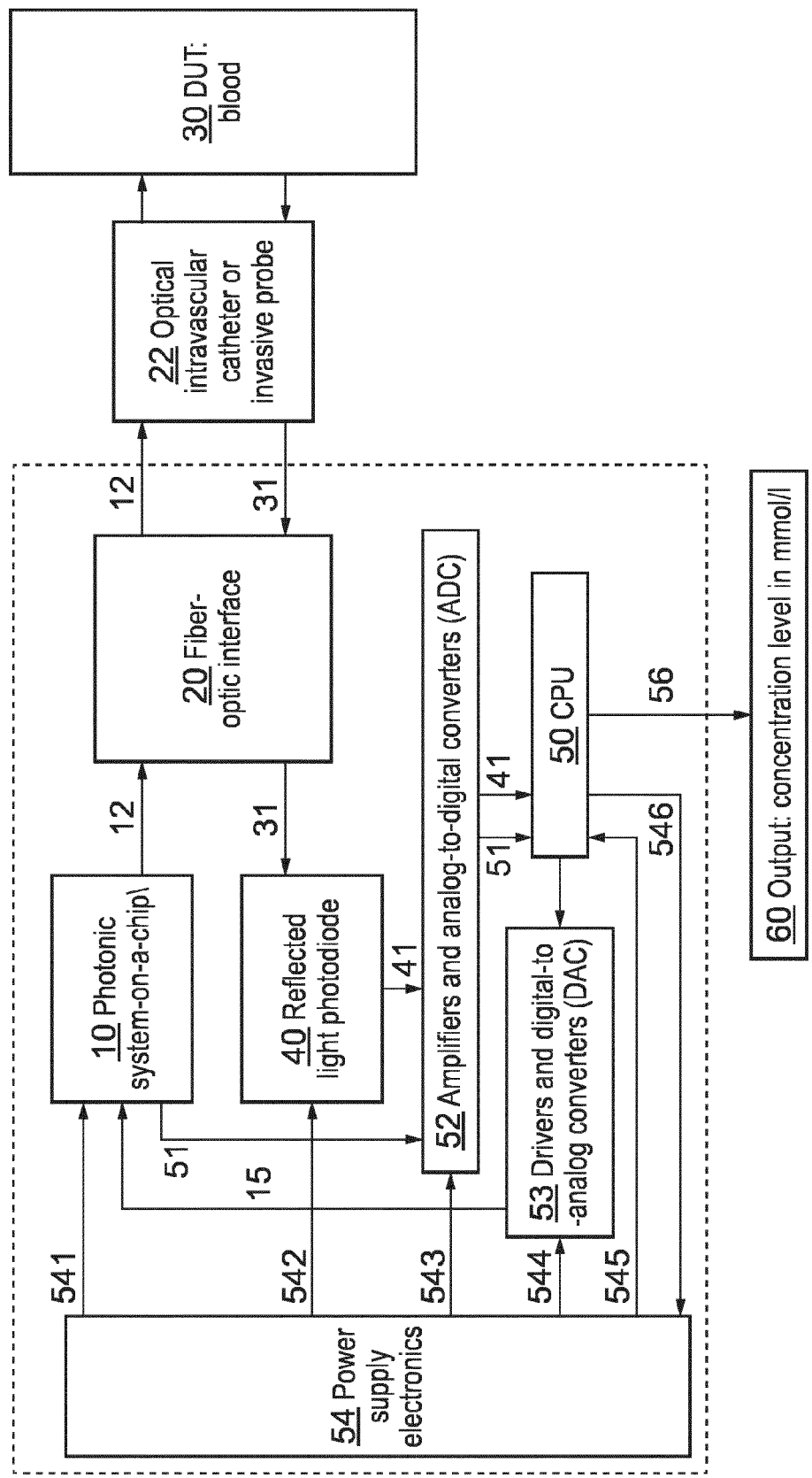
Figure 1C:
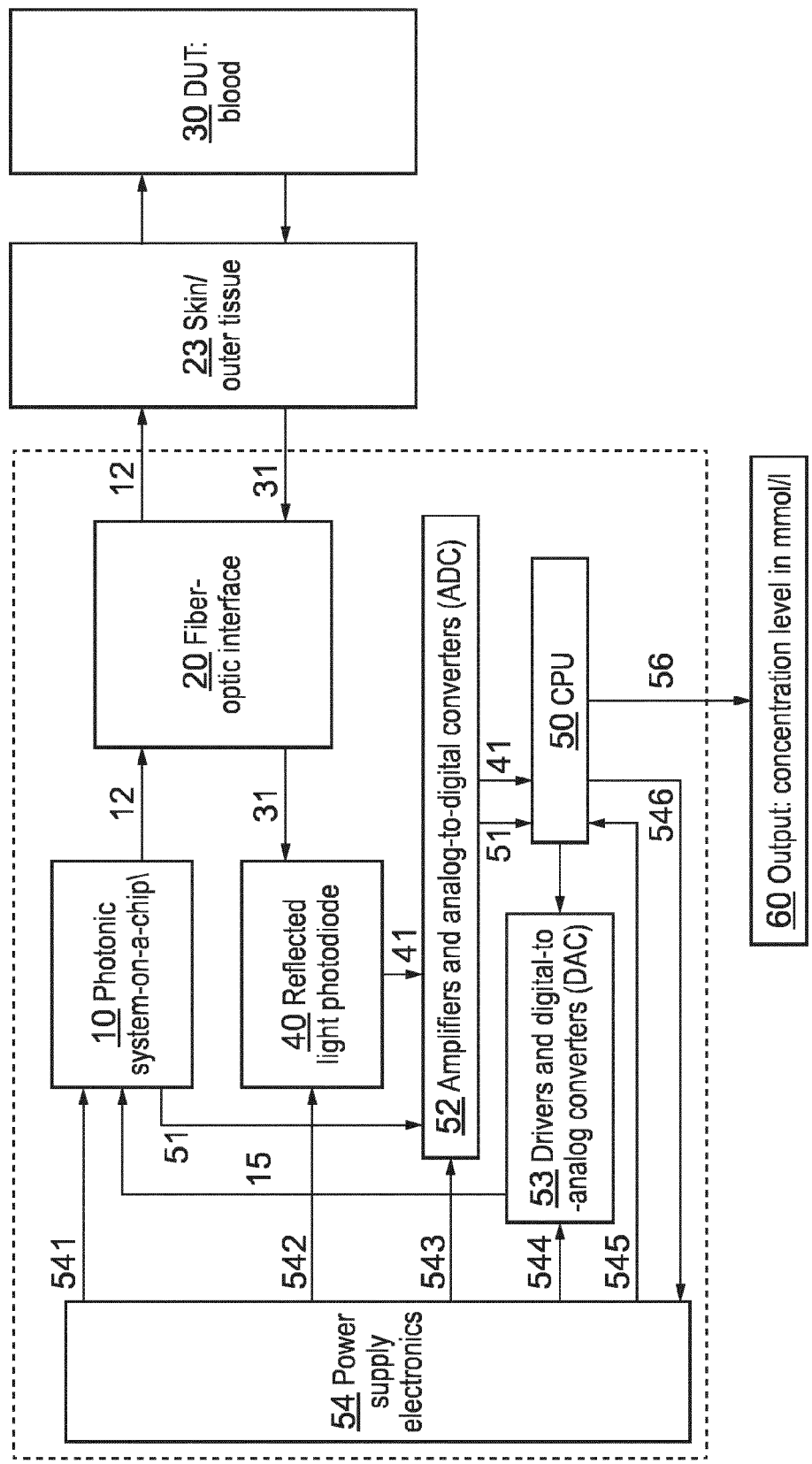

Embodiments of the invention include a laser sensor including a photonic system-on-a-chip, a fiber-optic interface for signal delivery and collection of reflected light, a reflected signal photodiode, and a digital signal processor for sensor control and signal processing (see FIGS. 1A-1C and related discussion).

The photonic system-on-a-chip includes a widely wavelength-tunable laser cavity, with, e.g., an AlGaInAsSb broadband gain-chip designed to emit in 1800 nm-3500 nm wavelength range edge-coupled to a group IV semiconductor based photonic integrated circuit in which wavelength tuning, filtering, monitoring and out-coupling are realized (see discussion below with respect to FIG. 2).

The sensor principle is based on tunable laser absorption spectroscopy, with a laser wavelength sweep performed across a spectral range where molecular absorption bands due to rotational-vibrational states of the molecule are present. The wavelength is absorbed by the vibration of the target molecule leading to a change in the reflected signal (photon-phonon interaction). The wavelength is swept as a function of time. Therefore, spectral information is recovered by a single detector in contrast to prior art methods, such as the methods disclosed in U.S. Patent Publication No. 2012/0226118. In addition, wavelength and signal control sections enable knowledge of the laser wavelength tuning curve at all times and allow discrimination between system-based distortions from sample-based distortions.

In embodiments of the invention, light with known properties (exact wavelength, power and tuning curve) is generated and may be coupled to a fiber through which the light is coupled onto a sample—either direct contact of fiber probe tip to blood containing the molecule of interest or through skin towards blood containing vessel/tissue.

As discussed below with respect to FIG. 3, by choosing the correct laser design, the laser emission spectrum can be chosen to selectively target a molecule of interest. For example, the molecule of interest may be a lactate molecule, which has distinct spectral absorption bands related to C—H and O—H molecular stretch vibration overtone combination bands around 2260 nm and 2300 nm. Depending on the application requirements, the external cavity laser needs to be designed to have a laser tuning bandwidth >50 nm to recover the shape of the specific absorption feature.

Figure 4:
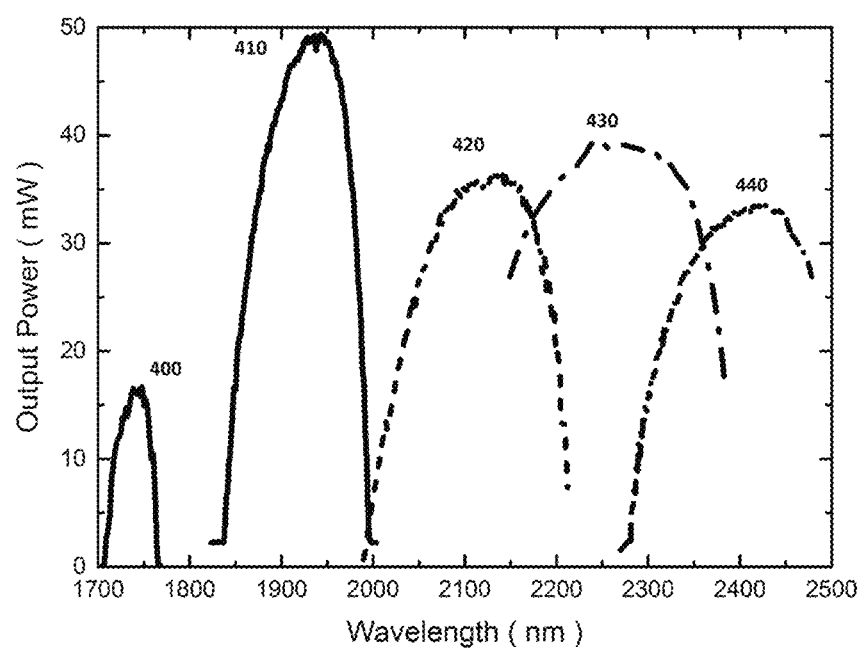
FIG. 4 is experimental laser wavelength tuning spectrum obtained for an AlGaInAsSb/GaSb gain-chip based external cavity lasers, in accordance with an embodiment of the invention, with numbered spectra belong to different III-V gain-chips embedded in an external cavity configuration.

As discussed with respect to FIG. 4, the disclosed laser-based sensors have the ability to sweep wavelengths across a bandwidth of 50 nm or more at a rate of 10 Hz to several kHz range and allow for real-time monitoring. AlGaInAsSb based gain-chips offer gain-bandwidth in excess of 150 nm and can be designed to target any central wavelength within 1700-2500 nm by changing the epitaxial layer design. Other materials such as AlGaInAsP and AlGaInAsSbP can be used to further broaden the wavelength coverage from 1000 nm-3500 nm and beyond. The wavelength selection, tuning and monitoring is realized in the group IV semiconductor based photonic integrated circuit chip.

In the described embodiments, the wavelength tuning requirement enables wavelength sweep across several tens of nm at a rate up to several kHz. This is achieved by enabling an external cavity to form a Vernier-filter in which coupled resonators with slightly different free-spectral range values are coupled together. A discussion of theory on Vernier tuning and different ways of achieving it may be found in, e.g., J. Buus, M.-C. Amann, D. J. Blumenthal, Tunable Laser Diodes and Related Optical Sources, $2^{nd}$ Edition, John Willey & Sons, Inc., 2005. The disclosure of this document and in particular the principles described therein are specifically incorporated by reference herein in its entirety and are intended to form part of this disclosure.

The maximum tuning range of such Vernier-filter laser is limited by the free-spectral range of the Vernier filter:

$$\Delta \lambda = \left| \frac{FSR1 \cdot FSR2}{FSR1 - FSR2} \right| \quad \text{(Formula 1)}$$

where FSR1,2 is the free-spectral range of the first and second resonators, respectively. The transmission function of such filter has a maximum where the resonant peaks of individual resonators overlap, determining the laser emission wavelength. The wavelength is swept by applying heat and/or current to at least one of the resonators, which induces a refractive index change and therefore the transmission overlap position. In other words, changing the effective refractive index of a resonator effects a change in a wavelength of a laser generated by the gain-chip. Such a filter can be realized by a combination of coupled micro-ring resonators with different cavity lengths or sampled-grating distributed Bragg reflector (DBR) designs. See, e.g., U.S. Patent Application Publication No. 20040228384 to Oh et al., which is incorporated by reference herein in its entirety and the fabrications described in this disclosure are specifically intended to form part of the present disclosure.

Figure 5:
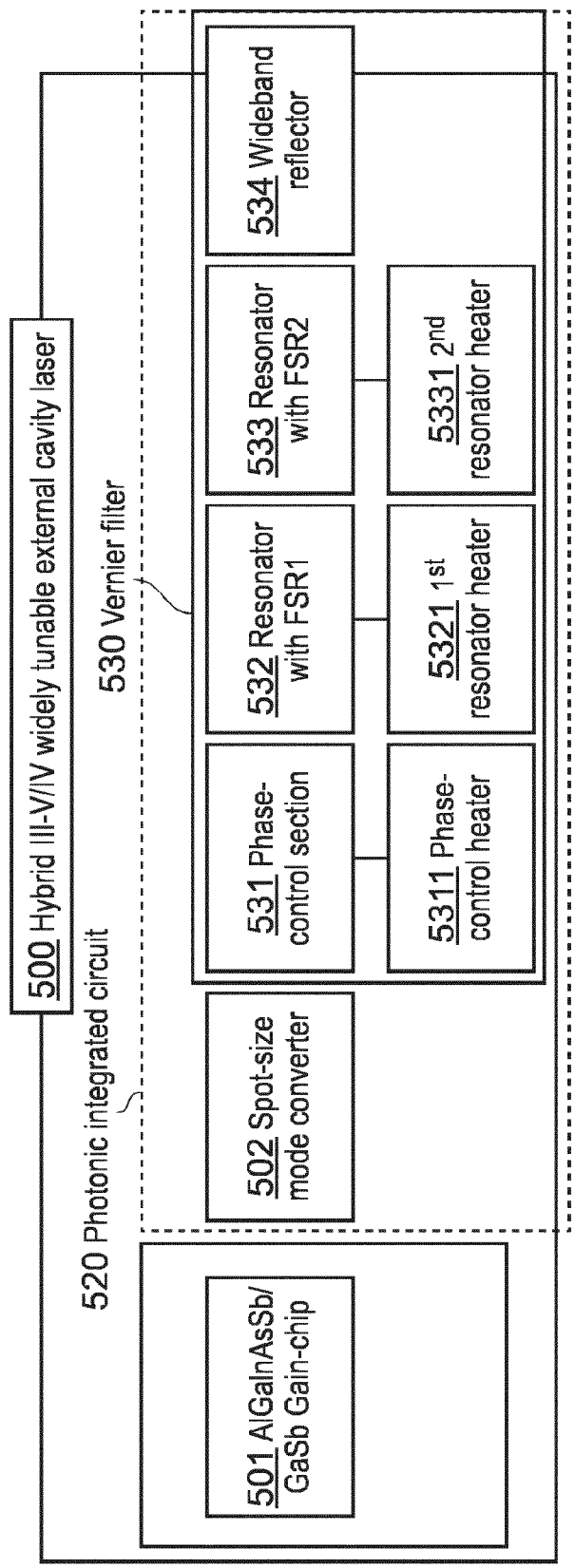
FIG. 5 is a detailed schematic block diagram of a III-V/IV widely tunable external cavity laser, in accordance with an embodiment of the invention.

As discussed with respect to FIG. 5, the widely tunable external cavity laser may include a III-V (AlGaInAsSb, AlGaInAsP, AlGaInAsSbP, AlGaInAsNSbP, etc.) gain-chip, spot-size mode converter, phase-shift section, coupled resonators with different free-spectral range values, a wide band reflector or reflectors and individual electro-thermal heaters for each of the resonators and phase shift section. For calibration-free operation, a laser signal emitted from the external cavity laser is passed through a beam-splitter.

Figure 6:
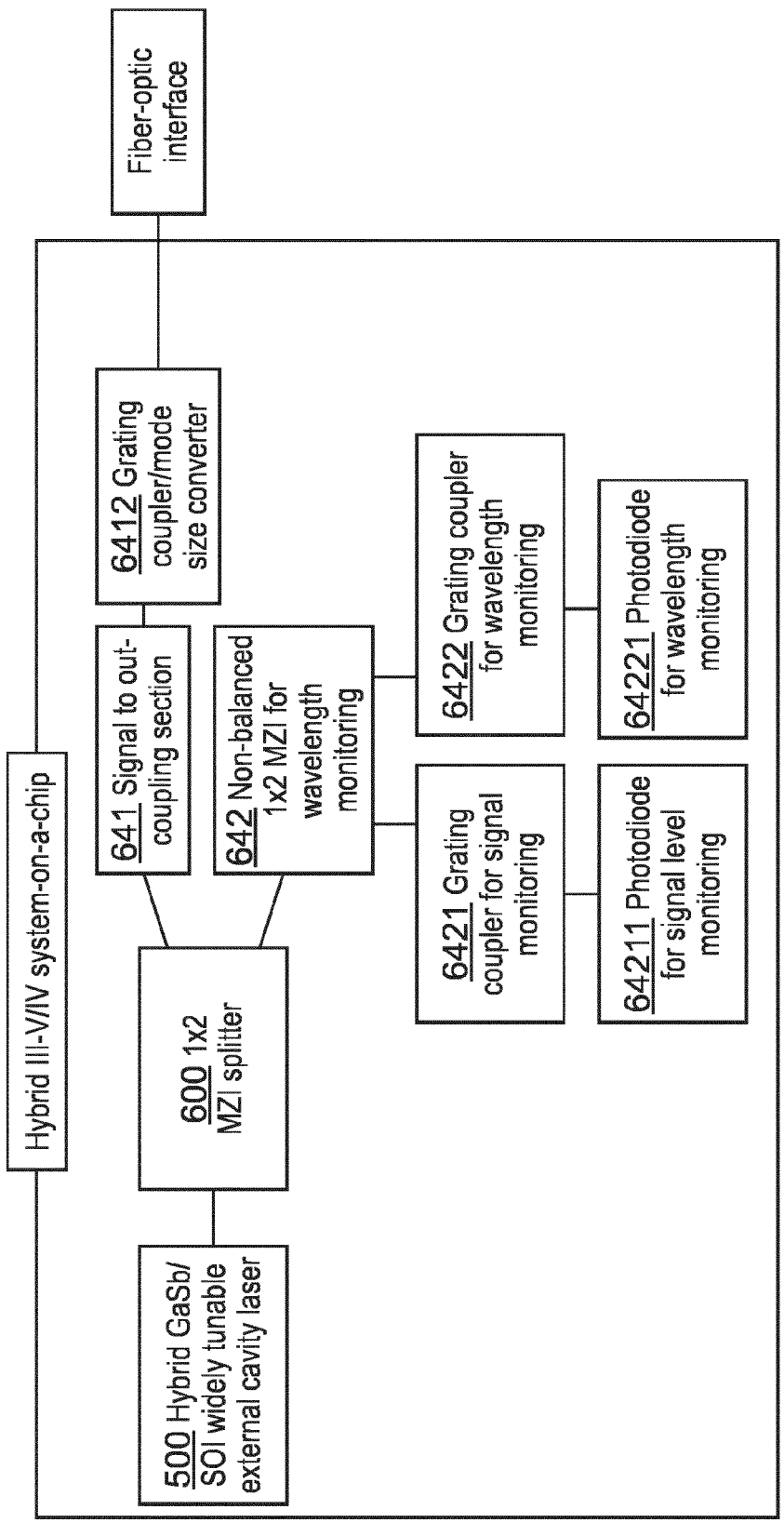
FIG. 6 is a detailed schematic block diagram of hybrid III-V/IV system on a chip, in accordance with an embodiment of the invention.

As shown in FIG. 6, an exemplary beam-splitter is a 1×2 Mach Zehnder interferometer (MZI), where one arm is coupled to either a surface grating coupler for surface out-coupling or spot-size mode converter and end-fire coupler (edge out-coupling) to couple to a fiber-optic interface, while the second arm of the MZI is used to pass the signal to a wavelength and signal control section realized by adding an additional filter in the form of for instance imbalanced 1×2 MZI with known optical path difference and with a photodiode at each of the arms to provide an oscillating transfer function which can be used to recover the emission wavelength and wavelength shift of the laser at any given moment of time thus providing calibration-free operation of the laser sensor.

Figure 7:
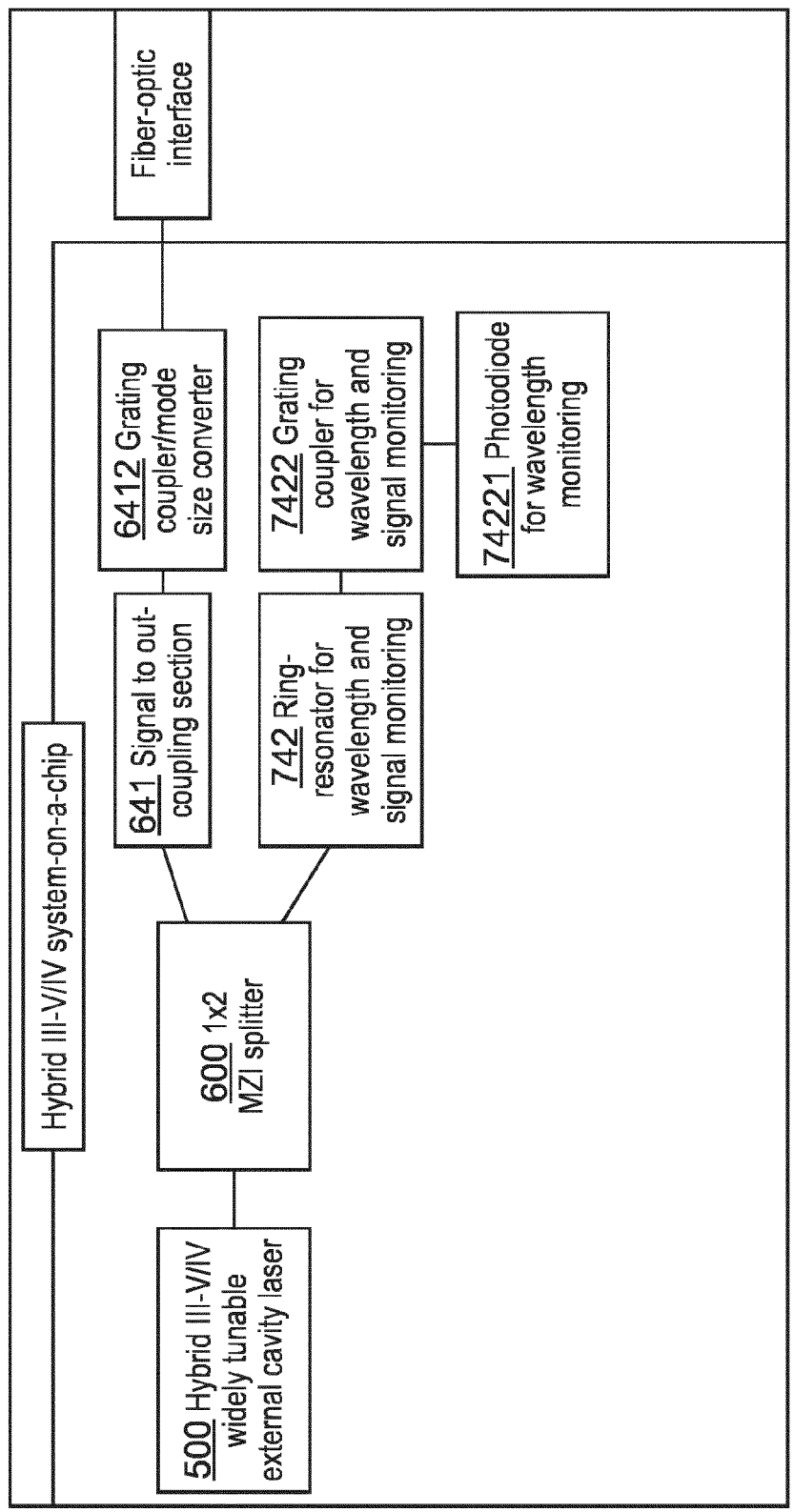
FIG. 7 is an alternative version of a detailed schematic block diagram of a hybrid III-V/IV system-on-a-chip, in accordance with an embodiment of the invention.

As discussed with respect to FIG. 7, similar wavelength control can also be realized by a single coupled ring resonator, whereby signal and wavelength control can be recovered by monitoring the filters' transmission function with a single photodiode.

In both embodiments of wavelength control, the system-on-a-chip is controlled by drive electronics, which in turn are controlled by a microprocessor that takes into account the data received from the wavelength control, and signal control and reflected signal photodiodes, and adjusts the drive parameters accordingly. This ensures that the laser wavelength sweep function is known and can be accounted for when processing the reflected light signal. The reflected light signal is processed using a developed algorithm that enables conversion of photodiode time signal into spectral domain to recover blood constituent concentration level data.

The fiber interface used for the sensor includes at least two separate cores, with one core (signal core) being used to transmit the laser signal from the sensor to the sample and the second core (collection core) being used to collect the reflected light from the sample and guide it to the photodiode at the sensor. Light can be coupled in and out of the system-on-a-chip by a surface grating coupler or an edge-coupled via end-fire configuration. In both cases the fiber core can be either multimode or single-mode.

Referring now to FIG. 1A, in an embodiment of the invention, a laser-based sensor includes a hybrid III-V/IV photonic system-on-a-chip (SoC) 10, which includes a widely tunable laser and a laser wavelength and amplitude monitoring section with flip-chip bonded, glued, transfer printed, or edge coupled integrated photodiodes. The sensor also includes an optical interface, such as a fiber-optic interface 20 for signal delivery via an optical communication link such as a fiber 12 and collection of reflected light via an optical communication link such as fiber 31, and a reflected signal (light) photodiode 40. Accordingly, the SoC includes at least one photodiode for wavelength/power monitoring, and another discrete photodiode for monitoring a signal reflected from blood. These components are described in greater detail below.

In addition to an optical interface, the sensor includes an electronic interface that is responsible for sensor control and signal processing. Generally, the sensor's control electronics include a central processing unit (CPU) 50, amplifier and analog-to-digital converter section 52, driver and digital-to-analog converter section 53, and a power supply electronics section 54 that supplies power for all electronic and photonic components. A suitable microcontroller for use with embodiments of the invention is an STM32F100 from STMicroelectronics, MSP430 from Texas Instruments, or other similar microcontrollers.

Since the CPU 50 is able to process only digital signals, whereas the SoC 10 and reflected signal photodiode 40 inherently provide analog signals, additional interfaces for converting digital signals to analog 53 and analog signals to digital 52 are needed. Based on the signal received from the SoC 10, via the electrical interface 51 that passes through the analog-to-digital converter section 52, the CPU 50 controls the drive signals of the SoC 10 via interface 15. Drive signals include gain-chip drive current, heater currents, photodiode bias, etc. The drive signals of the CPU pass through digital-to-analog converter section 53 that converts them to a form acceptable by the SoC and its elements. In addition, the CPU is in electrical communication with the power supply electronics section 54 via electrical interface 546 to set the necessary power supply values to remaining sensor elements via electrical interfaces 541, 542, 543, 544. Such a control scheme allows the CPU to precisely control the SoC and monitor the output signal in real-time. Thus, when the light signal out-coupled from the sensor interacts with the target molecule in blood is modified due to the interaction and is reflected back via fiber-optic interface 20 and guided to discrete reflected light photodiode 40, the collected signal is amplified and converted to digital form by the analog-to-digital interface 52 via electrical interface 41 and processed by a CPU to recover spectral and intensity information based on the comparison with the out-coupled signal. Signal processing includes conversion of time signal into wavelength/frequency domain and application of data processing algorithm specific to the target molecule. This allows the recovery and evaluation of the concentration level of the target molecule and provides as digital output via electrical interface 56 to an output display 60 that converts the signal to calibrated units such as mmol/l or g/l.

In the described embodiment, the photonic system-on-a-chip 10, reflected signal photodiode 40, and electronic components CPU 50, analog-to-digital interface 52, digital-to-analog interface 53, and power supply electronics section 54 are remote from a subject 30 and the interaction is by means of optical communication via the fiber-optic interface 20, which also includes a probe.

As used herein, a probe is a fiber optic device having at least two fiber cores, with one core suitable for use for the delivery of the laser signal to a sample and the other core suitable for detection of reflected light from the sample. In the case of an invasive measurement, the fiber optic interface needs to connect to an intravascular optical catheter that contains, among other probes, at least two optical fiber cores that connect to the SoC fiber interface in order to transfer and collect the sent and reflected laser signals. The two fiber cores of the probe terminate at the distal end which, in use, is in direct contact with blood. The terminated fiber core tips act as apertures through which the light is delivered to blood and collected thereafter. In the case of non-invasive measurement, the probe also has a distal end that, in use, is in direct contact to outer skin/tissue, with the fiber core apertures used to deliver and collect light through the outer tissue.

In use, the photonic system-on-a-chip 10 is driven and controlled by the embedded microprocessor CPU. The system-on-a chip 10 is instructed to send a swept wavelength laser signal to the fiber optic interface 20, with the laser signal consisting of a wavelength vs. time sweep. The laser signal is coupled to the fiber optic interface 20 that guides the signal to a target object device under test (DUT) 30, which in the illustrated embodiment is blood of a living body.

The laser signal interacts with the blood of the living body and is modified as a result of this interaction which provides characteristic features in the signal reflected from the blood. The reflected light signal is collected via fiber-optic interface 20, and is guided back to the reflected light (signal collection) photodiode 40. The photodiode 40 converts the optical signal into an electrical signal. The time domain signal is processed by the CPU, which takes into account the properties from the photonic SoC and the data analysis algorithm, and converts the photo diode signal into a calibrated concentration level in mmol/l (i.e., a blood constituent level), and provides as an analog or digital output via an electrical interface 56.

FIG. 1B shows an embodiment in which a probe is connected from the fiber-optic interface 20 to an optical intravascular catheter or invasive probe 22, which is in physical contact with the target object 30. The catheter 22 is configured to (i) transmit a light signal from the sensor to blood of the subject and (ii) transmit reflected light from the blood of the subject to the sensor.

FIG. 1C shows an embodiment in which the optical interface, consisting of the light delivery and light collection cores and additional optics, e.g., beam shaping optics, is configured to non-invasively illuminate a blood sample 30 of the subject through the subject's skin or outer tissue 23. One may preferably put the non-invasive probe at a location where the outer tissue has a relatively small thickness such as fingertip, fingernail bed, wrist, etc.

Figure 2:
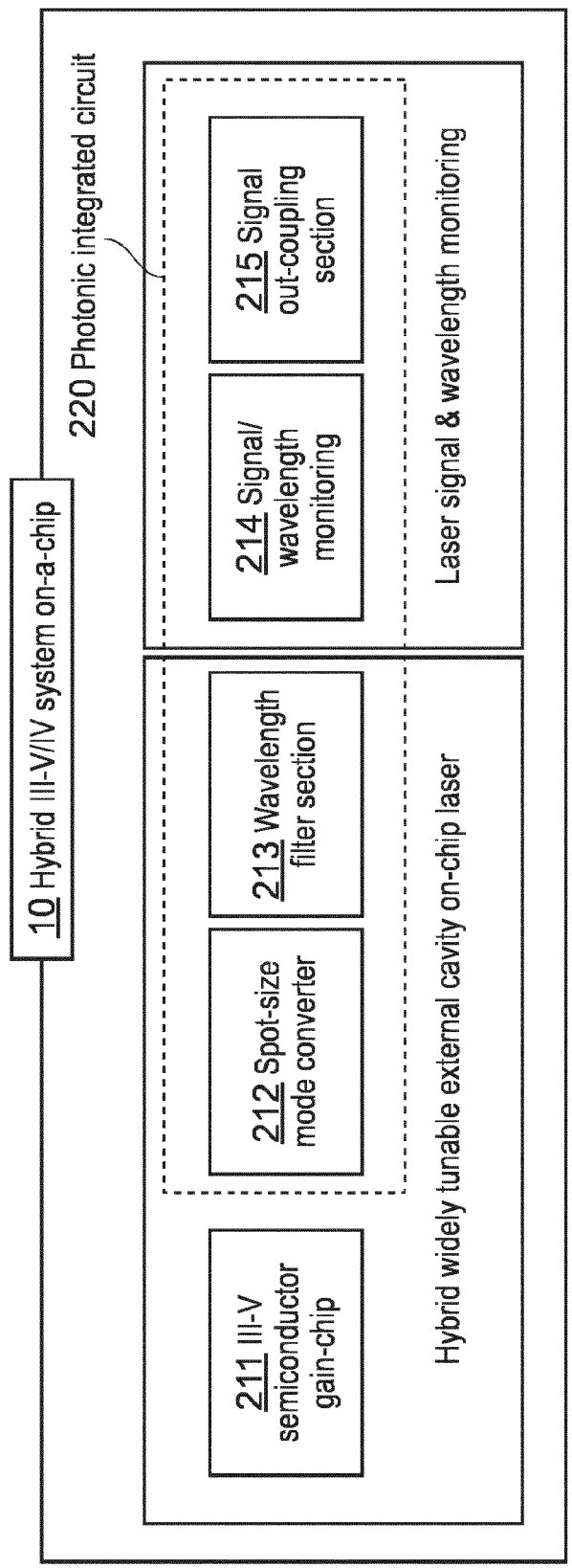
FIG. 2 is a schematic diagram of a hybrid III-V/IV system-on-a-chip, including a hybrid widely tunable external cavity laser and laser signal and wavelength monitoring sections, in accordance with embodiments of the invention.

Referring to FIG. 2, the photonic system-on-a-chip 10 includes a III-V (e.g., AlGaInAsSb/GaSb or AlGaInAsP/InP or AlGaInAs/GaAs) semiconductor gain-chip 211 that provides optical gain to the system. The gain-chip 211 is coupled to a passive photonic integrated circuit realized in a group IV semiconductor chip, in the particular case silicon-on-insulator is chosen. A typical photonic circuit 220 includes a spot-size converter 212 that increases the efficiency of light coupling between the chips. The typical photonic circuit also includes a wavelength filtering section 213 that forms a hybrid III-V/IV external cavity laser when combined with the III-V gain-chip 211. The photonic integrated circuit 220 also includes a signal/wavelength monitoring section 214 and a signal outcoupling section 215, discussed in more detail with respect to FIGS. 6 and 7 below.

The wavelength filtering section 213 is preferably realized by coupled resonators and wideband reflector forming a Vernier filter. The coupled resonators have different free-spectral range values, which when coupled, lead to a wide accessible bandwidth. For example, a coupled resonator cavity may be formed from two micro ring resonators: a first ring with a ring radius of 27.5 microns and the second ring resonator with radius of 28.5 microns. For a GaSb material system at an operating wavelength of 2300 nm, the effective modal refractive index is 3.59. This leads to a free-spectral range of the first ring resonator being 4.26 nm and a free-spectral range of the second ring resonator of 4.11 nm. When coupled, the Vernier filter has a tuning bandwidth of 117 nm. These values may be calculated by use of the following equations.

In case of a ring resonator, the mode spacing can be defined as:

$$FSR = \frac{\lambda^2}{4\pi nR}$$

where $\lambda$ is the center wavelength, n is the modal effective refractive index and R is the ring radius.

The overall tuning bandwidth can be estimated by $$\Delta\lambda = \left| \frac{FSR1 \cdot FSR2}{FSR1 - FSR2} \right|$$

The tunable bandwidth can be adjusted by design in the form of different free-spectral range offset and coupling coefficient. Such a bandwidth is sufficient to be coupled to a broadband III-V gain-chip to cover the necessary spectral range for blood metabolite concentration level monitoring.

Figure 3A:
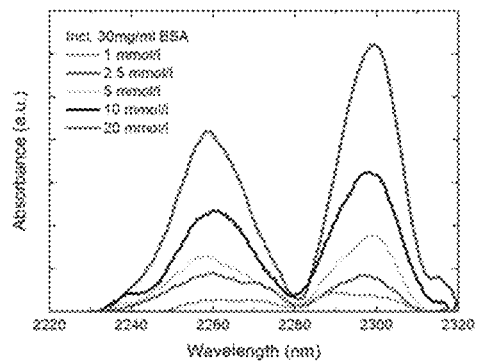
FIG. 3A is an experimentally obtained characteristic absorption spectrum of different lactate molecule concentration in a BSA-containing solution to simulate blood environment, with the spectrum after baseline correction, in accordance with an embodiment of the invention.
Figure 3B:
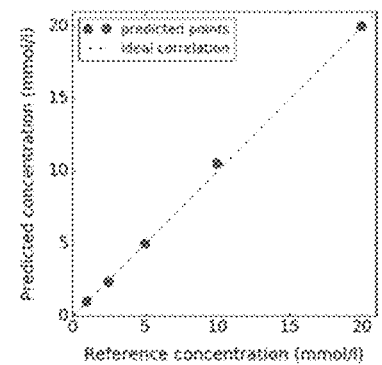
FIG. 3B is a graph showing the correlation between predicted and real lactate molecule concentration, with predictions obtained using multivariate PLS.

A lactate molecule is a good example of a target molecule both in terms of application significance as well as a well-expressed optical signature in the infrared range. FIG. 3A illustrates an experimental absorption spectrum of a lactate molecule. It can be clearly seen that due to the liquid phase of the target, the spectrum is broad and features two distinct absorption peaks, centered at 2260 nm and 2300 nm. For concentration level calculation, it is beneficial to have the shape of the absorption signal. Also, as can be seen from the same figure, in the case of a lactate molecule, the accessible optical bandwidth needed is about 100 nm. An experimental concentration calibration curve for different concentration levels is shown in FIG. 3B.

Besides the passive circuitry optical response, it is necessary that the optically active part be capable of covering the needed bandwidth. A typical wavelength tuning spectrum of a mid-infrared broadband gain-chip, realized, for example, in an AlGaInAsSb/GaSb material platform can have an optical gain-bandwidth in excess of 170 nm, as shown in FIG. 4. Each of the spectra 400, 410, 420, 430, 440 was generated by a different III-V gain-chip embedded in an external cavity configuration. The spectral position of the gain-chip emission can be tuned by chip design by changing the layer thicknesses and compositions to match the necessary spectral response of the target molecule and the optical response of the photonic integrated circuitry on the group-IV semiconductor chip, using methods known to one of skill in the art. FIG. 4 clearly demonstrates the flexibility of III-V chip design in the entire 1700 nm-2500 nm range without trade-off in performance.

Referring to FIG. 5, a hybrid III-V/IV widely tunable external cavity laser 500 includes a III-V, in this particular case, AlGaInAsSb/GaSb gain-chip 501 that may serve as an active optical medium and may be edge-coupled to a silicon photonics integrated circuit 520 via the spot size converter 502 that converts the mode emitted from the gain-chip and matches it to a size suitable for the group-IV semiconductor based waveguide used in the photonics integrated circuit. Wavelength tuning is realized by means of Vernier-effect filter 530, where fine tuning is controlled with a phase control section 531 that may include a straight or folded waveguide section with a separate electro-thermal heater 5311. The wide tuning is controlled by the coupled-resonator cavity, where a first resonator 532 with a free-spectral range of FSR1 is coupled to a second resonator 533 with a free-spectral range FSR2, where FSR1 and FSR2 are non-equal. The effective modal refractive index of each of the resonators is controlled individually via electro-thermal heaters 5321 and 5331. The laser resonator cavity is completed with a wideband reflector 534 that is designed to be broad enough for the required tuning range. Typically the reflector has a reflectivity bandwidth in excess of 50 nm or more. The reflector may be realized by, e.g., a distributed Bragg reflector or a folded Mach-Zehnder interferometer (MZI) or any other typical broadband reflector—such as metal mirror. For a typical operation performed by the sensor, the gain-chip drive current is fixed, and the wavelength sweep is performed by a controlled sweep of the heater 5311, 5321, 5331 currents.

Vernier wavelength filtering technique is well known in the field of optical communications and is not limited to micro-ring resonators but can also be realized by coupled resonators defined by sampled grating distributed Bragg reflectors or sampled grating distributed feedback reflectors. The final choice depends on the designer's preferences and geometrical considerations of the chip layout. In all cases of coupled resonators, the wavelength of operation is defined by the overlap of the two wavelength combs. The overlap position is changed by changing the refractive index of one or both coupled resonators simultaneously. In practice, this is achieved either by direct current injection or thermal heating causing a change of refractive index and thus emission wavelength. In the described example, a change in wavelength is controlled by deposited resistive heaters above each micro-ring resonator. Wideband reflector can be realized in the form of distributed Bragg grating, a folded balanced Mach-Zehnder interferometer or a similar high-Q reflector. Preferably, the tuning band of the system is defined by the bandwidth of either the Vernier filter or the wideband reflector, depending on which of the two is smaller.

Referring to FIGS. 6 and 7 as well as to FIG. 2, wavelength and laser power monitoring of the external cavity laser formed by the gain-chip 211 and the wavelength filter 213 can be realized in the form of a non-balanced Mach-Zehnder interferometer with each output coupled to a separate grating coupler with an integrated photodiode (flip-chip, glued, etc.) or a single-ring resonator coupled to a grating coupler with an integrated photodiode. This is called a signal/wavelength monitoring section 214. Both the non-balanced MZI and a single ring resonator have a very well defined wavelength dependent transmission function, which can be characterized and calibrated to provide an exact value of emission wavelength and output power at any given moment of time, presuming the drive signals are known. This is advantageous, as both signal power and signal wavelength can be tracked via a single photodiode with high accuracy. Thus the described combination of a hybrid system-on-a-chip includes not only a widely tunable laser but also a monitoring wavelength meter and power meter within the same chip.

Referring to FIG. 6, more specifically, the hybrid III-V/IV widely tunable external cavity laser 500 described in FIG. 5 is coupled to a 1×2 Mach-Zehnder interferometer (MZI) splitter 600, where one arm is used to out-couple the laser signal to the system-on-a-chip out-coupling section 641 either via top grating coupler or mode-size converter and end-fire out-coupler 6412 which further out-couples light to the fiber-optic interface. The second arm of the 1×2 MZI splitter 600 is connected to a second 1×2 MZI 642, which is non-balanced. One arm of the interferometer is connected to a grating coupler 6421 which guides the light into a flip-chip bonded photodiode 64211 for laser signal monitoring. The second arm of the interferometer is guided to a second grating coupler 6422, which couples light into a second photodiode 64221, which monitors the MZI 642 transfer function for precise wavelength tracking.

The drive signals for the gain-chip, individual heater tuning, and phase shift tuning are controlled by the CPU 5, which uses the information from the signal/wavelength monitoring section photodiodes to determine the necessary driving signal form and amplitude. A typical SoC may require that at least five different control currents be accounted for to generate a continuously tunable wavelength laser pulse. In the described embodiment, a CPU provides a drive signal sweep that consists of a certain sweep of individual drive currents for the SoC, to provide a continuous wavelength sweep as a function of time at the sensor output. Since the CPU is in electrical communication with SoC signal and wavelength monitoring section photodiodes 64211 and 64221 at all times, generally any arbitrary drive signal results in SoC output that can be recovered in terms of amplitude and wavelength at all times. In a real case scenario, the CPU may be programmed to provide the simplest possible signal output—for example as close to a linear wavelength sweep as a function of time as possible—to enable simple data processing based on the recovered signal from a discrete photodiode 40. Knowledge of the laser signal amplitude and wavelength within the sent light pulse allows simple reconstruction from time to frequency domain of the collected signal from the blood and elimination of the nonlinearity and signal variation due to the sensor itself, in such way allowing direct access to the perturbation of the optical signal due to interaction with the target molecule.

Referring to FIG. 7, in another embodiment, the hybrid III-V/IV widely tunable external cavity laser 500 described in FIG. 5 is coupled to a 1×2 Mach-Zehnder interferometer (MZI) splitter 600, where one arm is used to out-couple the laser signal to the system-on-a-chip out-coupling section 641 either via top grating coupler or mode-size converter and end-fire out-coupler 6412 which further out-couples light to the fiber-optic interface. The second arm of the 1×2 MZI splitter 600 is coupled to a ring-resonator 742, which provides a characteristic wavelength transfer function for the light that passes through. After the filter the light is guided to a grating coupler 7422 which couples light to a flip-chip photodiode 74221 which monitors the signal transfer function. The transfer function can be used to determine the wavelength of the light and relative intensity of the laser at the same time, with only one control photodiode, rather than multiple photodiodes as, for example, illustrated in FIG. 6.

In the described embodiments, a hybrid integration of III-V semiconductor chip and group-IV semiconductor chip technology is considered. The gain-chip is realized in a III-V material system such as AlGaInAsSb/GaSb, AlGaInAs/GaAs or AlGaInAsP/InP or a combination thereof, in the form of an edge emitting device such as ridge waveguide edge emitter. The light is generated by electrical injection of carriers into the undoped quantum wells where they recombine emitting photons. The optical gain for such a structure is spectrally broad and typically can span from few 10s of nm to 200 nm or more depending on the photon energy ant the epitaxial design. The spectral region can be defined by choosing appropriate layer alloy compositions and thicknesses, as is well known by those skilled in the art of semiconductor optoelectronics.

Figure 8:
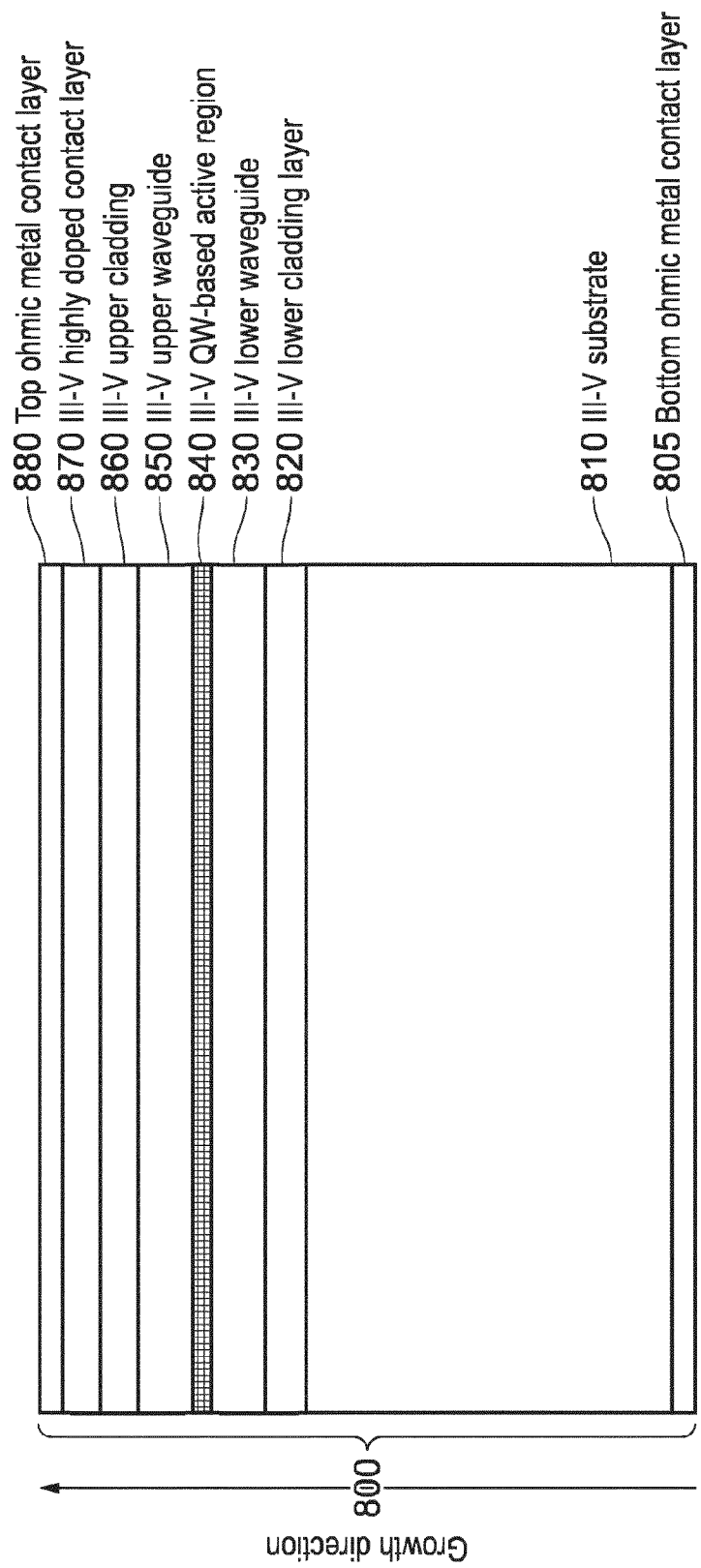
FIG. 8 is a schematic cross section of a III-V gain-chip functional layer structure, in accordance with an embodiment of the invention.

A typical schematic cross-section of a III-V gain-chip 800 is shown in FIG. 8. A III-V gain-chip is epitaxially grown on a III-V substrate 810 that, depending on the desired wavelength of operation, can be GaAs, InP, GaSb, or InAs. On top of the substrate, the remaining structural layers are grown, i.e., a lower cladding layer 820, lower waveguide layer 830, quantum-well based active region 840, followed by a more or less symmetric upper waveguide layer 850, and upper cladding layer 860. The layers may be grown epitaxially, e.g., by molecular beam epitaxy (MBE) or metalorganic vapor phase epitaxy (MOVPE). The structure is finalized by a highly doped contact layer 870 that forms an ohmic contact with the top metal contact layer 880. The bottom contact layer is formed by a metal layer deposited on the bottom of the substrate 805. The emission wavelength is defined by the composition of layer 840. The structural layers 820, 830, 850 and 860 are chosen to provide symmetrical waveguiding and good optical mode overlap with the active region layer 840. Typically, the active region is composed of at least one quantum well to provide sufficient gain.

To form the gain-chip, the epitaxial structure is processed into a ridge-waveguide edge-emitting device, in which mode is guided by a defined ridge waveguide formed by plasma or wet-etching. The height and width of the ridge depends on the individual design, an important feature being that the waveguide is single mode. The design of single mode waveguides is a common procedure and is known to those skilled in the art. The cavity of the gain-chip may be realized by cleaving the processed wafer into bars, consisting of a linear array of edge-emitting gain-chips, with the cleaved crystal facet forming a cavity mirror, as is common in making edge emitting devices such as semiconductor lasers. The optical emission is from the edge of the chip, i.e., perpendicular to the growth direction.

For optimal performance in external cavity laser configuration, the back facet may be coated with a high-reflectivity mirror coating, with a typical mirror reflectivity of at least >90%, e.g., >95%. The front facet, i.e., the output facet, of the chip is preferably coated with very low reflectivity coating, with typical reflectivity of <0.1%, to avoid optical feedback from the front facet plane. Optical feedback may be further reduced by using a bent waveguide design in which the ridge of the gain-chip has a predetermined bending radius to reduce reflection. Due to the bending of the ridge, the out-coupled light is refracted and emission is at a fixed angle in terms of the output plane. This predefined waveguide angle is known from the design and modal effective refractive index, and needs to be taken into account when designing the passive photonic circuitry on the group-IV semiconductor platform. In particular, the spot-size converter is preferably designed to match the angle of the gain-chip emission and the size of the outcoupled mode to reduce coupling loss between the two chips.

For best design practice, the main properties such as mode size and shape, emission wavelength, gain-bandwidth, emission angle, divergence, etc. of the III-V gain-chip are known experimentally and are used to adapt and customize the passive photonic integrated circuit on group-IV semiconductor. In particular, knowing the experimental parameters of the gain-chip allows optimizing main SoC elements such as spot-size converters, coupled resonator cavities, wide band reflectors, multimode interference devices (MMI), interferometers, and other functional elements.

Typically, facet coating is performed on gain-chip bars, and individual gain-chips are separated by scribing and breaking after the facet coating procedure. This can be done in many ways, with the most common being forming a mechanical scribe line along the crystal plane perpendicular to the chip cleaved facets and applying mechanical breaking force from the top or bottom to enable crystal cleavage along the defined line. Individual gain-chips can then be readily integrated with the group-IV circuitry.

A group IV-based semiconductor platform is typical for most common electronic device technologies such as CMOS. Hybrid integration of III-V optical components with a group IV semiconductor platforms opens opportunities for scaling technology in the same manner as CMOS technology is scaled. Group IV semiconductor platforms include silicon, silicon-on-insulator (SOI), germanium-on-insulator (GOI), germanium on silicon, silicon nitride on silicon, silicon nitride-on-insulator, silicon nitride-on-silicon-on-insulator, and their derivatives.

Figure 9:
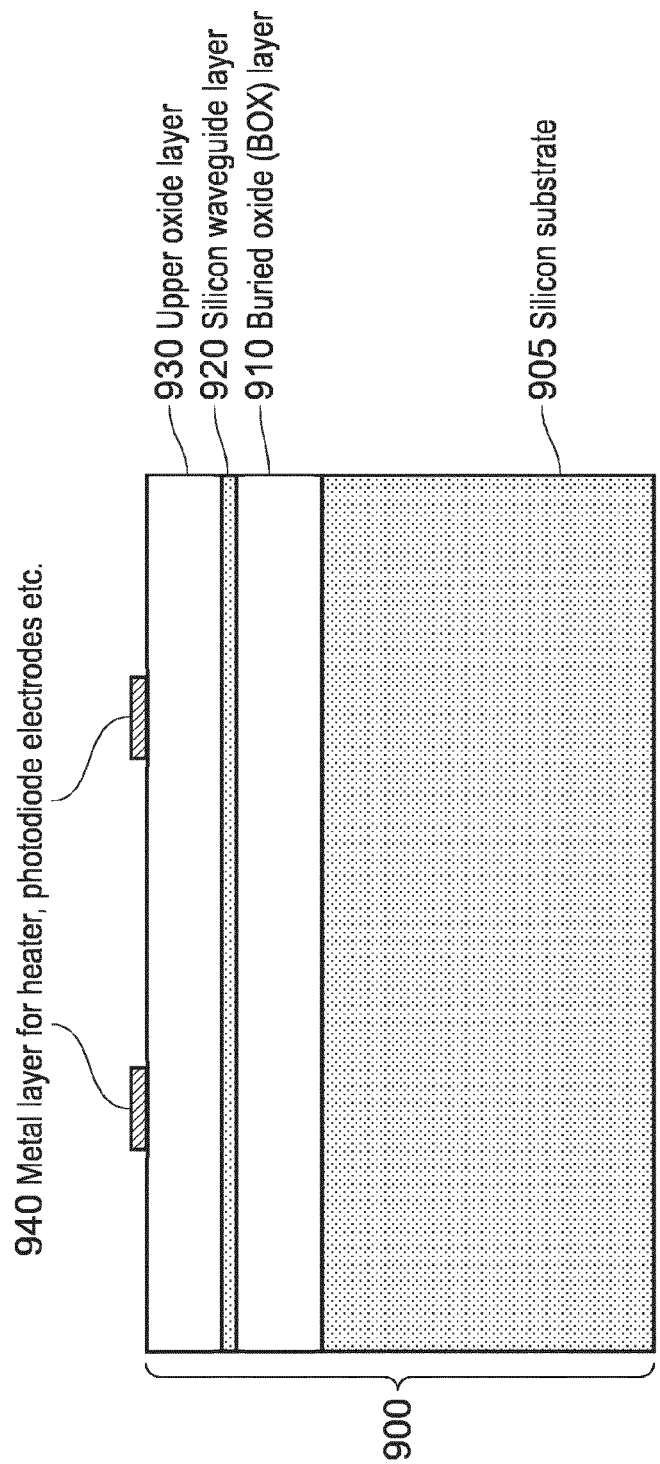
FIG. 9 is a schematic cross section of an exemplary group IV semiconductor chip having a silicon-on-insulator functional layer structure, in accordance with an embodiment of the invention.

A typical silicon, in particular a silicon-on-insulator (SOI) chip cross-section is shown in FIG. 9. In the illustrated embodiment, the SOI chip 900 is simpler than the gain-chip and includes a IV-based semiconductor substrate 905, e.g., a silicon substrate with a buried oxide layer (called BOX) 910 which can be of different thicknesses depending on the fabrication facility, with typical thicknesses being 2-3 microns. The BOX layer is formed by, for example, ion implantation and wafer bonding, as is well known to one of skill in the art. The BOX layer 910 is followed by a silicon waveguide layer 920. This layer serves as a functional layer where all passive photonic components are realized, such as grating coupler, single-mode and multimode waveguides, ring resonators, multimode interference devices, spot-size converter, etc. The layer thickness may vary depending on the fabrication facility, and is typically 100 nm-500 nm thick; in some fabrication facilities it can be as thick as several microns. A typical silicon photonics platform includes a 220 nm waveguide layer 920. The waveguide layer 920 is further capped with a silicon oxide layer 930 that can be thermally grown or deposited by other techniques. Depending on the group-IV platform used, other insulating materials can be used, for example silicon nitride. The main purpose of the BOX layer 910 is to prevent optical mode coupling from the waveguide layer 920 into the substrate 905 and to serve as a low refractive index cladding layer in the same manner as the top silicon oxide layer 930. The refractive index change of the silicon waveguide layer 920 can be achieved by thermal signal via the resistive electrical heaters in the form of metal electrodes 940 deposited on top of the upper oxide layer. In addition to heaters, the metal electrodes can also serve as flip-chip photodiodes that collect the signal out-coupled from the grating couplers.

Figure 10:
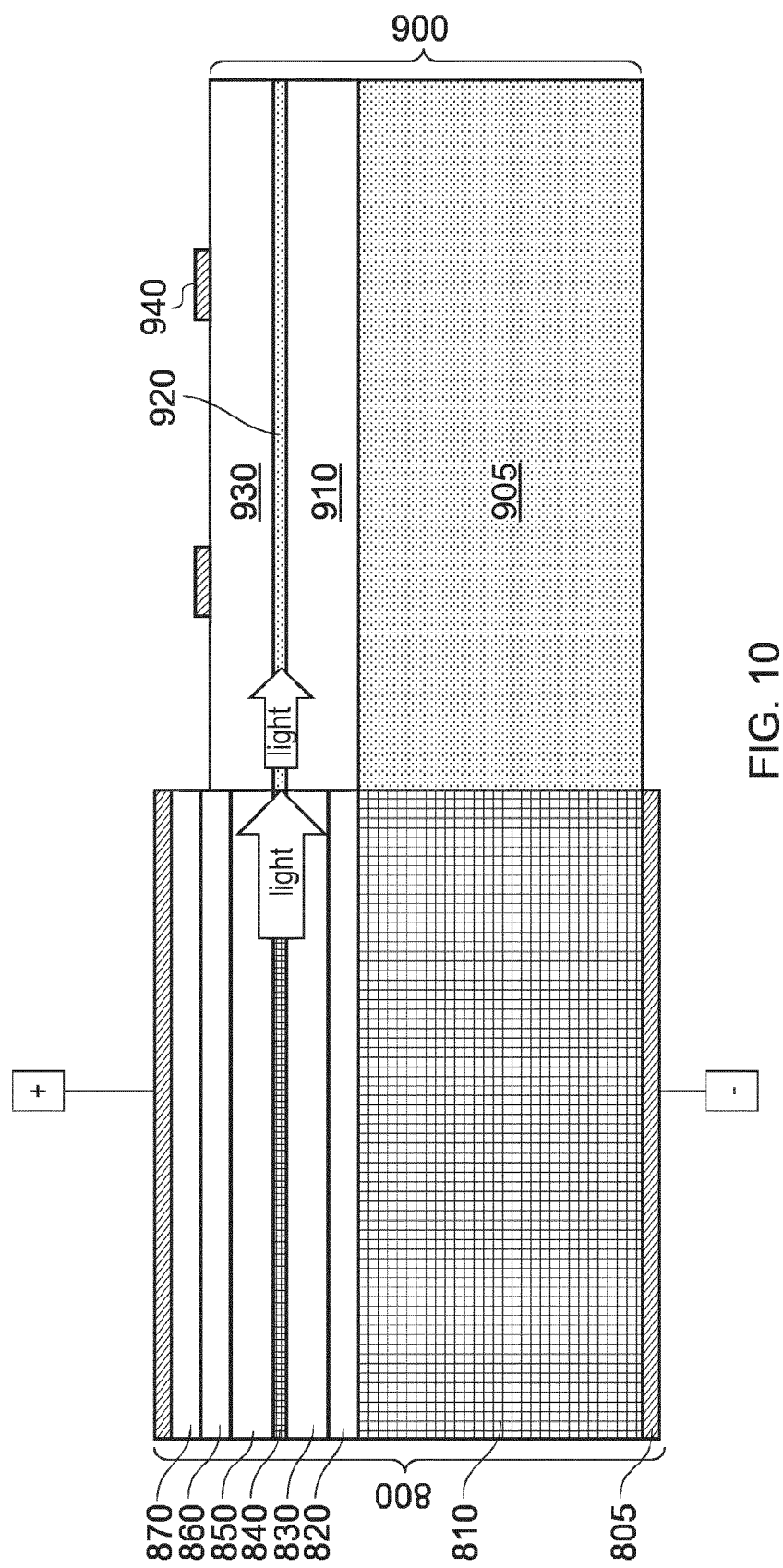
FIG. 10 is a schematic representation of hybrid integration of a III-V gain-chip to a group IV semiconductor-based photonic integrated circuit, in accordance with an embodiment of the invention.

A schematic principle of hybrid integration is shown in FIG. 10. Here the III-V gain-chip 800 and the group IV semiconductor, in the particular example silicon-on-insulator chip 900 are integrated by edge-coupling, with the III-V gain-chip being p-side up and edge coupled to the group IV chip. The light generated in the active region layer 840 of the gain-chip is coupled to a silicon waveguide layer 920 where passive photonic integrated circuitry is realized. One of the critical requirements for the integration is efficient coupling of light between the two chips. This can be achieved by using active alignment technique, i.e., with the III-V gain-chip emitting light during the alignment process and the coupling efficiency monitored via a grating coupler on the group IV chip. Once the signal is maximized, the two chips are bonded together by curable glue or epoxy.

Figure 11:
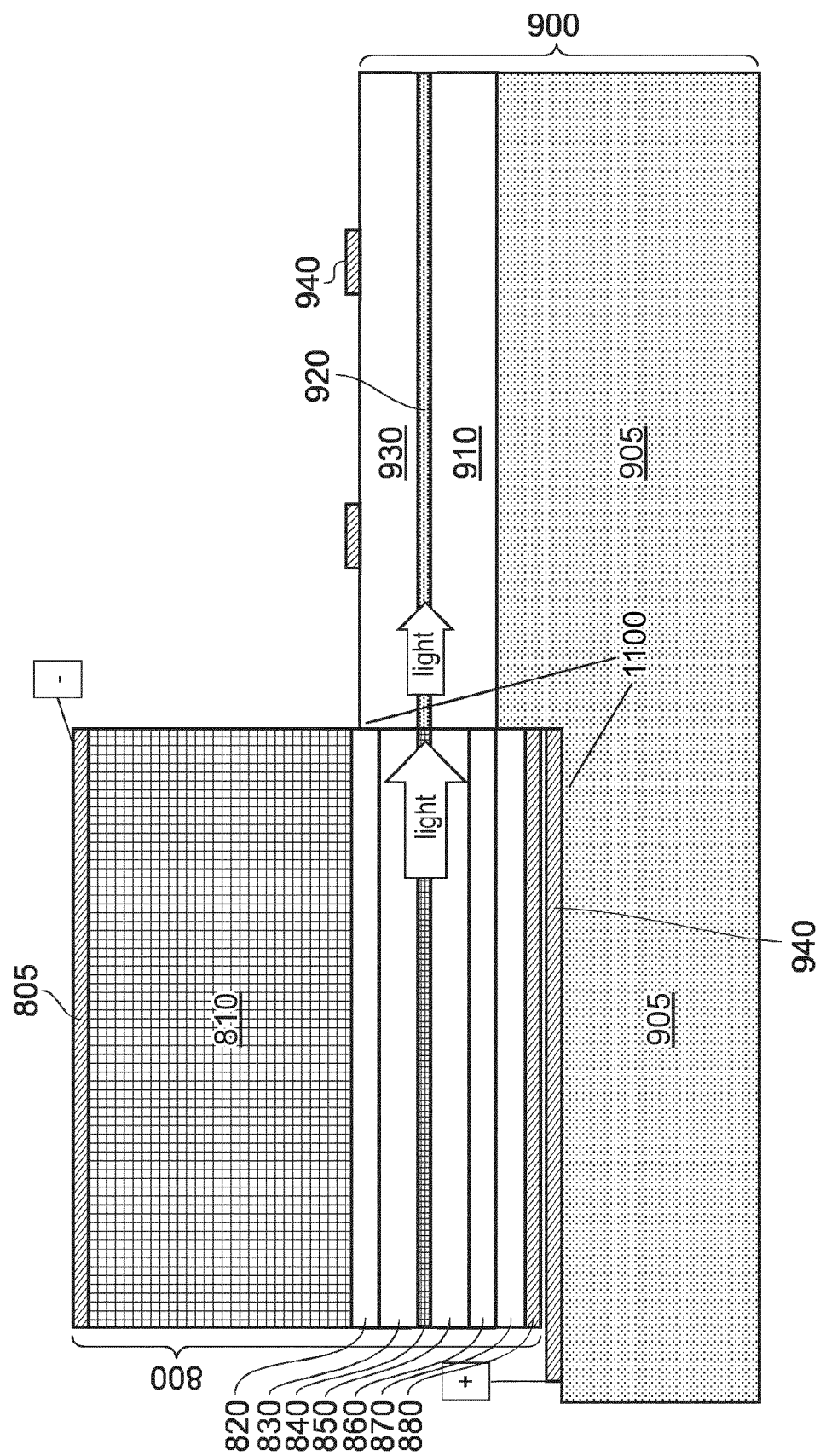
FIG. 11 is a schematic representation of hybrid integration of the III-V gain-chip to the group IV semiconductor-based photonic integrated circuit, in accordance with an embodiment of the invention.

A higher accuracy can be achieved when the position of the III-V gain-chip is predefined on the group-IV semiconductor wafer. This can be realized by a deep trench as shown in FIG. 11. The trench 1100 not only defines the approximate position but at the same time can exactly match the height of the two chips in the vertical direction. For maximum accuracy the III-V gain-chip needs to be flipped so that the height of the III-V chip is defined by the epitaxial layer thickness, which is extremely accurately controlled. The in-plane position needs to be aligned via active alignment for best accuracy. The chips are fixed together by means of glue, epoxy or metal solder such as indium or AuSn at the interface between top metal contact layer 880 and metal electrode layer 940. The illustrated III-V gain-chip is flipped to a p-side down position, and edge coupling is realized via the pre-defined trench in the group IV wafer that enables light coupling to the passive photonic circuitry.

Figure 12:
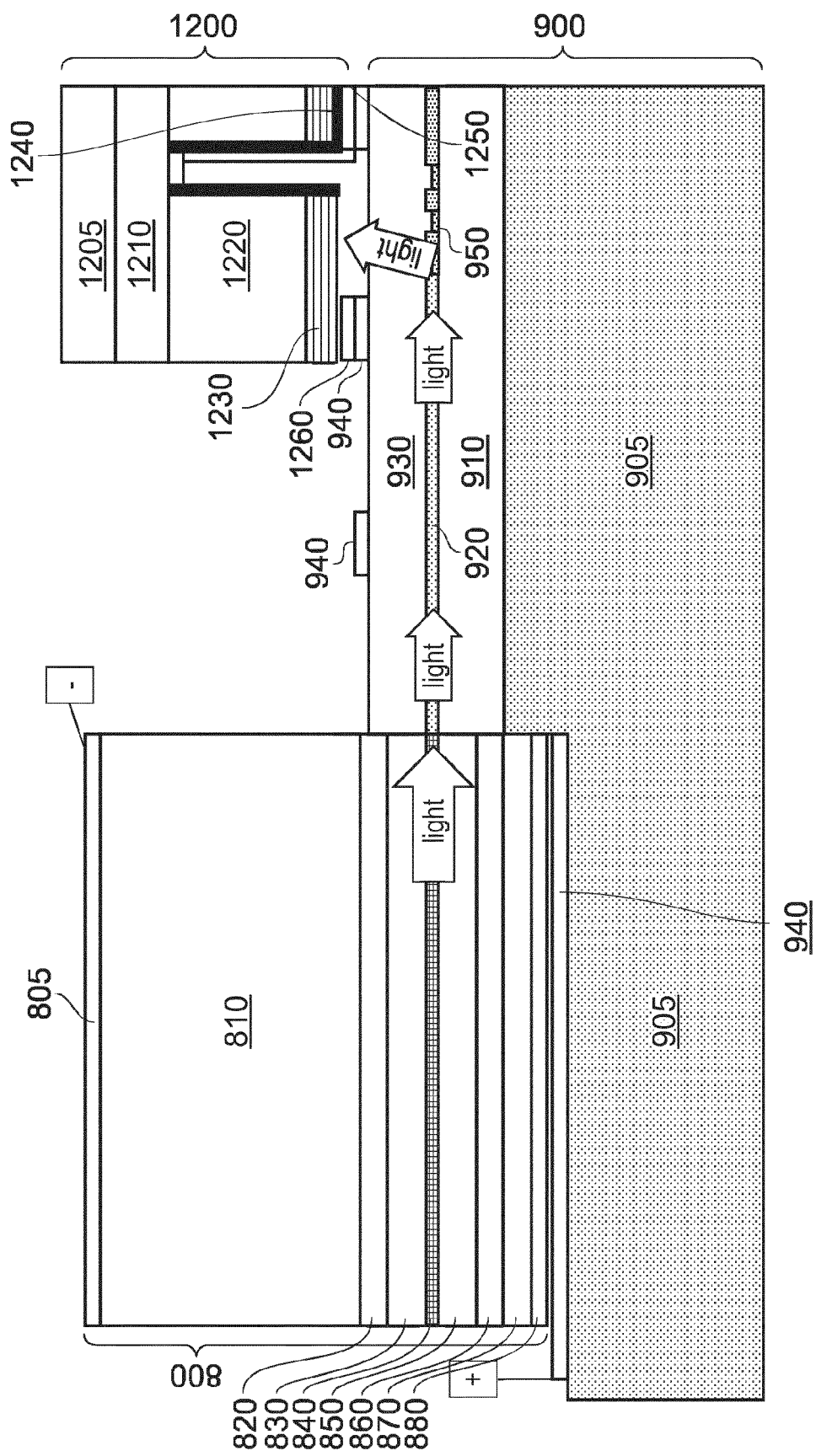
FIG. 12 is a schematic representation of hybrid integration of the III-V gain-chip to the group IV semiconductor-based photonic integrated circuit, in accordance with an embodiment of the invention.

A complete hybrid system including a III-V gain-chip, group IV semiconductor chip, and flip-chip photodiode is shown in FIG. 12, demonstrating how light can be coupled into the group IV semiconductor chip and coupled out of the group-IV semiconductor chip. The III-V gain-chip is flipped to p-side down position and edge coupling is realized via a pre-defined trench in the group IV semiconductor wafer to enable light coupling to the passive photonic circuitry. A flip-chip photodiode structure is also shown, used to collect optical signals via a surface grating coupler.

In particular, coupling out is achieved via a flip-chip photodiode on top of a grating coupler 950. The photodiode can be formed from any relevant semiconductor material that has a needed photo response at the wavelength of interest. In this embodiment, a typical photodiode is a III-V p-i-n photodiode designed from the same material platform as the III-V gain-chip. The photodiode 1200 is formed on a III-V substrate 1205, followed by a doped layer 1210 that is either n or p-type, undoped absorption layer 1220 having an undoped material composition such that it absorbs the light coupled out of the group IV semiconductor chip. The absorption layer thickness is optimized for different wavelengths, with a typical thickness of 2 microns and a typical minimum thickness of at least 500 nm. The absorption layer is followed by a doped layer 1230 that can be either p- or n-type but needs to have a dopant polarity opposite to that of layer 1210 in order to form a pn-junction. The anode and cathode are preferably realized on the same side of the chip to facilitate flip-chip process. In the exemplary figure, the doped layer 1210 is biased by etching a trench and depositing a metal layer 1250 to form a metallic ohmic contact. Suitable metals include titanium, platinum, gold, nickel, chromium, and gold-germanium and/or combinations thereof, as is well-known to those skilled in the art. The metal layer 1250 is in contact with the doped layer 1210 only at the bottom of the trench. Other photodiode layers are separated from the metal layer by a dielectric isolator 1240. The second contact is formed on top of the photodiode diode mesa and is to have an ohmic like contact between the top metal pad 1260 and the top contact semiconductor doped layer 1230. The photodiode is coupled to the photonic integrated circuit with flip-chip technology as follows. The photodiode is flipped aperture facing down and overlapping with a portion of the surface grating coupler formed on the group IV semiconductor chip. The photodiode is aligned for maximum signal collection coming out from the grating coupler and bonded in place by means of indium, AuSn or other standard soldering techniques.

Figure 13:
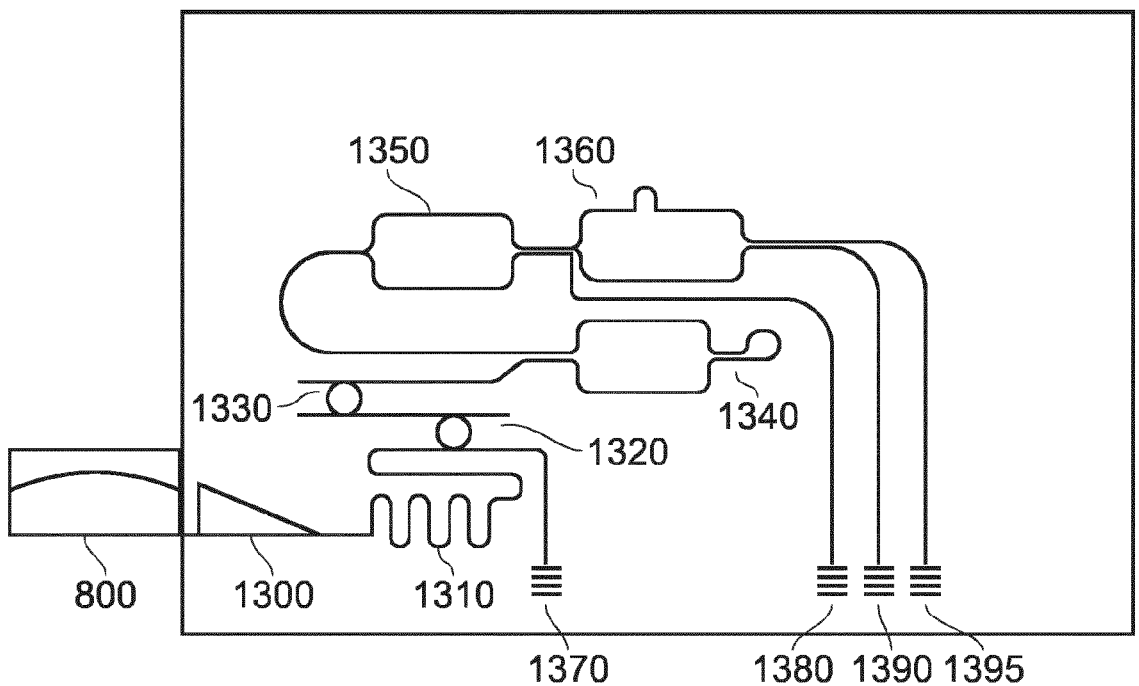
FIG. 13 is a schematic representation of a top view of system on-a-chip photonic circuitry, in accordance with an embodiment of the invention.
Figure 14:
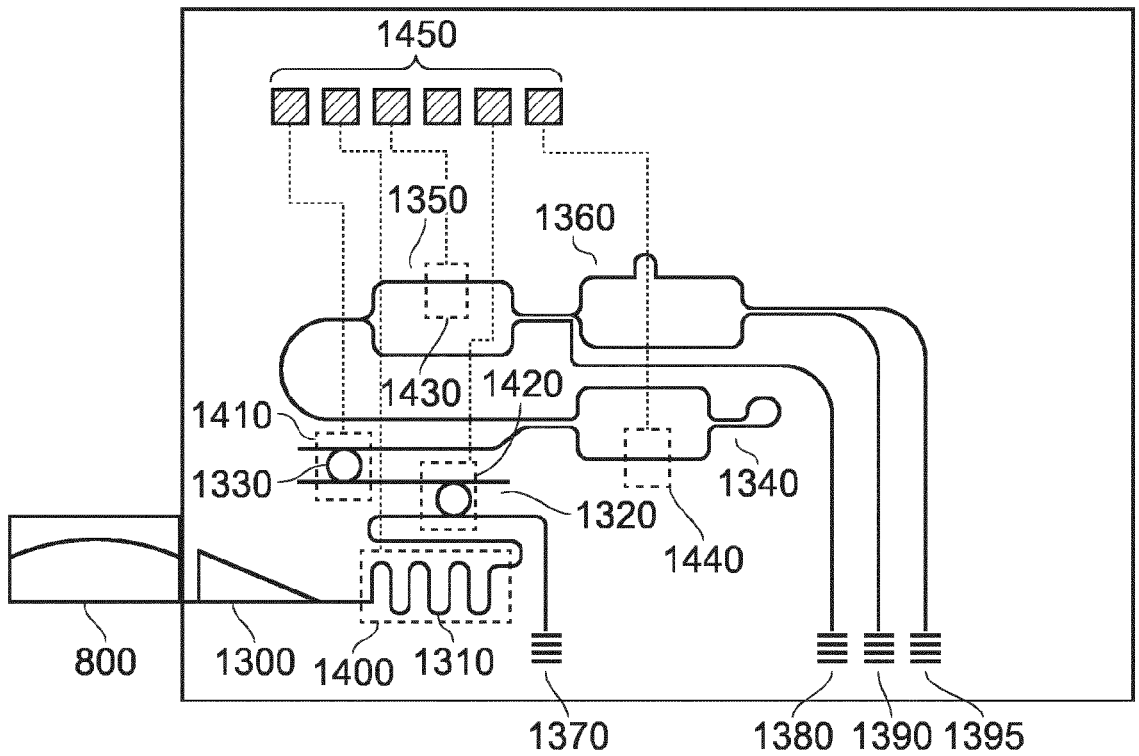
FIG. 14 is a schematic representation of the layout of FIG. 13, with additional features, in accordance with an embodiment of the invention.

Top views of the schematic hybrid system-on-a-chip based on edge-coupling are shown in FIGS. 13 and 14. A III-V gain-chip 800 is edge coupled to a group IV semiconductor chip via spot-size converter 1300 that converts the mode size from the III-V waveguide to the silicon waveguide with minimal optical loss. The spot size converter is coupled to a phase shift section 1310 consisting of a straight or folded waveguide and an electrical heater. This section is used to precisely control the emission wavelength within a narrow spectral range without mode-hops. The phase section is further connected to a coupled resonator cavity defined by two micro ring resonators 1320, 1330 having slightly different cavity lengths and thus different free-spectral ranges. The coupled micro ring resonator cavity is closed with a wide band reflector 1340. In the embodiment illustrated in the figures, the wide-band reflector 440 is represented as a folded (closed-loop) 2×2 Mach-Zehnder interferometer (MZI). The combination of features 800, 1300, 1310, 1320, 1330 and 1340 form a widely tunable external cavity laser. This external cavity is connected to a 1×2 Mach-Zehnder interferometer 1350, where one arm is used to out-couple the laser signal from the system-on-a-chip via a grating coupler 1380 which is connected to an optical fiber interface. In order to know the laser wavelength and signal intensity at all times, the wavelength/signal monitoring section 1360 is connected to the other arm of the 1350 1×2 Mach-Zehnder interferometer.

In FIGS. 13 and 14, the wavelength/signal monitoring section 1360 is shown as a non-balanced 1×2 Mach-Zehnder interferometer—where the optical path of the upper arm is different from that of the lower arm. Both outputs are connected to separate surface grating couplers 1390 and 1395 that are used for system power and wavelength tracking. These grating couplers are coupled to flip-chip photodiodes bonded on top directly. In general it is also possible to add additional grating couplers 1370 to monitor optical signal within different sections of the system-on-a-chip. In the illustrated example, grating coupler 1370 is used to monitor the optical signal from the gain-chip after the first micro ring resonator.

The described system-on-a-chip is further controlled by electrical signals in the form of resistive heaters as shown in FIG. 14. Here, the heater 1400 is used for constant phase shift control of the tunable laser. Heaters 1410, 1420 are used to control the lasing wavelength of the coupled micro ring cavity and to control the wavelength change. Heater 1440 is used to control the reflectivity of the wideband reflector, and heater 1430 is used to control the optical signal splitting ratio between the upper and lower arms of the 1×2 MZI 1350. The heaters are connected to contact pads 1450 on one side of the chip, which is typically opposite the side where the grating couplers are realized. Drive signals are controlled by a microprocessor, where the complete signal processing takes place.

Figure 15:
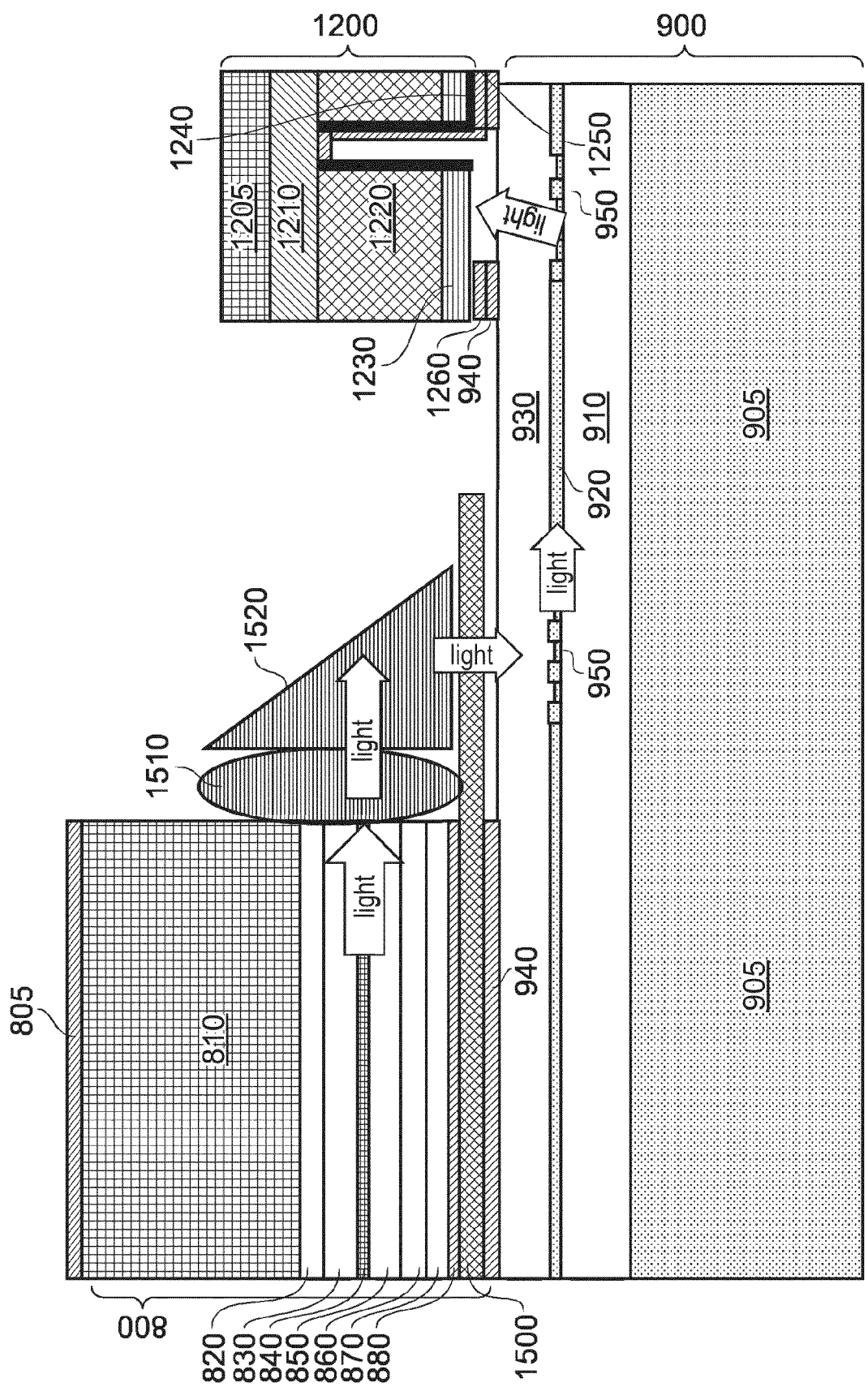
FIG. 15 is a schematic representation of hybrid integration of the III-V gain-chip to the silicon-on-insulator photonic integrated circuit, in accordance with an embodiment of the invention.

Referring to FIG. 15, a hybrid system on a chip can also be realized coupling the III-V gain-chip to the group IV semiconductor chip via a surface grating coupler instead of edge-coupling. Here, the gain-chip 800 is bonded to the submount, which can be a ceramic or metal carrier 1500, and pre-aligned with collimation lens 1510 and reflector prism 1520, forming a micro-optics bench. The entire assembly is then aligned over the grating coupler 950 and fixed to a top surface of the group-IV semiconductor chip 900 with solder or epoxy. The light from the gain-chip is collected via collection and collimation optics 1510 and reflected into a surface grating coupler via a prism or a mirror 1520. The grating coupler couples the reflected light into a silicon waveguide 920, where the remaining portion of the system-on-a-chip is realized. While this hybrid integration is typically more straight-forward, an edge-coupling configuration may generally be more efficient.

In an embodiment, the laser signal from a system-on-a-chip is coupled to a fiber-optic interface via a grating coupler, such as the grating coupler 1380 illustrated in FIG. 13. The fiber optic interface may consist of an optical fiber, i.e., a fiber probe, through which the light is guided from the sensor to a probe tip that is in optical communication with the target, e.g., the blood of the patient. In the case of an invasive measurement, the fiber probe may include two fiber cores and connect to an optical catheter that enters the vein or artery of a patient.

Figure 16:
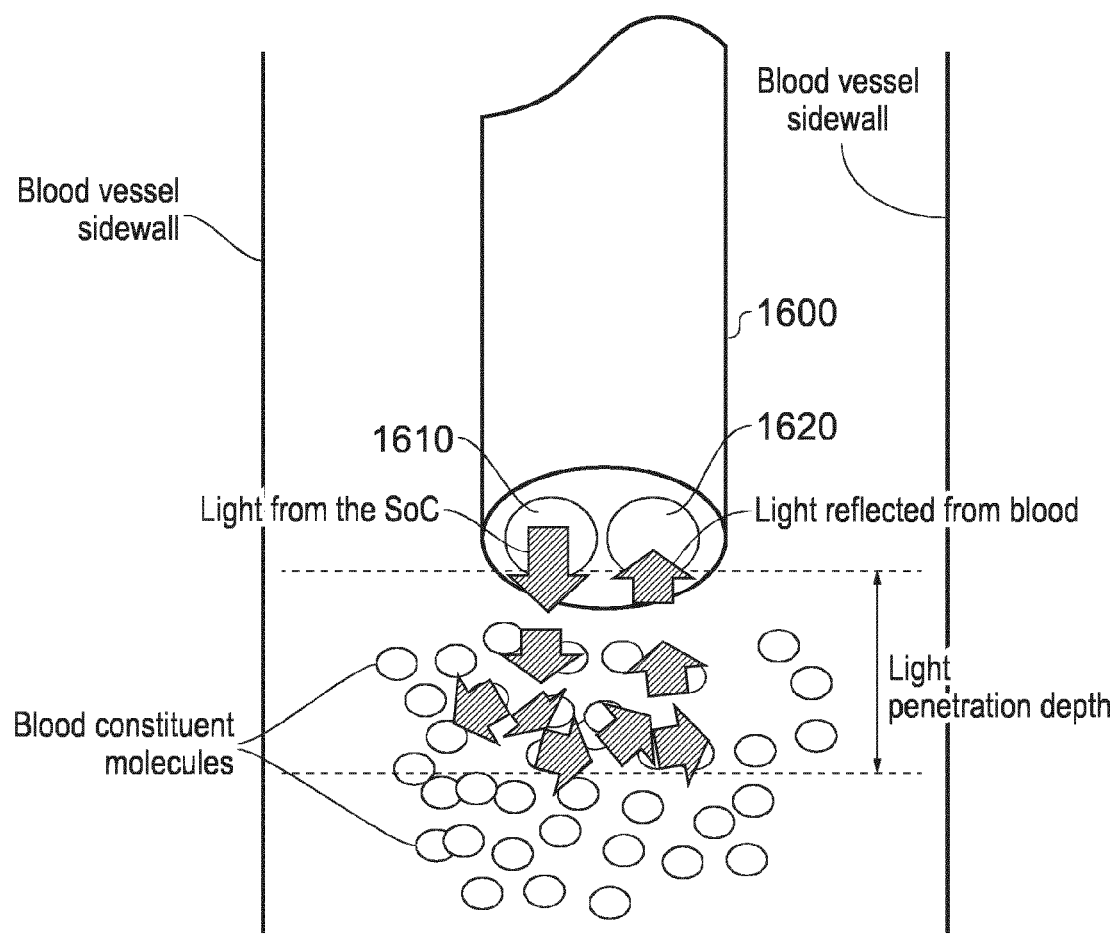
FIG. 16 is a schematic representation of a fiber probe in the case of invasive sensor, illustrating the basic principle of operation based on diffuse reflection, in accordance with an embodiment of the invention.

A catheter probe 1600 in direct contact with blood is shown in FIG. 16. Here, the probe 1600 includes at least two fiber cores. A first core 1610 is used to transmit light from the system-on-a-chip that is outside of the human body. The light interacts with blood constituent molecules and undergoes numerous scattering and absorption processes. This is a stochastic process and the scattering of light is direction independent. Referring also to FIGS. 1A-1C and 2, part of the scattered light is reflected back into the probe and is collected via a second fiber core 1620 that guides the collected light to a discrete photodiode 40. In the described embodiment, the system-on-a-chip sends a time signal when the laser emission wavelength is swept as a time function across the gain-bandwidth. During a scattering process with a blood-consistent molecule, a resonant absorption process takes place if the laser emission frequency matches the rotational-vibrational frequency of the target molecule. Such a process results in the change of the time signal collected by the discrete photodiode 40. Since the laser emission wavelength is known precisely at all times, the collected time signal can be reconstructed into wavelength space and molecular absorption spectrum can be determined, and concentration level of the target molecule can be evaluated.

Figure 17:
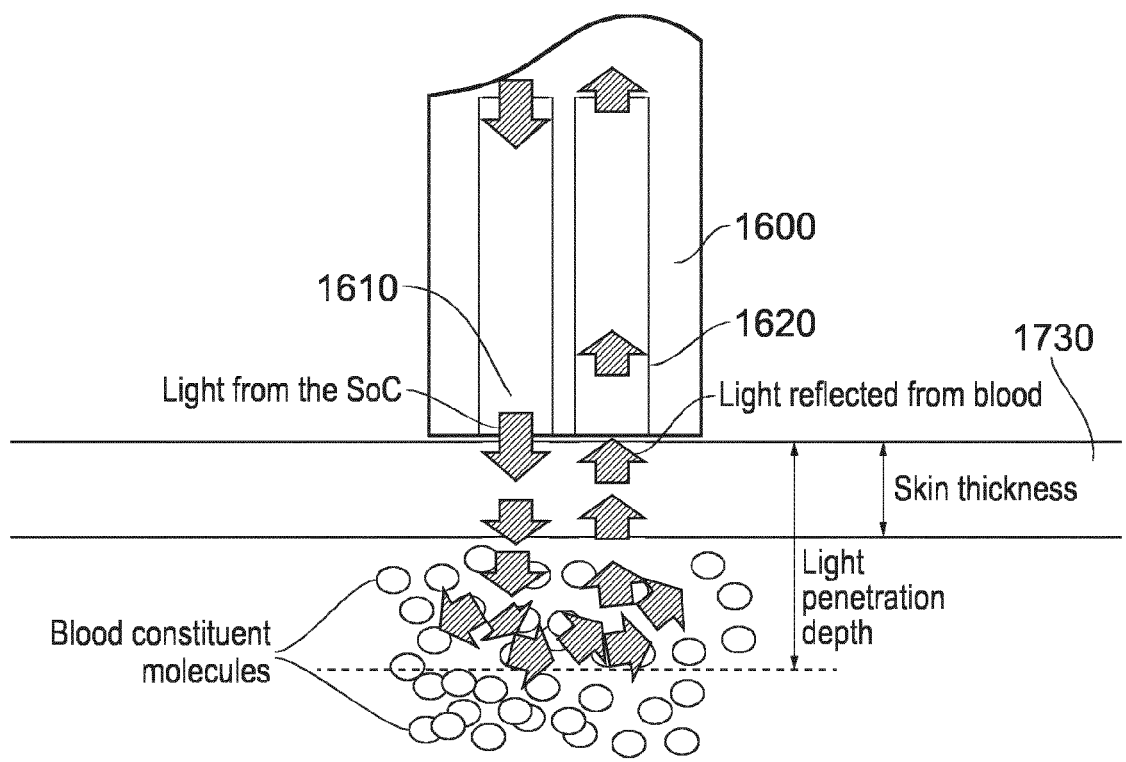
FIG. 17 is a schematic representation of a fiber-optic probe in case of non-invasive sensing, with the fiber probe 2D cross section is shown for clarity, in accordance with an embodiment of the invention.
Figure 18:
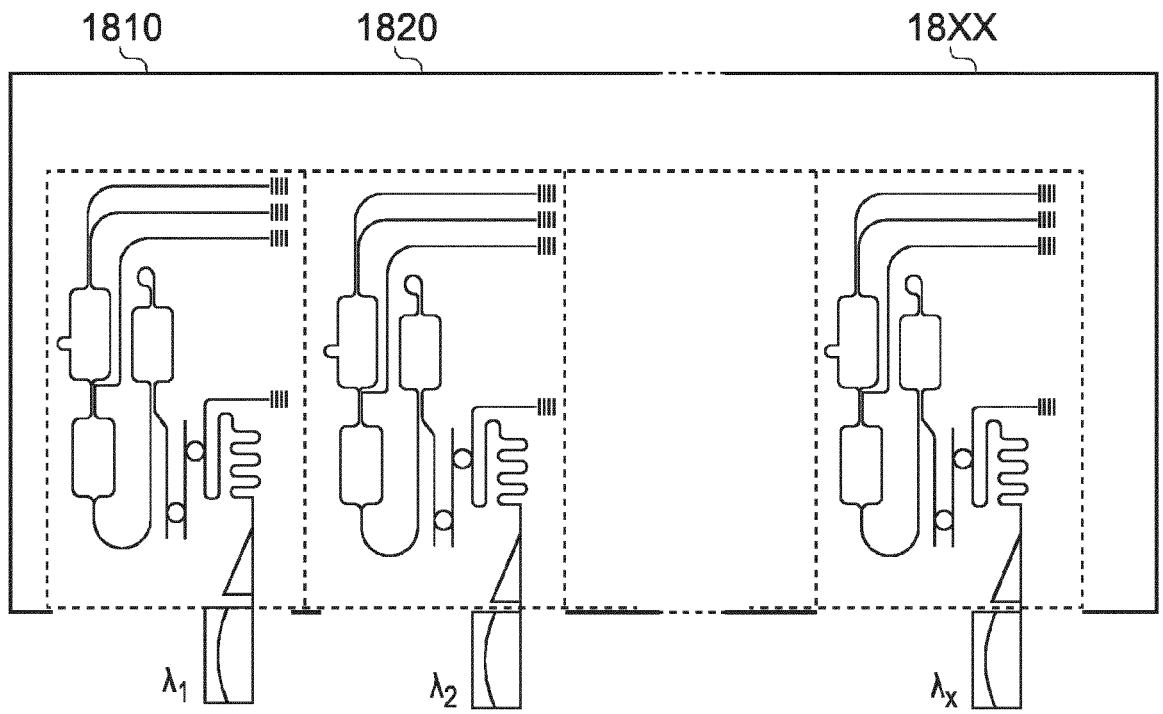
FIG. 18 is a schematic representation of forming an array of systems-on-a-chip for multiple molecule detection, in accordance with an embodiment of the invention.

For a non-invasive sensor, the fiber-optic interface that includes a probe does not connect to an intravascular catheter; rather, it is put into contact with skin as shown in FIG. 17. It may also be connected to a fingernail of a patient. The structure of the fiber probe 1600 is very similar to the one used in the invasive case. Again, at least two fiber cores are used. A first fiber core 1610 is used for coupling the light from the system-on-a-chip. The light out-coupled from the fiber core 1610 penetrates through outer skin layer 1730 such as epidermis and interacts with blood constituent molecules, which are below the epidermis, in the dermis and subcutaneous tissue. The backscattered light is collected via the second fiber core 1620 which guides the light to a discrete photodiode 40 at the sensor. The laser signal is converted as a function of time and is then converted into wavelength space and molecular absorption spectra are recovered, and concentration levels identified.

For infrared wavelengths close to and longer than 2 microns, typical penetration depth is a few millimeters. However, this is sufficient to reach the target blood molecules where the outer skin layer is sufficiently thin, for instance, under the fingernails, earlobe, wrist, etc.

The described embodiments of the invention employ advanced integrated technology that does not use mechanically movable parts, and all drive signals are based on electronics and photonics. The system-on-a-chip is controlled via a standard microcontroller, which controls the gain-chip drive current, SoC heater currents based on the signal information gathered from signal and wavelength monitoring sections, and compares the laser signal out-coupled from the sensor with the collected signal. This allows the elimination of systematic errors due to the system so that the signal change due to interaction with the target molecule can be identified.

Figure 19:
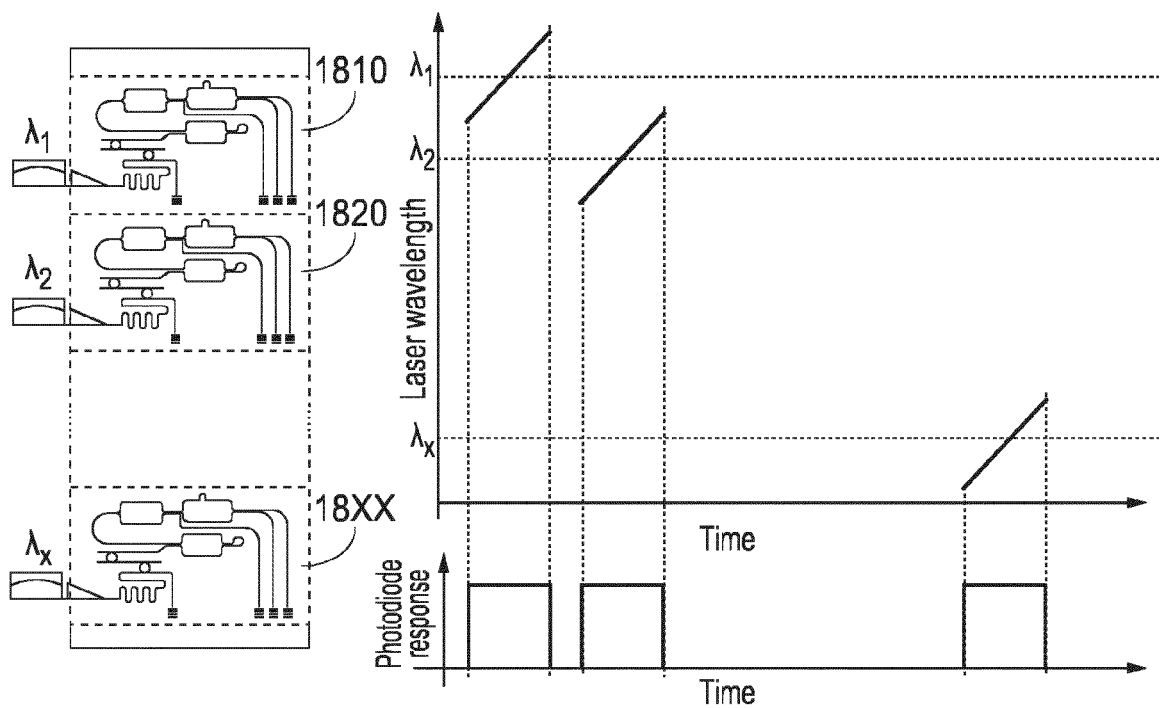
FIG. 19 is a schematic representation of synchronized detection using an array of lasers based on hybrid system-on-a-chip and a single discrete photodiode, in accordance with an embodiment of the invention.

Moreover, embodiments of the invention can be easily scaled to form a multiple molecule sensor. This may be achieved by forming an array of optical system-on-a-chip as in FIG. 18. Here the passive integrated optical circuit array is realized within the same silicon based wafer. In case different target molecules with unique absorption features in different spectral regions that cannot be accessed within the gain-bandwidth of the single III-V gain-chip, the photonic integrated circuit in silicon based chip may be designed in the form of linear array, where each array cell is design for a specific wavelength of interest, e.g., array cell 1810 is designed around center wavelength $\lambda_1$, array cell 1820 is designed around a wavelength centered at $\lambda_2$, etc. Each individual laser cell out-couples to an individual output fiber via an individual grating coupler. These fibers can be formed into a fiber bundle at the fiber probe end. The reflected signal, which carries information about each target molecule, can be collected with a single discrete photodiode, given each laser cell wavelength sweep is emitted at different known time intervals, and detection is synchronized, as shown in FIG. 19.

Figure 20:
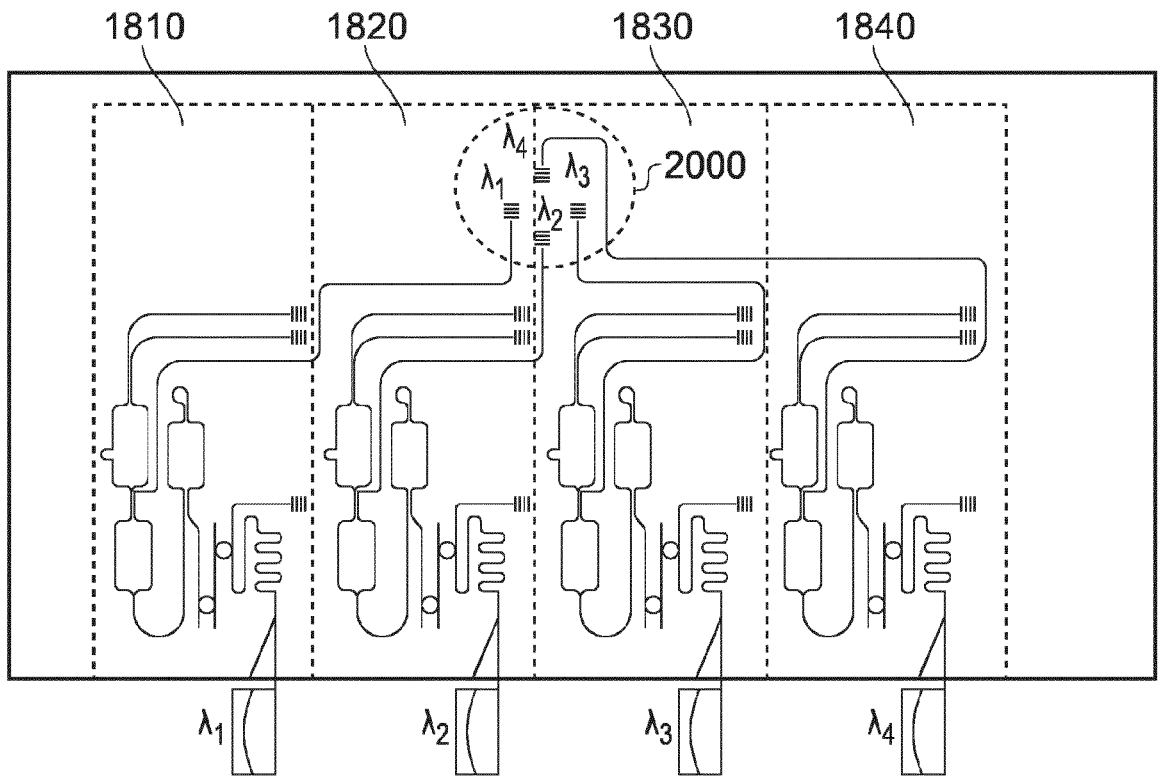
FIG. 20 is a schematic representation of an array of systems-on-a-chip for multiple molecule detection using a single output fiber and multiple surface grating couplers, in accordance with an embodiment of the invention.
Figure 21:
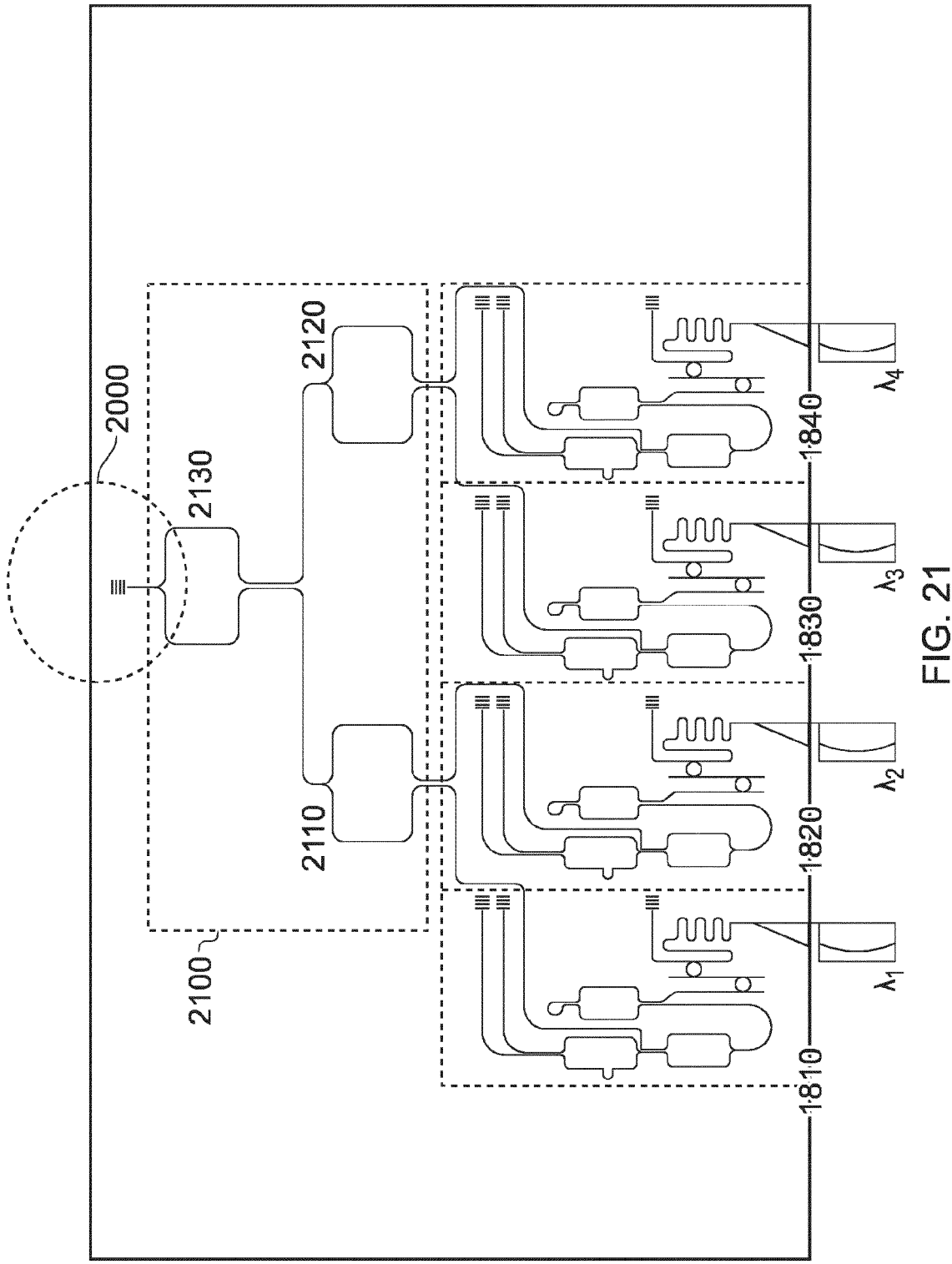
FIG. 21 is a schematic representation of an array of systems-on-a-chip for multiple molecule detection using a single output fiber, a wavelength switch, and a single grating coupler, in accordance with an embodiment of the invention.
Figure 22:
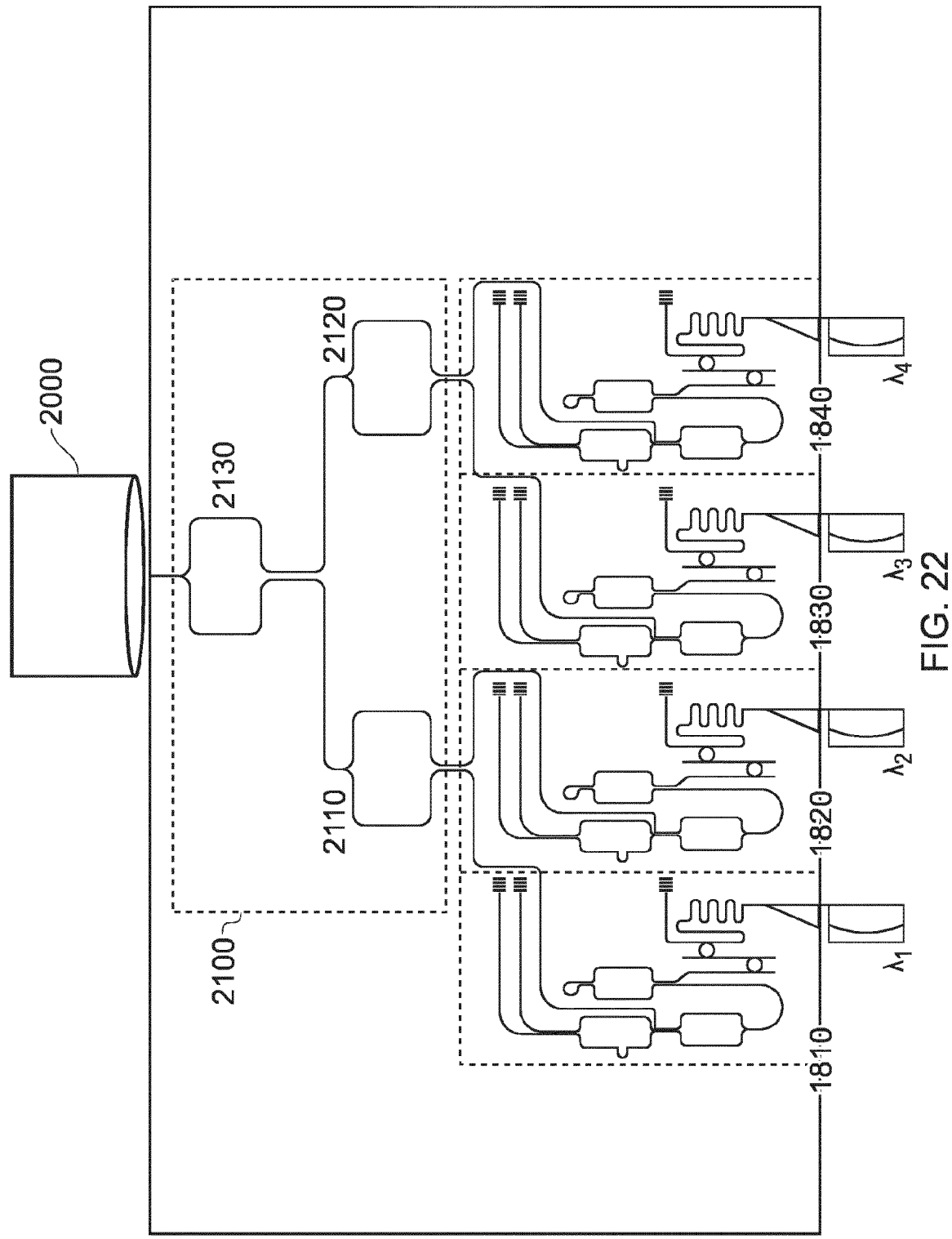
FIG. 22 is a schematic representation of an array of systems-on-a-chip for multiple molecule detection using a wavelength switch and a single end-fire output fiber configuration, in accordance with an embodiment of the invention.

For further optimization, the output of the SoC array can be organized couple to a single fiber core as shown in FIGS. 20, 21, and 22. Referring to FIG. 20, an array includes four array cells 1810, 1820, 1830, 1840, and each individual cell output may be formed by individual grating couplers, which are routed to an area of the chip where the grating couplers can be covered with a single multimode fiber core 2000. In such an embodiment, the number of cells in the array from which output may be collected with the single fiber core is limited by the fiber core cross-sectional area.

Another possibility is to use a wavelength switch and single grating coupler as shown in FIG. 21. Here, an array of four different cells 1810, 1820, 1830, 1840 is illustrated, with the cells emitting at four different wavelength bands. Each cell is routed to a wavelength switch 2100, which can be realized, for example, by a set of balanced Mach-Zehnder interferometers 2110, 2120, 2130. A first MZI 2110 may be used to switch (using. e.g., heaters integrated on the arms of the MZI) between wavelengths $\lambda_1$ and $\lambda_2$ generated by the first and second SoC cells 1810 and 1820. In the same manner, a second balanced MZI 2120 may be used to switch between wavelengths $\lambda_3$ and $\lambda_4$ generated by the third and fourth SoC cells 1830 and 1840. A third MZI 2130 switches between outputs of the first and second MCIs 2110 and 2120, controlling which cell of the four is out-coupled via a single grating coupler at any given moment of time. This concept can be scaled to an arbitrary number of individual cells while still maintaining a single grating coupler for the output of the array.

In the same manner, an SoC array can be realized using a single output and a single output fiber 2000 in an end-fire coupling configuration as shown in FIG. 22.

Figure 23:
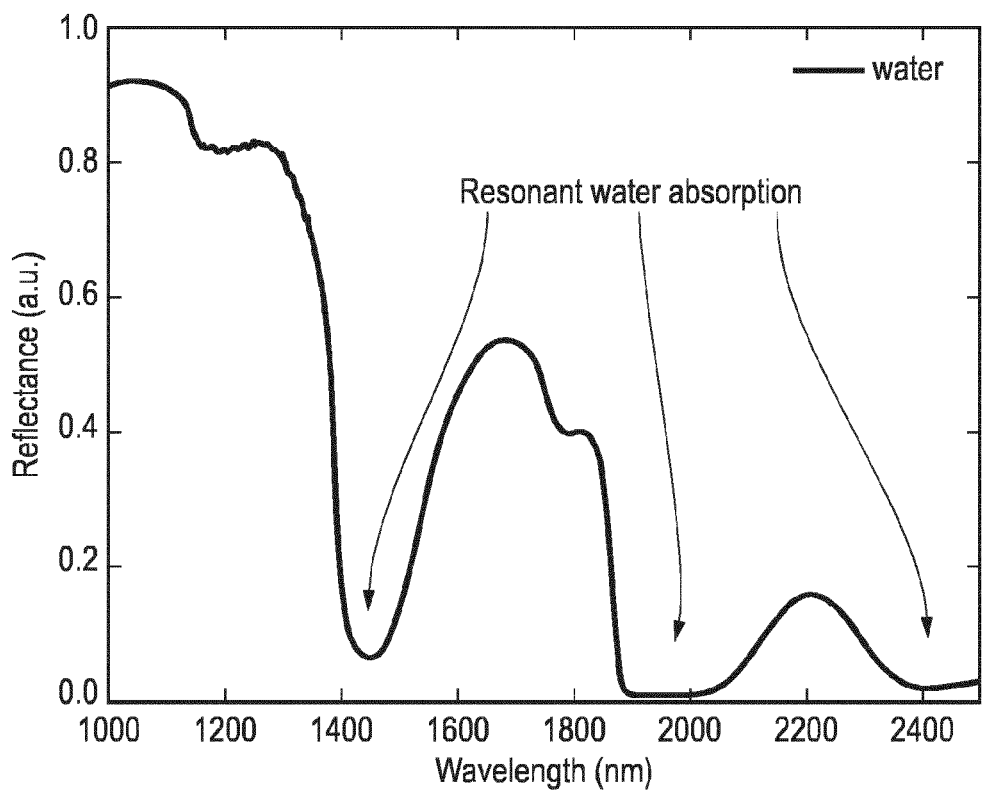
FIG. 23 is a diffuse reflectance spectrum of water, obtained by FTIR measurement.

To obtain calibrated concentration level data for a target metabolite, the concentration of other interfering molecular species contributing to the spectral signature must be known. By far the most dominant overlapping spectral signature is that of the water molecule, which contributes to over 95% of the total signal. In an embodiment of the invention, a sensor array has at least two sensor cells, with at least one of the cells being designed to have spectral wavelength tuning bandwidth in the vicinity of a water absorption peak. Referring to FIG. 23, water absorption peaks occur at ~1460 nm, ~1900-2000 nm or ~3000 nm. Thus, depending on the final sensor architecture, the cell's spectral wavelength tuning bandwidth can be near one of these peaks, where water molecular absorption, which has a very well-known spectrum, is dominant.

The diffuse reflectance measurement using this sensor architecture may be used to collect diffuse reflectance spectra $R(\lambda)$, which in turn can be converted to absorbance $A(\lambda)$ by the relation:

$$A(\lambda) = \log_{10}\left(\frac{1}{R(\lambda)}\right).$$

The collected absorbance spectrum is composed of a sum from individual absorbance spectral components of the contributing molecular species:

$$A(\lambda) = \sum_i A(\lambda)_i = A(\lambda)_{H2O} + A(\lambda)_{lactate} + A(\lambda)_{Glucose} + \cdots$$

Using the proposed sensor array architecture, a sensor may be designed such that each cell targets a different target molecule and individual absorbance spectra of each target molecule are decoupled by using the information from the adjacent cells operating in different spectral regions where no multiple interference occurs. In this way, one or more than one target component in the blood can be monitored.

Figure 24:
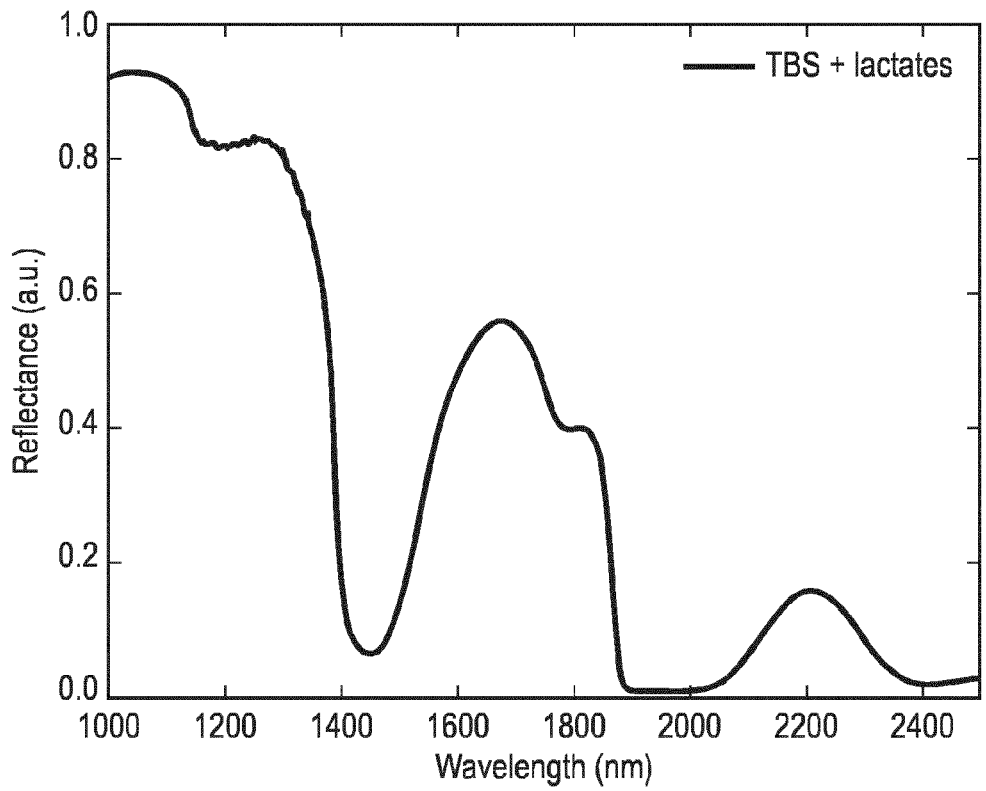
FIG. 24 is a diffuse reflectance spectrum of a tris buffer saline (TBS) solution with lactates obtained by FTIR measurement, in accordance with an embodiment of the invention.
Figure 25:
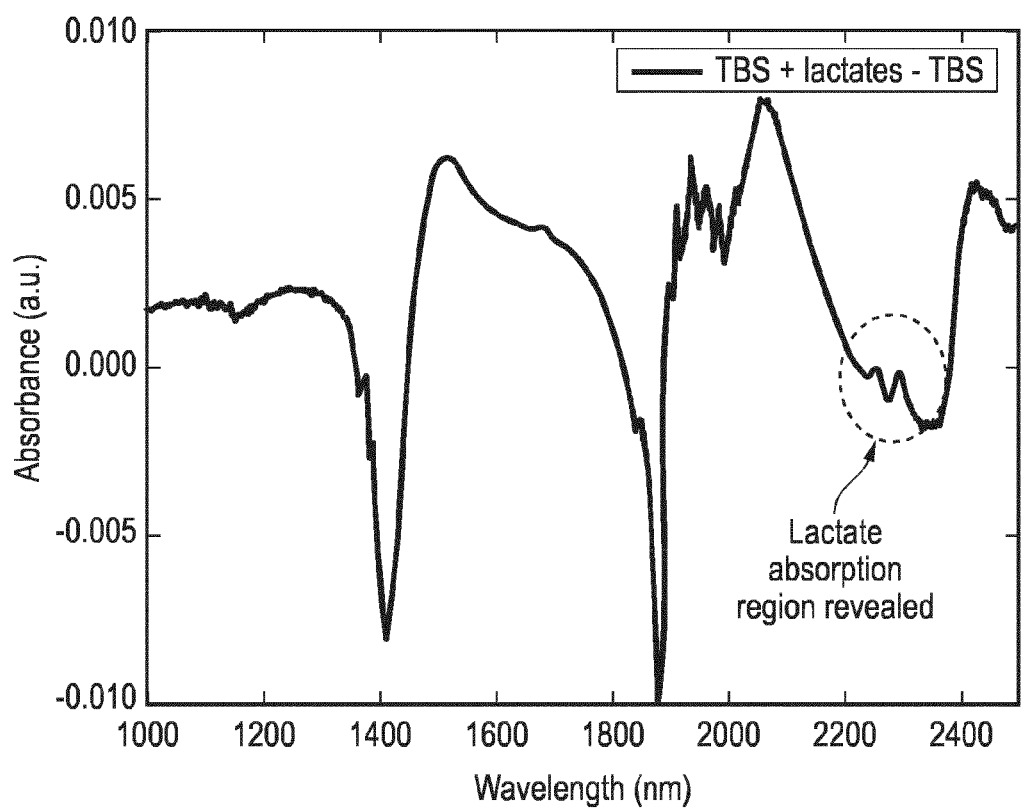
FIG. 25 is a processed spectrum in which the TBS spectral component was subtracted, revealing the spectral component of a lactate molecule, in accordance with an embodiment of the invention.

Referring to FIGS. 24-25, spectral decomposition may be performed as follows. FIG. 24 is a diffuse reflectance spectrum of a tris buffer saline (TBS) solution with lactates disposed in the solution, the spectrum having been obtained by FTIR measurement. FIG. 25 is a processed spectrum in which the TBS spectral component was subtracted, revealing the spectral component of a lactate molecule.

Accordingly, a very complex absorbance spectrum from a very complex scattering matrix—such as human tissue—can be decomposed into individual molecular absorbance components and this absorbance can in turn be converted to a calibrated concentration level by applying Lambert-Beer law:

$$A(\lambda)=\varepsilon_1(\lambda)c_1+\varepsilon_2(\lambda)c_2+\ldots$$

where $\varepsilon_i$ is the calibrated molar attenuation coefficient and $c_i$ is the concentration.

Calibrated attenuation coefficients for each individual molecules are predetermined and the values stored in the CPU for calibrated algorithm execution to process the experimentally obtained diffuse reflectance spectrum—i.e., to decompose the spectrum into individual absorbance spectral components and calculate calibrated concentration levels.

In particular, in an embodiment, a sensor may include an array of cells, with at least one array cell targeted at a spectral region corresponding to at least one peak of water absorption, i.e., ~1460 nm, ~1900-2000 nm, or ~3000 nm. Another cell in the array may be targeted at a spectral region corresponding to at least one absorption peak of a blood constituent target molecule. The sensor may include a CPU that is programmed to determine a water concentration level and a water absorption spectrum based on the at least one peak of water absorption measured with the at least one array cell. The CPU may also be programmed to remove a baseline and decompose a complex absorbance spectrum in spectral regions covered by array cells adjacent to the at least one array cell to reveal underlying target molecule absorption features. Further, the CPU may be programmed to convert diffuse reflectance spectra to absorbance. The absorbance may include a collected absorbance spectrum including a plurality of individual absorbance spectral components decoupled by using information from adjacent array cells operating in different spectral regions where no overlap with other molecular absorption exists.

Since the depth and density of the capillary network varies within different body parts, the sample volume also varies, and so does the reflectance signal. This challenge can be overcome with the described approach, in which a sensor array that includes a sensor cell targeting water or other known molecule in the spectral region with no interference is used. Thus, the water concentration level, which is also proportional to the sample volume, can be obtained independently of the sensor position within the human body, and the obtained data can further be used to remove baseline and decompose the complex absorbance spectrum in the spectral regions covered by adjacent sensor cells.

The described algorithm in combination with the sensor architecture described herein allows one to decompose an absorption spectrum of arbitrary complexity into individual components and thus evaluate of the concentration of each individual constituent. This may be facilitated by having prior knowledge of individual attenuation coefficients of each individual interfering species at a given wavelength. In circumstances when the attenuation coefficients for some of the interfering species are not known, the ability to subtract any known or possible spectral contributions greatly improves the accuracy of signal processing algorithms such as multivariate partial least squares and principle component regression method to obtain a calibrated concentration level of a target molecule.

The described sensor architecture technology allows the decomposition of a complex absorption spectra into individual components. When individual attenuation coefficients for every individual molecule are known, this technology provides a very straightforward way to get calibrated concentration levels of each spectral component. However, the complexity of blood may create challenges. In such cases a typical approach may include the use of multivariate PLS, which does not require all the underlying components to be known. Even for PLS, the ability to subtract major interfering components such as water greatly improves the accuracy of the algorithm. Accordingly, in a preferred embodiment, the sensor has attenuation coefficient data for several main molecules, and uses this information together with the water signal to remove the baseline and use multivariate PLS to get a calibrated concentration of the target molecule.

Figure 26:
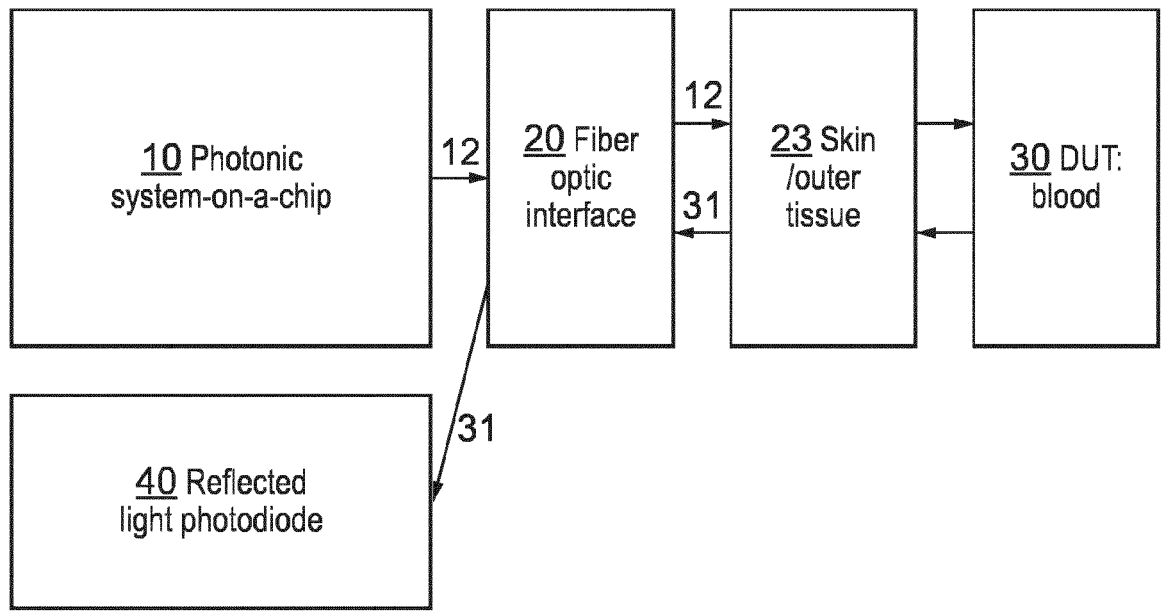
FIG. 26 is a simplified block diagram of laser-based system-on-a-chip-sensors configured for non-invasive measurement, in accordance with an embodiment of the invention.
Figure 27:
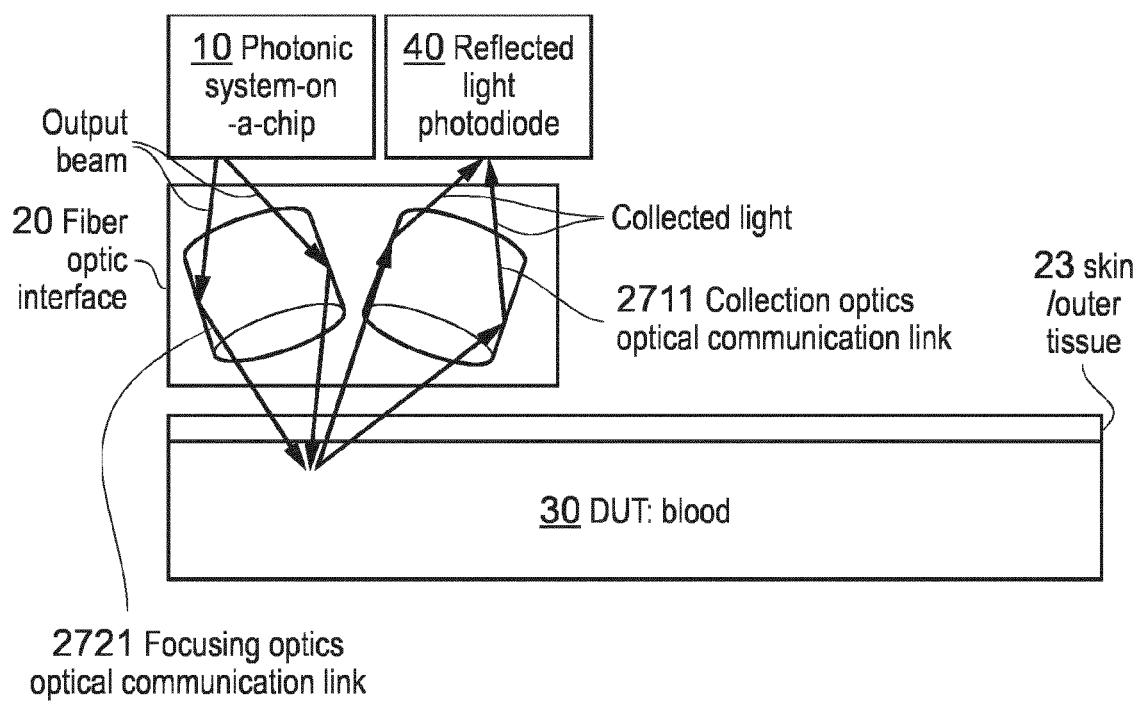
FIG. 27 is a simplified block diagram of a laser-based system-on-a-chip sensor in which the fiber-optic interface is realized with discrete beam shaping optics for focusing of the optical signal and collecting the diffuse reflection from the subject's blood non-invasively, in accordance with an embodiment of the invention.

Referring to FIGS. 1C, 26, and 27, the described sensor may be used for non-invasive concentration measurements, with the optical interface, e.g., fiber-optic interface 20, being used with additional beam shaping optics to illuminate the blood in the dermis layer under the outer skin layer or tissue via an optical link 2721. The reflected signal from blood is collected via the optical link 2711 and guided to the reflected light photodiode 40. This situation is shown in greater detail in FIG. 27, where the optical interface, e.g., fiber-optic interface 20 is depicted as consisting of a focusing optics optical link 2721 and a collection optics optical link 2711.

In some embodiments the optical communication links 2721 and 2711 are fibers, e.g., optical fibers 12 and 31. In other embodiments, each optical communication link 2721 and 2711 may be an optical element, i.e., a lens or a set of lenses, a set of mirrors, and/or a parabolic mirror that form the optical communication link.

For example, the sensor array may have its output grating couplers routed to a closely packed group in the same location within the optical chip, as is shown in FIG. 20, except the multimode fiber core 2000 may be replaced with a single focusing lens that focuses the output of each grating coupler on to the subject's blood under the outer layer of the skin non-invasively. The reflected light is collected by a separate lens, chosen so that its properties allow collection of light from the same depth and location where the focused light is sent, enabling sensing. The collected reflected light is then focused to a photosensitive aperture of the reflected light photodiode 40.

Figure 28:
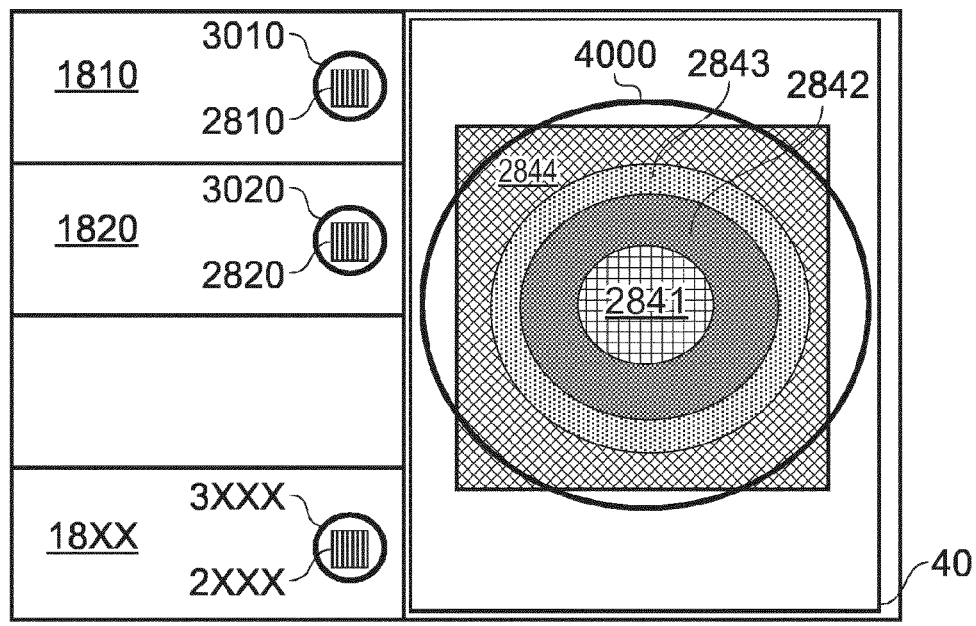
FIG. 28 is a block diagram of an embodiment of a sensor configuration in which the sensor includes an array of systems-on-a-chip with individual focusing optics to illuminate a sample and a single collection lens with a discrete photodiode for reflection signal collection, with the system-on-a-chip array being in a linear configuration with the reflected light photodiode, in accordance with an embodiment of the invention.

Referring to FIG. 28, during use of a system-on-a-chip sensor array, individual outputs of the photonic system-on-a-chip array cells 1810, 1820, . . . 18XX, each providing a swept wavelength laser signal around a different center wavelength, may be routed to one side of the photonic chip. Each individual output grating coupler 2810, 2820, . . . 2XXX is individually focused with an individual focusing optical element, for example, a lens 3010, 3020, . . . , 3XXX so that, in an optimal case, the beam spots of each the outputs overlap and form a single spot under the subject's skin, ensuring that the interaction between the light from the sensor and the subject's blood is localized to a defined location under the skin. Typical light penetration depth is up to 1 mm under the skin, reaching the first vascularized layer—dermis layer. The diffusely reflected light is then collected with a lens 4000, which is chosen so that its numerical aperture and focusing depth allows collection of the reflected light from the location to which the light is focused. This reflected light carries information about light-blood interaction and is collected by the lens 4000 and focused onto the photosensitive aperture 2841 of the reflected light photodiode 40. The photosensitive aperture 2841 is surrounded by a top electric contact 2842, which can act as a cathode or anode—depending on the actual photodiode epitaxial structure layer sequence—in combination with a second electrode 2844. The two electrodes are separated by an isolation gap 2843. For operation, the polarity between the electrodes 2842 and 2844 is chosen so that the pn-junction is reverse biased.

Figure 29:
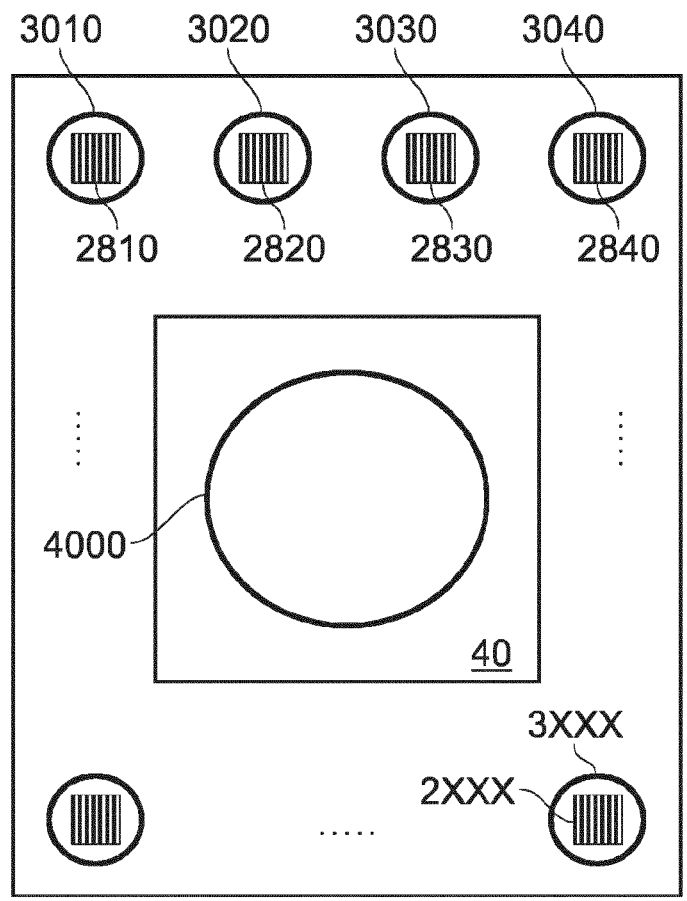
FIG. 29 is a block diagram of an embodiment of a sensor configuration in which the sensor includes an array of systems-on-a-chip with individual focusing optics to illuminate a sample and a single collection lens with a discrete photodiode for reflection signal collection disposed in the center of the system-on-a-chip array, in accordance with an embodiment of the invention.

The exact arrangement of the focusing optical lenses and the collection optical lenses is not critical as long as the focusing and collection is realized from the same location—i.e., the same spot—within the subject. This is illustrated in FIG. 29, where the collection lens 4000 and the photodiode 40 are realized in the center of the photonic chip array, whereas illumination of the sample is performed via the outputs routed to the perimeter of the photonic sensor chip.

Examples of Analysis

FIGS. 30a-30d shows absorption spectra of four molecules—glucose, lactate, bovine serum albumin and urea—recorded with a widely tunable laser based sensor (curves a), and compared with spectra recorded with a commercial table-top FTIR spectrometer (curves b). In particular, the tested solutions were a) 30 mmol/l glucose b) 50 mmol/l lactate c) 50 g/l bovine serum albumin (BSA) and d) 30 mmol/l urea. A clear correlation of the molecule-specific absorption spectrum measurement is visible.

Figure 31A:
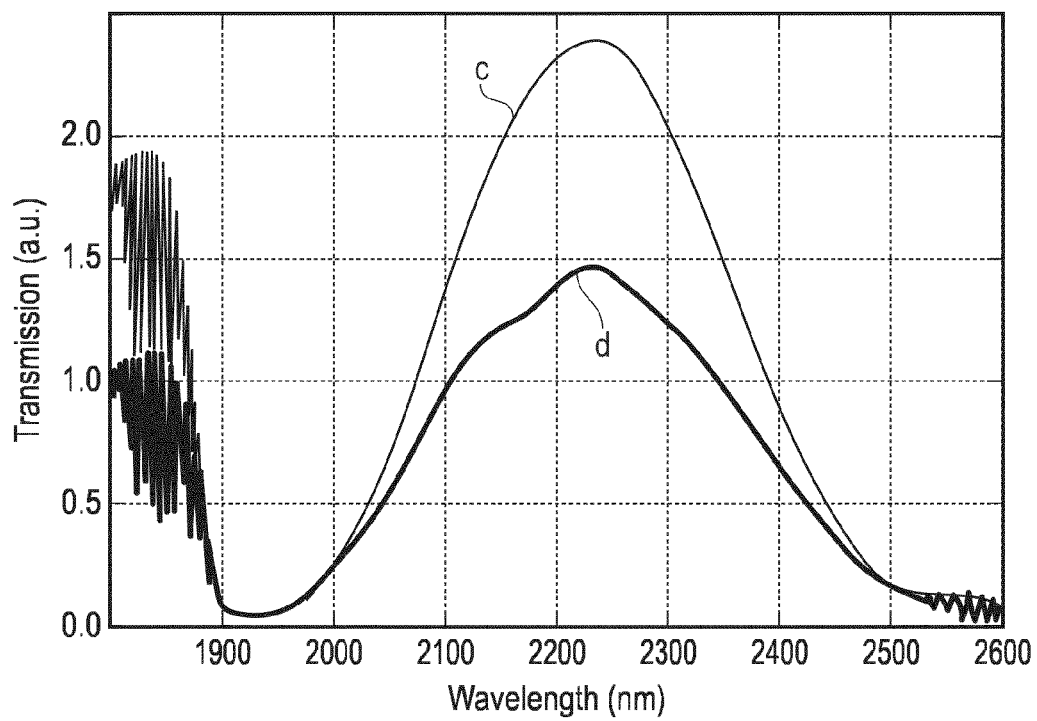
FIG. 31A-31B are spectroscopic measurements made using a commercial table-top FTIR spectrometer of human blood samples, when the dual core fiber tip is directly dipped into a blood droplet.
Figure 31B:
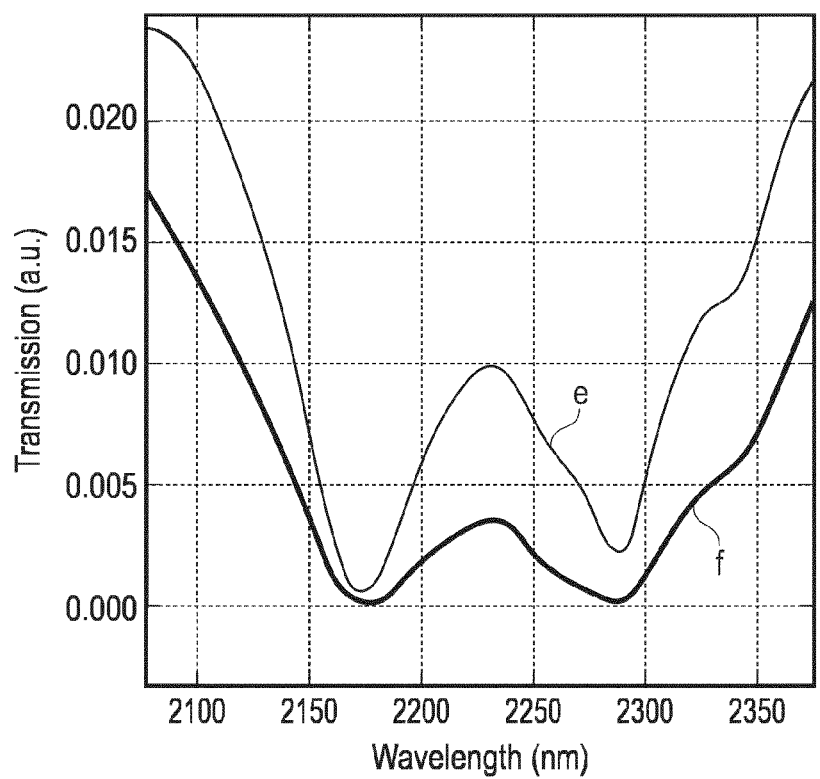

The CPU may be further programmed to correct and remove a baseline in spectral regions where absorption spectral features of more than one target molecule overlap. The baseline correction and removal is clearly illustrated in FIGS. 31a and 31b. These illustrate spectroscopic measurements made using a commercial table-top FTIR spectrometer of human blood samples, when the dual core fiber tip is directly dipped into a blood droplet. FIG. 31a depicts a transmission spectrum of a blood droplet (curve d) and fitted water reflection spectrum (curve c). FIG. 31(b) depicts blood spectra with water being subtracted from the blood transmission measurement. The resulting curve is depicted as curve f which includes all blood constituent molecules except water (subtracted). As a guideline, curve e is a measured transmission curve of bovine serum albumin (BSA), which closely resembles human serum albumin (HSA). Comparison of the two curves clearly indicates the spectral modulation from HSA on the blood measurement. The central processing unit may be further programmed to determine a calibrated concentration level using at least one of the individual absorbance spectral components, such as water or albumin. The calibrated concentration level may be determined based on an individual absorbance value and a calibrated attenuation coefficient for each of a plurality of individual molecules at a given wavelength. The central processing unit may be further programmed to determine a target molecule concentration independently of a particular sample volume.

Figure 32A:
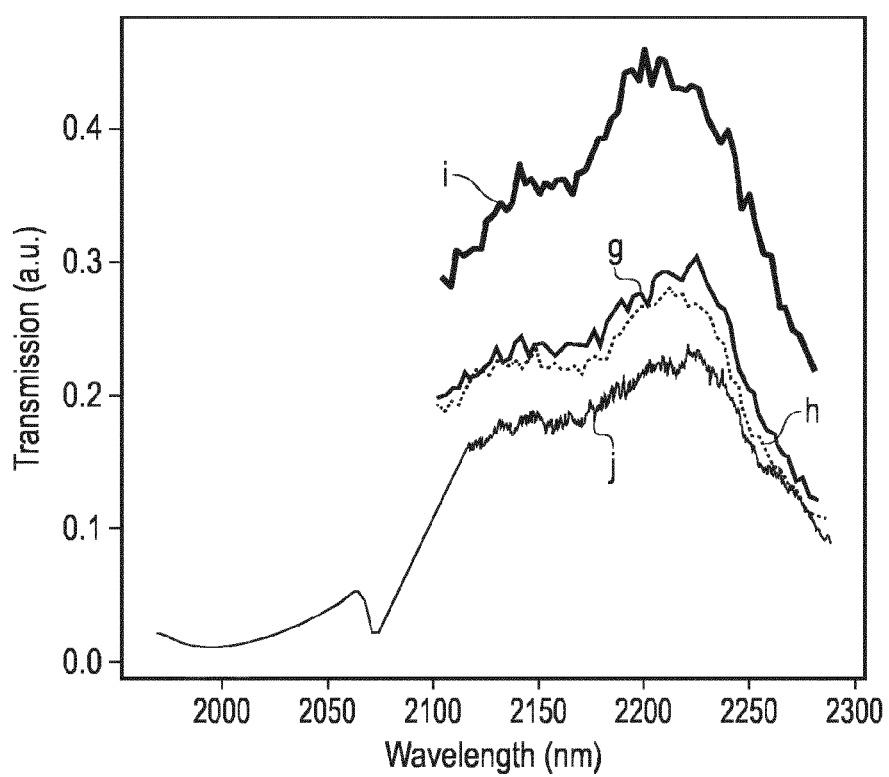
FIGS. 32A-32C are graphs illustrating experimental data obtained with non-invasive blood measurements via skin made using lasers in accordance with embodiments of the invention
Figure 32C:
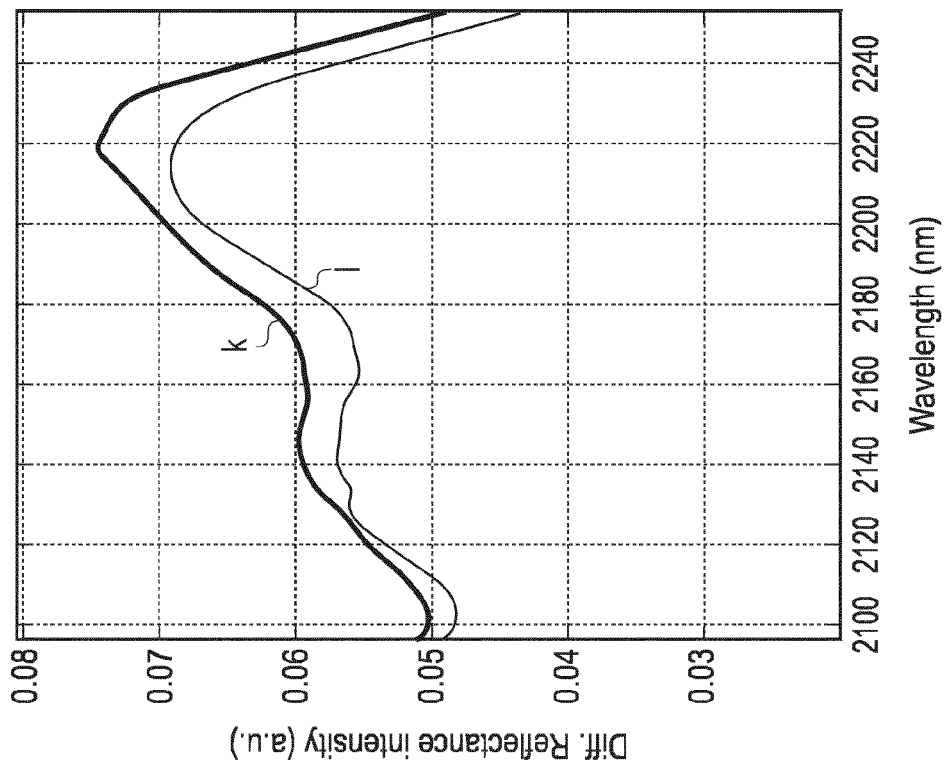
Figure 32B:
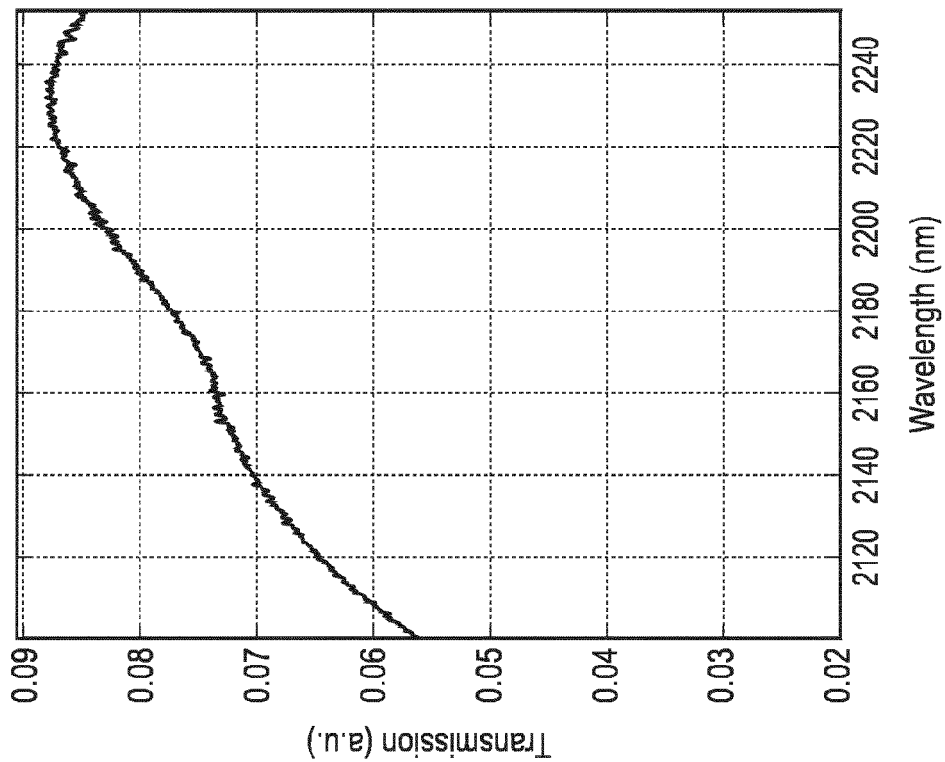

In the case of non-invasive measurements, the sensor sends the laser signal through skin, where light scatter and interacts with the tissue matrix. The laser signal reaches the upper capillary layer (~0.2-0.3 mm below epidermis), where the light interacts with blood. Generally, there are two types of reflectance: diffused and specular. Diffused reflectance is the dominant reflectance when light interacts with tissue. A diffuse reflectance signal form a non-invasive measurement of a human is shown in FIGS. 32a and 32b, where the shape of the complex reflectance spectrum measured non-invasively via skin of two different persons (FIG. 32a curves g and h) is compared with the invasive direct measurement of a blood droplet when the fiber probe is directly immersed into the blood (FIG. 32a curves i and j), clearly demonstrating the capability of non-invasive measurement. Furthermore, in a similar manner as in FIG. 31, spectral decomposition can be applied to reveal the signal of the underlying molecules in the blood, which can be seen in FIGS. 32b and 32c, where the blood signal modulation with human serum albumin is shown in both cases measured by a table top FTIR spectrometer (FIG. 32b) and non-invasively with a widely tunable laser sensor as described herein. Modulation from the dominant HSA molecule around 2170 nm is clearly visible.

The aforementioned specific chip arrangements are only a few examples of the many possible embodiments of the invention. The described embodiments of the invention are intended to be merely exemplary and numerous variations and modifications will be apparent to those skilled in the art. All such variations and modifications are intended to be within the scope of the present invention as defined in the appended claims.

The sensor system of the invention also contains the following features as set out in the clauses below:

1. A laser-based sensor system-on-a-chip for real-time monitoring of a blood constituent concentration level in a subject, the system-on-a-chip comprising:
   a tunable hybrid III-V/IV laser sensor; and
   a fiber-optic interface coupled to the laser sensor, the interface comprising a probe,
   wherein during use the laser sensor is remote from the subject and the probe is in optical communication with the subject.

2. A laser-based sensor system-on-a-chip of clause 1, wherein the IV comprises a IV-based semiconductor substrate selected from the group consisting of silicon, silicon-on-insulator, silicon nitride on silicon-on-insulator, germanium-on-insulator, and silicon nitride on silicon.

3. The laser-based sensor system-on-a-chip of clause 1, wherein the tunable laser sensor comprises a III-V gain-chip and a photonic integrated circuit disposed on a IV-based substrate, the photonic integrated circuit (i) being configured to perform wavelength filtering and tuning functions based on Vernier effect and (ii) defining an external cavity for the III-V gain-chip.

4. The laser-based sensor system-on-a-chip of clause 3, wherein the photonic integrated circuit comprises a spot-size mode converter, a phase control section, and a first resonator having a first free-spectral range coupled to a second resonator having a second free-spectral range.

5. The laser-based sensor system-on-a-chip of clause 4, wherein the first and second resonators are selected from the group consisting of micro ring resonators, sampled Bragg reflectors, and distributed feedback reflectors.

6. The laser-based sensor system-on-a-chip of clause 4, wherein the first free-spectral range is different from the second free-spectral range.

7. The laser-based sensor system-on-a-chip of clause 4, wherein the coupled first and second resonators, the III-V gain-chip, spot-size mode converter, and phase control section cooperate to enable Vernier effect-based tuning of the tunable laser sensor.

8. The laser-based sensor system-on-a-chip of clause 4, wherein the tunable laser sensor is configured such that, in operation, applying at least one of current or heat to at least one of the coupled resonators to change an effective refractive index thereof effects a change in a wavelength of a laser generated by the gain-chip.

9. The laser-based sensor system-on-a-chip of clause 3, wherein the III-V gain-chip is edge-coupled to the photonic integrated circuit.

10. The laser-based sensor system-on-a-chip of clause 9, wherein the III-V gain-chip is coupled to the photonic integrated circuit by a grating coupler.

11. The laser-based sensor system-on-a-chip of clause 1, wherein the laser sensor comprises at least one III-V photodiode coupled to a photonic integrated circuit by at least one of flip-chip bonding, gluing, transfer printing technology, or side coupling.

12. The laser-based sensor system-on-a-chip of clause 1, further comprising a discrete III-V photodiode disposed remotely from the tunable laser sensor, wherein, in use, a reflected signal from the subject is collected by the discrete III-V photodiode.

13. The laser-based sensor system-on-a-chip of clause 12, where the photonic integrated circuit comprises a signal and wavelength monitoring section.

14. The laser-based sensor system-on-a-chip of clause 13, wherein the signal and wavelength monitoring section comprises (i) at least one of a set of Mach-Zehnder interferometers or coupled ring resonators, and (ii) at least one flip-chip III-V photodiode.

15. The laser-based sensor system-on-a-chip of clause 14, where the laser sensor further comprises:
sensor control electronics; and
a signal processing microcontroller,
wherein the microcontroller is configured to (i) control the laser drive electronics, (ii) tune currents, and (iii) use information from the wavelength and signal monitor section for signal processing of the data obtained from the discrete III-V photodiode.

16. The laser-based sensor system-on-a-chip of clause 1, wherein the laser sensor is configured to perform a wavelength sweep across a tuning range as a function of time, and the laser sensor comprises a photodiode configured to convert light reflected from the subject into an electrical signal.

17. The laser-based sensor system-on-a-chip of clause 1, wherein the fiber-optic interface is connected to an optical catheter and is configured to (i) transmit a light signal from the sensor to blood of the subject and (ii) transmit reflected light from the blood of the subject to the sensor.

18. The laser-based sensor system-on-a-chip of clause 1, wherein the fiber optic interface is in optical communication with beam shaping optics configured to non-invasively illuminate a blood sample of the subject through the subject's skin or outer tissue.

19. A method of manufacturing a laser-based sensor system-on-a chip for real-time monitoring of a blood constituent concentration level in a subject, the method comprising the steps of:
manufacturing a tunable hybrid III-V/IV laser sensor by
manufacturing a III-V semiconductor gain-chip,
fabricating a photonic integrated circuit on a group IV-based semiconductor substrate by CMOS technology to define a group IV semiconductor chip, and
hybridly integrating the III-V gain-chip and the group IV semiconductor chip,
wherein the photonic integrated circuit is (i) configured to perform wavelength filtering and tuning functions based on Vernier effect and (ii) defines an external cavity for the III-V gain-chip; and
coupling a fiber-optic interface to the laser sensor, the interface comprising a probe,
wherein during use the laser sensor is remote from the subject and the probe is in optical communication with the subject.

20. The method of clause 19, wherein hybridly integrating the III-V gain-chip and the group IV semiconductor chip comprises edge-coupling the III-V gain-chip to the group IV semiconductor chip, actively aligning the two chips, and gluing the two chips together.

21. The method of clause 19, wherein hybridly integrating the chips comprises flipping the III-V gain-chip p-side down and bonding the gain-chip into a trench defined in the group IV semiconductor chip for edge coupling to the photonic integrated circuit.

22. The method of clause 19, wherein manufacturing the III-V semiconductor gain-chip comprises epitaxially growing a laser layer structure on a substrate by at least one of MBE or MOVPE growth.

23. The method of clause 22, further comprising processing the laser layer structure on the substrate into a gain-chip device comprising predefined waveguide angles and contact pads.

24. The method of clause 23, further comprising cleaving the laser layer structure on the substrate into bars.

25. The method of clause 24, further comprising forming an anti-reflection coating on an output facet, wherein power reflection is less than 0.1% at the output facet.

26. The method of clause 25, further comprising forming a high-reflectivity coating on a back facet, wherein power reflectivity is at least 90% or higher on the back facet.

27. The method of clause 26, further comprising cleaving each bar into a plurality of individual III-V semiconductor gain-chips.

28. The method of clause 27, further comprising designing a photonic integrated circuit according to properties of the III-V gain-chip, the photonic integrated circuit comprising at least one of a spot size converter and a Vernier-filter.

29. A sensor comprising an array of cells, each cell comprising a laser-based sensor system-on-a chip of clause 1, wherein each array cell is targeted at a different spectral region and a separate target molecule.

30. The sensor of clause 29, where a wavelength swept laser signal of each array cell is emitted at a different time, and signal collection is realized by synchronized detection with a single photodiode.

31. The sensor of clause 29, wherein (i) the fiber-optic interface comprises an out-coupling fiber having a core, (ii) an output of the array is formed by a group of grating couplers from the individual array cells routed to a same portion of the system-on-a-chip and (iii) a total area defined by the group of grating couplers is smaller than a cross-sectional area of the out-coupling fiber core.

32. The sensor of clause 29, further comprising:
a single output section;
a wavelength switch configured to switch between outputs of the array cells; and
a single photodiode,
wherein (ii) an output of the sensor array is formed by the single output section and the wavelength switch, (ii) switching between outputs of each individual cell results in a single output of one array cell being out-coupled to the target at a given time; and (iii) signal collection is realized by synchronized detection with the single photodiode.

33. The sensor of clause 29, wherein (i) at least one array cell is targeted at a spectral region corresponding to at least one peak of water absorption selected from the group consisting of ~1460 nm, ~1900-2000 nm, and ~3000 nm, and (ii) at least one other array cell is targeted at a spectral region corresponding to at least one absorption peak of a blood constituent target molecule.

34. The sensor of clause 33, further comprising at least one central processing unit programmed to determine a water concentration level and a water absorption spectrum based on the at least one peak of water absorption measured with the at least one array cell.

35. The sensor of clause 34, wherein the central processing unit is further programmed to remove a baseline and decompose a complex absorbance spectrum in spectral regions covered by array cells adjacent to the at least one array cell to reveal underlying target molecule absorption features.

36. The sensor of clause 33, wherein the central processing unit is further programmed to convert diffuse reflectance spectra to absorbance.

37. The sensor of clause 36, wherein the absorbance comprises a collected absorbance spectrum comprising a plurality of individual absorbance spectral components decoupled by using information from adjacent array cells operating in different spectral regions where no overlap with other molecular absorption exists.

38. The sensor of clause 37, wherein the central processing unit is further programmed to correct and remove a baseline in spectral regions where absorption spectral features of more than one target molecule overlap.

39. The sensor of clause 38, wherein the central processing unit is further programmed to determine a calibrated concentration level using at least one of the individual absorbance spectral components.

40. The sensor of clause 39, wherein the calibrated concentration level is determined based on an individual absorbance value and a calibrated attenuation coefficient for each of a plurality of individual molecules at a given wavelength.

41. The sensor of any of clauses 33-39, wherein the central processing unit is further programmed to determine a target molecule concentration independently of a particular sample volume.

42. A laser-based sensor system-on-a-chip for real-time monitoring of a blood constituent concentration level in a subject, the system-on-a-chip comprising:
a tunable hybrid sensor; and
an optical interface coupled to the laser sensor, the optical interface comprising beam-shaping optics,
wherein during use the laser sensor is remote from the subject, and the optical interface is configured to non-invasively illuminate a blood sample of the subject through the subject's skin or outer tissue.

43. A sensor comprising an array of cells, each cell comprising a laser-based sensor system-on-a chip of clause 42, wherein each array cell is targeted at a different spectral region and a separate target molecule.

44. The sensor array of clause 43, wherein an individual output of each array cell is focused to illuminate a single area of the subject, and each reflected signal is collected from the illuminated area by the beam shaping optics.

45. The sensor array of clause 42, wherein the beam shaping optics comprise at least one optical element.

46. The sensor array of clause 45, wherein the optical element comprises at least one of a lens, a set of mirrors, and a parabolic mirror.

47. A method of real-time monitoring of a blood constituent level in a subject, comprising the steps of:
providing a system-on-a-chip comprising
a tunable hybrid III-V/IV laser sensor,
a fiber-optic interface coupled to the laser sensor, the surface comprising a probe,
sensor control electronics for sensor control and signal processing, and
a signal processing microcontroller, disposing the laser sensor remote from the subject and the probe in optical communication with the subject;
instructing the system-on-a chip to monitor the blood constituent level in the subject by sending a swept laser signal to the fiber optic interface;
guiding the signal with the fiber optic interface to the blood of the subject;
after the signal interacts with the blood, collecting with the fiber-optic interface a reflected signal from the blood;
guiding the reflected signal to a reflected light photodiode, wherein the reflected signal is an optical signal;
converting the reflected signal from an optical signal to an electrical signal; and
processing the electrical signal with the microcontroller to convert the electrical signal into a calibrated blood constituent level.

48. The method of clause 47, wherein the probe is connected to at least one of an intravenous optical catheter or an intra-arterial optical catheter for invasive blood analyte concentration level measurement.

49. The method of clause 47, wherein the optical interface is attached to the subject for non-invasive blood analyte concentration level measurement.

50. The method of clause 47, wherein the blood constituent is selected from the group consisting of lactate, albumin, glucose, ammonia, creatinine, and urea.

The invention claimed is:
1. A laser-based sensor system-on-a-chip for real-time monitoring of a blood constituent concentration level in a subject, the system-on-a-chip comprising:
a tunable hybrid III-V/IV laser sensor comprising at least one III-V photodiode coupled to a photonic integrated circuit by at least one of flip-chip bonding, gluing, transfer printing technology, or side coupling, the photonic integrated circuit comprising a signal and wavelength monitoring section comprising (i) at least one of a set of Mach-Zehnder interferometers or coupled ring resonators, and (ii) at least one flip-chip III-V photodiode;
a fiber-optic interface coupled to the laser sensor, the interface comprising a probe, wherein during use the laser sensor is remote from the subject and the probe is in optical communication with the subject;
a discrete III-V photodiode disposed remotely from the tunable laser sensor, wherein, in use, a reflected signal from the subject is collected by the discrete III-V photodiode;
sensor control electronics; and
a signal processing microcontroller,
wherein the microcontroller is configured to (i) control laser drive electronics, (ii) tune currents, and (iii) use information from the wavelength and signal monitor section for signal processing of data obtained from the discrete III-V photodiode.

2. A sensor comprising:
an array of cells, each cell comprising a laser-based sensor system-on-a chip for real-time monitoring of a blood constituent concentration level in a subject, the system-on-a-chip comprising:
a tunable hybrid III-V/IV laser sensor; and
a fiber-optic interface coupled to the laser sensor, the interface comprising a probe,
wherein (i) during use the laser sensor is remote from the subject and the probe is in optical communication with the subject, (ii) each array cell is targeted at a different spectral region and a separate target molecule, (iii) a wavelength swept laser signal of each array cell is emitted at a different time, and (iv) signal collection is realized by synchronized detection with a single photodiode.

3. A sensor comprising:
an array of cells, each cell comprising a laser-based sensor system-on-a chip for real-time monitoring of a blood constituent concentration level in a subject, the system-on-a-chip comprising:
a tunable hybrid III-V/IV laser sensor; and
a fiber-optic interface coupled to the laser sensor, the interface comprising a probe,
wherein (i) during use the laser sensor is remote from the subject and the probe is in optical communication with the subject, (ii) each array cell is targeted at a different spectral region and a separate target molecule, (iii) the fiber-optic interface comprises an out-coupling fiber having a core, (iv) an output of the array is formed by a group of grating couplers from the individual array cells routed to a same portion of the system-on-a-chip and (v) a total area defined by the group of grating couplers is smaller than a cross-sectional area of the out-coupling fiber core.

4. A sensor comprising:
an array of cells, each cell comprising a laser-based sensor system-on-a chip for real-time monitoring of a blood constituent concentration level in a subject, the system-on-a-chip comprising:
a tunable hybrid III-V/IV laser sensor;
a fiber-optic interface coupled to the laser sensor, the interface comprising a probe,
a single output section;
a wavelength switch configured to switch between outputs of the array cells; and
a single photodiode,
wherein (i) during use the laser sensor is remote from the subject and the probe is in optical communication with the subject, (ii) each array cell is targeted at a different spectral region and a separate target molecule, (iii) an output of the sensor array is formed by the single output section and the wavelength switch, (iv) switching between outputs of each individual cell results in a single output of one array cell being out-coupled to the target at a given time; and (v) signal collection is realized by synchronized detection with the single photodiode.

5. A sensor, comprising:
an array of cells, each cell comprising a laser-based sensor system-on-a chip for real-time monitoring of a blood constituent concentration level in a subject, the system-on-a-chip comprising:
a tunable hybrid III-V/IV laser sensor; and
a fiber-optic interface coupled to the laser sensor, the interface comprising a probe,
wherein (i) during use the laser sensor is remote from the subject and the probe is in optical communication with the subject, (ii) each array cell is targeted at a different spectral region and a separate target molecule, (iii) at least one array cell is targeted at a spectral region corresponding to at least one peak of water absorption selected from the group consisting of ~1460 nm, ~1900–2000 nm, and ~3000 nm, and (iv) at least one other array cell is targeted at a spectral region corresponding to at least one absorption peak of a blood constituent target molecule.

6. A sensor array, comprising:
an array of cells, each cell comprising a laser-based sensor system-on-a-chip for real-time monitoring of a blood constituent concentration level in a subject, the system-on-a-chip comprising:
a tunable hybrid III-V/IV sensor; and
an optical interface coupled to the laser sensor, the optical interface comprising beam-shaping optics,
wherein (i) during use the laser sensor is remote from the subject, and the optical interface is configured to non-invasively illuminate a blood sample of the subject through the subject's skin or outer tissue, (ii) each array cell is targeted at a different spectral region and a separate target molecule, and (iii) an individual output of each array cell is focused to illuminate a single area of the subject, and each reflected signal is collected from the illuminated area by the beam shaping optics.

7. A method of real-time monitoring of a blood constituent level in a subject, comprising the steps of:
providing a system-on-a-chip comprising
a tunable hybrid III-V/IV laser sensor,
a fiber-optic interface coupled to the laser sensor, the surface comprising a probe,
sensor control electronics for sensor control and signal processing, and
a signal processing microcontroller,
disposing the laser sensor remote from the subject and the probe in optical communication with the subject;
instructing the system-on-a chip to monitor the blood constituent level in the subject by sending a swept laser signal to the fiber optic interface;
guiding the signal with the fiber optic interface to the blood of the subject;
after the signal interacts with the blood, collecting with the fiber-optic interface a reflected signal from the blood;
guiding the reflected signal to a reflected light photodiode, wherein the reflected signal is an optical signal;
converting the reflected signal from an optical signal to an electrical signal; and
processing the electrical signal with the microcontroller to convert the electrical signal into a calibrated blood constituent level.

8. The method of claim 7, wherein the probe is connected to at least one of an intravenous optical catheter or an intra-arterial optical catheter for invasive blood analyte concentration level measurement.

9. The method of claim 7, wherein the optical interface is attached to the subject for non-invasive blood analyte concentration level measurement.

10. The method of claim 7, wherein the blood constituent is selected from the group consisting of lactate, albumin, glucose, ammonia, creatinine, and urea.

* * * * *